(12) United States Patent
Rogers et al.

(10) Patent No.: US 7,799,913 B2
(45) Date of Patent: Sep. 21, 2010

(54) CARBONYLBENZOXAZINE COMPOUNDS FOR ENHANCING GLUTAMATERGIC SYNAPTIC RESPONSES

(75) Inventors: Gary A. Rogers, Laguna Beach, CA (US); Matthew Allan, Anaheim, CA (US); Clayton Harris, Irvine, CA (US); Jianjie Huang, Berkeley, CA (US); Christopher M. Marrs, Foothill Ranch, CA (US); Rudolf Mueller, Foothill Ranch, CA (US); Stanislaw Rachwal, Irvine, CA (US)

(73) Assignee: Cortex Pharmaceuticals, Inc., Irvine, CA (US)

( * ) Notice: Subject to any disclaimer, the term of this patent is extended or adjusted under 35 U.S.C. 154(b) by 447 days.

(21) Appl. No.: 10/495,049

(22) PCT Filed: Nov. 25, 2002

(86) PCT No.: PCT/US02/37646

§ 371 (c)(1),
(2), (4) Date: Aug. 3, 2004

(87) PCT Pub. No.: WO03/045315

PCT Pub. Date: Jun. 5, 2003

(65) Prior Publication Data

US 2004/0259871 A1    Dec. 23, 2004

Related U.S. Application Data

(60) Provisional application No. 60/333,334, filed on Nov. 26, 2001.

(51) Int. Cl.
| C07D 265/12 | (2006.01) |
| C07D 265/14 | (2006.01) |
| C07D 491/04 | (2006.01) |
| C07D 498/04 | (2006.01) |
| C07D 513/04 | (2006.01) |
| C07D 515/04 | (2006.01) |
| A61K 31/536 | (2006.01) |
| A61K 31/5365 | (2006.01) |
| A61P 25/18 | (2006.01) |

(52) U.S. Cl. ............... 544/89; 544/92; 544/95; 514/230.5; 514/229.8; 514/229.5

(58) Field of Classification Search .......... 544/89, 544/92, 95; 514/228.8, 230.5, 228.6, 229.8, 514/229.5

See application file for complete search history.

(56) References Cited

U.S. PATENT DOCUMENTS

| 2,943,087 | A * | 6/1960 | Ohnacker et al. ........... 544/92 |
| 4,022,139 | A | 5/1977 | Reisner et al. |
| 4,268,510 | A * | 5/1981 | Boyle et al. ............. 514/230.5 |
| 5,650,409 | A | 7/1997 | Rogers et al. |
| 5,736,543 | A | 4/1998 | Rogers et al. |
| 5,747,492 | A | 5/1998 | Lynch et al. |
| 5,783,587 | A | 7/1998 | Rogers et al. |
| 5,962,447 | A | 10/1999 | Rogers et al. |
| 6,124,278 | A | 9/2000 | Rogers et al. |

FOREIGN PATENT DOCUMENTS

| DE | 1122531 | * | 1/1962 |
| WO | WO9402475 | | 2/1994 |
| WO | WO 99/16758 | * | 4/1999 |
| WO | WO 99/42456 | | 8/1999 |
| WO | WO 99/51240 | | 10/1999 |

OTHER PUBLICATIONS

Yamamoto, S. et al. "Synthesis and Biological Activity of Novel 1,3-Benzoxazine Derivatiive as K+ Channel Openers" *Chemical and Pharmaceutical bulletin* (Japan) 44(4):734-745, 1996.
Schultz, AG et al. "Enantioselection in the Birch Reduction-Alkylation of a Chiral Benzoic Acid Derivative" *Tetrahedron Letters* 25(41):4591-4594, 1984.
Monaghan et al., Brain Research 324:160-164 (1984).
Arai and Lynch, Brain Research 598:173-184 (1992).
Granger et al., Synapse 15;326-329 (1993).
Staubli et al., PNAS 91:777-781 (1994).
Arai et al., Brain Res. 638:343-346 (1994).
Staubli et al., PNAS 91:11158-11162 (1994).
Shors et al., Neurosci Let. 186:153-156 (1995).
Larson et al., J. Neurosci 15:8023-8030 (1995).
Granger et al., Synapse 22:332-337 (1996).
Arai et al., JPET 278:627-638 (1996).
Lynch et al., Internat. Clin. Psychopharm. 11:13-19 (1996).
Lynch et al., Exp. Neurology 145:89-92 (1997).
Ingvar et al., Exp. Neurology 146:553-559 (1997).
Hampson et al., J. Neurosci. 18:2748-2763 (1998).
Del Cerro and Lynch, Neuroscience 49:1-6 (1992).
Ito et al., J. Physiol. 424:533-543 (1990).
Staubli et al. Psychobiology 18:377-381 (1990).
Xiao et al., Hippocampus 1:373-380 (1991).
Guenzi and Zanetti, J. Chromatogr. 530:397-406 (1990).
Kessler et al., Brain Res. 560:337-341 (1991).
Muller et al., Science 242:1694 (1988).
Tang et al., Science 254:288 (1991).

(Continued)

*Primary Examiner*—Venkataraman Balasubramanian
(74) *Attorney, Agent, or Firm*—Henry D. Coleman; R. Neil Sudol; William J. Sapone

(57) ABSTRACT

This invention related to the prevention and treatment of cerebral insufficiency, including enhancement of receptor functioning in synapses in brain networks responsible for higher order behaviors. These brain networks are involved in cognitive abilities related to memory impairment, such as is observed In a variety of dementias, and in imbalances in neuronal activity between different brain regions, as is suggested in disorders such as Parkinson's disease, schizophrenia and affective disorders. In a particular aspect, the present invention relates to compounds useful for treatment of such conditions and methods of using these compounds for such treatment.

47 Claims, 1 Drawing Sheet

OTHER PUBLICATIONS

Staubli et al., Hippocampus 2:4958 (1992).
Servio et al., Neuroscience 74:1025-1035 (1996). Chapter 7, Neuroscience edited by Dale Purves, Sinauer Associates, Inc. Sunderland, MA 1997.
Diagnostic and Statistical Manual of Mental Disorders, Fourth Edition (DSM IV), pp. 317-391, Sections 293.81; 293.82; 295,10;295.20;295.30;295.60;295.70;295.90;297.1;297.3;298.9.

* cited by examiner

CARBONYLBENZOXAZINE COMPOUNDS FOR ENHANCING GLUTAMATERGIC SYNAPTIC RESPONSES

FIELD OF THE INVENTION

This invention relates to compounds, pharmaceutical compositions and methods for use in the prevention and treatment of cerebral insufficiency, including enhancement of receptor functioning at synapses in brain networks responsible for higher order behaviors. These brain networks, which are involved in cognitive abilities, are related to memory impairment, such as is observed in a variety of dementias, and in imbalances in neuronal activity between different brain regions, as is suggested in disorders such as Parkinson's disease, schizophrenia and affective or mood disorders. In a particular aspect, the present invention relates to compounds useful for treatment of such conditions, and methods of using these compounds for such treatment.

BACKGROUND OF THE INVENTION

The release of glutamate at synapses at many sites in mammalian forebrain stimulates two classes of postsynaptic, ionotropic receptors. These classes are usually referred to as AMPA/quisqualate and N-methyl-D-aspartic acid (NMDA) receptors. AMPA/quisqualate receptors mediate a voltage independent fast excitatory post-synaptic current (the fast EPSC), whereas NMDA receptors generate a voltage-dependent, slow excitatory current. Studies carried out in slices of hippocampus or cortex indicate that the AMPA receptor mediated fast EPSC is generally the dominant component by far at most glutamatergic synapses.

AMPA receptors are not evenly distributed across the brain but rather are largely restricted to the telencephalon and cerebellum. These receptors are found in high concentrations in the superficial layers of neocortex, in each of the major synaptic zones of hippocampus, and in the striatal complex, as reported by Monaghan et al., in *Brain Research* 324:160-164 (1984). Studies in animals and humans indicate that these strictures organize complex perceptual-motor processes and provide the substrates for higher-order behaviors. Thus, AMPA receptors mediate transmission in those brain networks responsible for a host of cognitive activities.

For the reasons set forth above, drugs that modulate and thereby enhance the functioning of AMPA receptors could have significant benefits for cognitive and intellectual performance. Such drugs should also facilitate memory encoding. Experimental studies, such as those reported by Arai and Lynch, *Brain Research* 598:173-184 (1992), indicate that increasing the size of AMPA receptor-mediated synaptic response(s) enhances the induction of long-term potentiation (LTP). LTP is a stable increase in the strength of synaptic contacts that follows repetitive physiological activity of a type known to occur in the brain during learning.

Compounds that enhance the functioning of the AMPA form of glutamate receptors facilitate the induction of LTP and the acquisition of learned tasks as measured by a number of paradigms. See, for example, Granger et al., *Synapse* 15:326-329 (1993); Staubli et al., *PNAS* 91:777-781 (1994); Arai et al., Brain Res. 638:343-346 (1994); Staubli et al., *PNAS* 91:11158-11162 (1994); Shors et al., *Neurosci. Let.* 186:153-156 (1995); Larson et al., *J. Neurosci.* 15:8023-8030 (1995); Granger et al., *Synapse* 22:332-337 (1996); Arai et al., *JPET* 278:627-638 (1996); Lynch et al., *Internal. Clin. Psychopharm.* 11: 13-19 (1996); Lynch et al., *Exp. Neurology* 145:89-92 (1997); Ingvar et al., *Exp. Neurology* 146:553-559 (1997); Hampson, et al., *J. Neurosci.* 18:2748-2763 (1998); and Lynch and Rogers, U.S. Pat. No. 5,747,492. There is a considerable body of evidence showing that LTP is a substrate of memory. For example, compounds that block LTP interfere with memory formation in animals, and certain drugs that disrupt learning in humans antagonize the stabilization of LTP, as reported by del Cerro and Lynch, *Neuroscience* 49: 1-6 (1992).

A prototype for a compound that increases AMPA receptor function was described by Ito et al, *J. Physiol.* 424:533-543 (1990). These authors found that the nootropic drug aniracetam (N-anisoyl-2-pyrrolidinone) increases currents mediated by brain AMPA receptors expressed in Xenopus oocytes without affecting responses by γ-aminobutyric acid (GABA), kainic acid (KA), or NMDA receptors. Infusion of aniracetam into slices of hippocampus was also shown to substantially increase the size of fast synaptic potentials without altering resting membrane properties. It has since been confirmed that aniracetam enhances synaptic responses at several sites in hippocampus, and that it has no effect on NMDA-receptor mediated potentials (Staubli et al., *Psychobiology* 18:377-381 (1990) and Xiao et al., *Hippocampus* 1:373-380 (1991)).

Aniracetam has been found to have an extremely rapid onset and washout, and can be applied repeatedly with no apparent lasting effects, which are desirable features for behaviorally-relevant drugs. Aniracetam does present several disadvantages, however. The peripheral administration of aniracetam is not likely to influence brain receptors. The drug works only at high concentrations (approx. 1000 μM), and about 80% of the drug is converted to anisoyl-GABA following peripheral administration in humans (Guenzi and Zanetti, *J. Chromatogr.* 530:397-406 (1990)). The metabolite, anisoyl-GABA, has been found to have less synaptic activity than aniracetam.

A class of AMPA receptor-modulating compounds that does not display the low potency and inherent instability characteristic of aniracetam has been described (Lynch and Rogers, U.S. Pat. No. 5,747,492). These compounds, termed "Ampakines"®, can be substituted benzamides, which include, for example, 1-(quinoxaline-6-ylcarbonyl)piperidine (CX516; Ampalex®). Typically, they are chemically more stable than aniracetam and show improved bioavailability. CX516 is active in animal tests used to detect efficacious drugs for the treatment of memory disorders, schizophrenia, and depression. In three separate clinical trials, CX516 showed evidence for efficacy in improving various forms of human memory (Lynch et al., *Internat. Clin. Psychopharm.* 11: 13-19 (1996); Lynch et al., *Exp. Neurology* 145:89-92 (1997); Ingvar et al., *Exp. Neurology* 146:553-559 (1997)).

Another class of Ampakines, benzoxazines, has been discovered to have very high activity in in vitro and in vivo models for assessing the probability of producing cognition enhancement (Rogers and Lynch; U.S. Pat. No. 5,736,543). The substituted benzoxazines are rigid benzamide analogues with different receptor modulating properties from the flexible benzamide, CX516.

Certain substituted benzofurazan and benzothiadiazole compounds have been found to be significantly and surprisingly more potent in the animal model of schizophrenia than previous compounds, and are also effective in cognition enhancement. These compounds are structurally similar to those disclosed in Lynch and Rogers, U.S. Pat. No. 5,736,543.

Previously disclosed structures that contained the 1,3-benzoxazine-4-one pharmacophore were substituted on the benzene portion by heteroatoms, such as nitrogen or oxygen (U.S. Pat. Nos. 5,736,543 and 5,962,447), by substituted alkyl groups (U.S. Pat. Nos. 5,650,409 and 5,783,587), or unsubstituted (WO 99/42456). Yet another class of 1,3-benzoxazine compounds contained a carbonyl external to the oxazine ring (U.S. Pat. No. 6,124,278), but not as a substituent on the benzene ring structure. Now, a new class of carbonyl-substituted benzoxazine compounds has been discovered that displays significant activity on hippocampal synaptic responses and neuronal whole cell currents mediated by AMPA receptors and in animal models of cognition and memory. Carbonyl-substituted 1,3-benzoxazine-4-one structures are the first molecules shown to be active as AMPA receptor modulators that have two heavy atoms branching from the same atom alpha to the benzene ring at the 6- or 7-position.

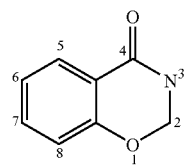

The biological activity of the 6- or 7-carbonyl-substituted 1,3-benzoxazines was unexpected and the potency at the AMPA receptor was surprisingly high; the most potent 1,3-benzoxazines are members of this class of compounds. These compounds are disclosed herein.

SUMMARY OF THE INVENTION

The present invention includes, in one aspect, a compound as shown by structure I, and described in Section II of the Detailed Description, which follows. Administration of compounds of this class has been found to increase synaptic responses mediated by AMPA receptors. The compounds of the present invention are significantly and unexpectedly more potent than previously described compounds in increasing AMPA receptor function in primary neuronal cultures and in slices of rat hippocampus, and in enhancing cognitive performance, such as performance in an 8-arm radial maze. This unexpected activity translates into pharmaceutical compounds and corresponding methods of use, including treatment methods, which utilize significantly lower concentrations (on a mole-to-mole basis) of the present compounds compared to prior art compositions.

The ability of the compounds of the invention to increase AMPA receptor-mediated responses makes the compounds useful for a variety of purposes. These include facilitating the learning of behaviors dependent upon glutamate receptors, treating conditions in which AMPA receptors or synapses utilizing these receptors are reduced in numbers or efficiency, and enhancing excitatory synaptic activity in order to restore an imbalance between brain subregions or increase the levels of neurotrophic factors.

In another aspect, the invention includes a method for the treatment of a mammalian subject suffering from a hypoglutamatergic condition, or from a deficiency in the number or strength of excitatory synapses, or in the number of AMPA receptors, such that memory or other cognitive functions are impaired. Such conditions may also cause a cortical/striatal imbalance, leading to schizophrenia or schizophreniform behavior. According to the method, such a subject is treated with an effective amount of a compound as shown by structure I, and described in Section II of the Detailed Description, following, in a pharmaceutically acceptable carrier.

These and other objects and features of the invention will become more fully apparent when the following detailed description of the invention is read in conjunction with the accompanying drawings.

DETAILED DESCRIPTION OF THE INVENTION

I. Definitions

Figure 1:
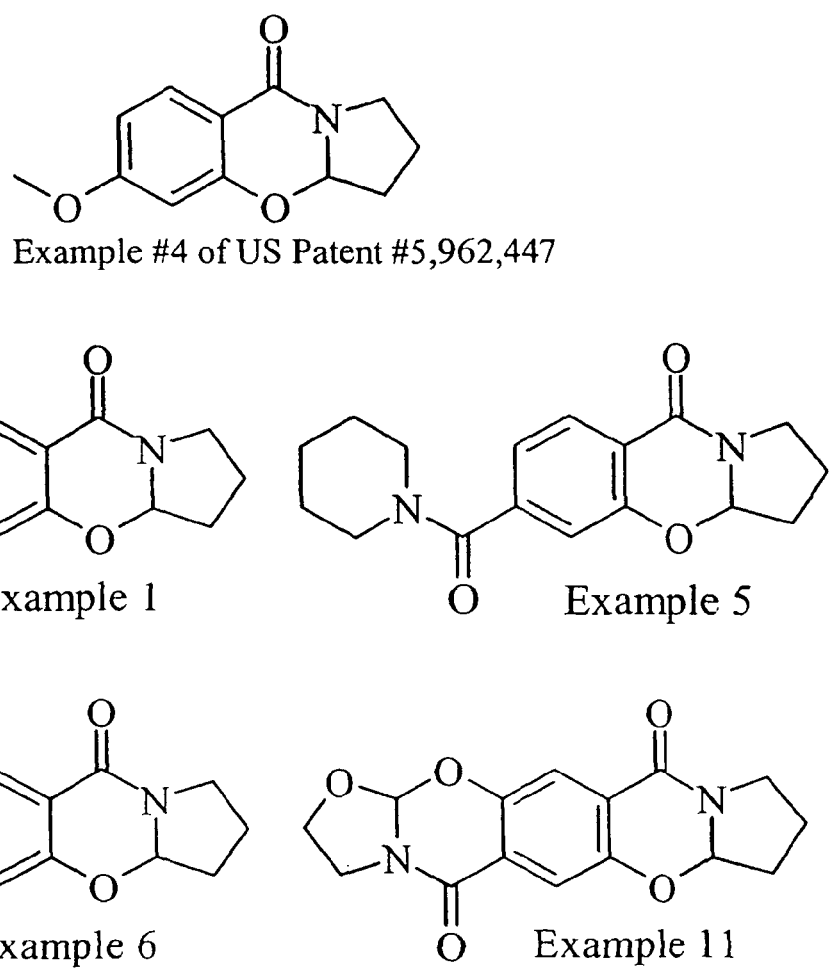
FIG. 1 depicts four compounds of the present invention, along with one compound from the prior art, which were assayed for activity and are described in the experimental section and in Tables 1 and 2, infra.

The terms below have the following definitions unless indicated otherwise. Other terms that are used to describe the present invention have the same definitions as those terms are generally used by those skilled in the art.

The term "alkyl" is used herein to refer to a fully saturated monovalent radical containing carbon and hydrogen, and which may be a straight chain, branched or cyclic. Examples of alkyl groups are methyl, ethyl, n-butyl, n-heptyl, isopropyl, 2-methylpropyl, cyclopropyl, cyclopropylmethyl, cyclobutyl, cyclopentyl, cyclopentylethyl and cyclohexyl.

The term "substituted alkyl" refers to alkyl as just described including one or more functional groups such as lower alkyl containing 1-6 carbon atoms, aryl, substituted aryl, acyl, halogen (i.e., alkyl halos, e.g., $CF_3$), hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like.

The term "aryl" refers to a substituted or unsubstituted monovalent aromatic radical having a single ring (e.g., phenyl) or multiple condensed rings (e.g., naphthyl). Other examples include heterocyclic aromatic ring groups having one or more nitrogen, oxygen, or sulfur atoms in the ring, such as imidazolyl, furyl, pyrrolyl, pyridyl, thienyl and indolyl.

The term "substituted aryl" refers to an aryl as just described that contains one or more functional groups such as lower alkyl, acyl, aryl, halogen, alkylhalos (e.g., $CF_3$), hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like.

"Heterocycle" or "heterocyclic" refers to a carbocylic ring wherein one or more carbon atoms have been replaced with one or more heteroatoms such as nitrogen, oxygen or sulfur. Examples of heterocycles include, but are not limited to, piperidine, pyrrolidine, morpholine, thiomorpholine, piperazine, tetrahydrofuran, tetrahydropyran, 2-pyrrolidinone, δ-velerolactam, δ-velerolactone and 2-ketopiperazine.

The term "substituted heterocycle" refers to a heterocycle as just described that contains one or more functional groups such as lower alkyl, acyl, aryl, cyano, halogen, hydroxy, alkoxy, alkoxyalkyl, amino, alkyl and dialkyl amino, acylamino, acyloxy, aryloxy, aryloxyalkyl, carboxyalkyl, carboxamido, thio, thioethers, both saturated and unsaturated cyclic hydrocarbons, heterocycles and the like.

The term "compound" is used herein to refer to any specific chemical compound disclosed herein. Within its use in context, the term generally refers to a single compound, but in certain instances may also refer to stereoisomers and/or optical isomers (including racemic mixtures) of disclosed compounds.

The term "effective amount" refers to the amount of a selected compound of formula I that is used to enhance glutamatergic synaptic response by increasing AMPA receptor activity. The precise amount used will vary depending upon the particular compound selected and its intended use, the age and weight of the subject, route of administration, and so forth, but may be easily determined by routine experimentation. In the case of the treatment of a condition or disease state, an effective amount is that amount which is used to effectively treat the particular condition or disease state.

The term "pharmaceutically acceptable carrier" refers to a carrier or excipient which is not unacceptably toxic to the subject to which it is administered. Pharmaceutically acceptable excipients are described at length by E. W. Martin, in "Remington's Pharmaceutical Sciences."

A "pharmaceutically acceptable salt" of an amine compound, such as those contemplated in the current invention, is an ammonium salt having as counterion an inorganic anion such as chloride, bromide, iodide, sulfate, sulfite, nitrate, nitrite, phosphate, and the like, or an organic anion such as acetate, malonate, pyruvate, propionate, fumarate, cinnamate, tosylate, and the like.

The term "patient" or "subject" is used throughout the specification to describe an animal, generally a mammalian animal, including a human, to whom treatment or use with the compounds or compositions according to the present invention is provided. For treatment or use with/or of those conditions or disease states which are specific for a specific animal (especially, for example, a human subject or patient), the term patient or subject refers to that particular animal.

The term "sensory motor problems" is used to describe a problem which arises in a patient or subject from the inability to integrate external information derived from the five known senses in such a way as to direct appropriate physical responses involving movement and action.

The term "cognitive task" or "cognitive function" is used to describe an endeavor or process by a patient or subject that involves thought or knowing. The diverse functions of the association cortices of the parietal, temporal and frontal lobes, which account for approximately 75% of all human brain tissue, are responsible for much of the information processing that goes on between sensory input and motor output. The diverse functions of the association cortices are often referred to as cognition, which literally means the process by which we come to know the world. Selectively attending to a particular stimulus, recognizing and identifying these relevant stimulus features and planning and experiencing the response are some of the processes or abilities mediated by the human brain which are related to cognition.

The term "brain network" is used to describe different anatomical regions of the brain that communicate with one another via the synaptic activity of neuronal cells.

The term "AMPA receptor" refers to an aggregate of proteins found in some membranes, which allows positive ions to cross the membrane in response to the binding of glutamate or AMPA (DL-α-amino-3-hydroxy-5-methyl-4-isoxazolepropionic acid), but not NMDA.

The term "excitatory synapse" is used to describe a cell-cell junction at which release of a chemical messenger by one cell causes depolarization of the external membrane of the other cell. An excitatory synapse describes a postsynaptic neuron which has a reversal potential that is more positive than the threshold potential and consequently, in such a synapse, a neurotransmitter increases the probability that an excitatory post synaptic potential will result (a neuron will fire producing an action potential). Reversal potentials and threshold potentials determine postsynaptic excitation and inhibition. If the reversal potential for a post synaptic potential ("PSP") is more positive than the action potential threshold, the effect of a transmitter is excitatory and produces an excitatory post synaptic potential ("EPSP") and the firing of an action potential by the neuron. If the reversal potential for a post synaptic potential is more negative than the action potential threshold, the transmitter is inhibitory and may generate inhibitory post synaptic potentials (IPSP), thus reducing the likelihood that a synapse will fire an action potential. The general rule for postsynaptic action is: if the reversal potential is more positive than threshold, excitation results; inhibition occurs if the reversal potential is more negative than threshold. See, for example, Chapter 7, *NEUROSCIENCE*, edited by Dale Purves, Sinauer Associates, Inc., Sunderland, Mass. 1997.

The term "motor task" is used to describe an endeavor taken by a patient or subject that involves movement or action.

The term "perceptual task" is used to describe an act by a patient or subject of devoting attention to sensory inputs.

The term "synaptic response" is used to describe biophysical reactions in one cell as a consequence of the release of chemical messengers by another cell with which it is in close contact.

The term "hypoglutamatergic condition" is used to describe a state or condition in which transmission mediated by glutamate (or related excitatory amino acids) is reduced to below normal levels. Transmission consists of the release of glutamate, binding to post synaptic receptors, and the opening of channels integral to those receptors. The end point of the hypoglutamatergic condition is reduced excitatory post synaptic current. It can arise from any of the three above noted phases of transmission. Conditions or disease states which are considered hypoglutamatergic conditions and which can be treated using the compounds, compositions and methods according to the present invention include, for example, loss of memory, dementia, depression, attention disorders, sexual dysfunction, movement disorders, including Parkinson's disease, schizophrenia or schizophreniform behavior, memory and learning disorders, including those disorders which result from aging, trauma, stroke and neurodegenerative disorders, such as those associated with drug-induced states, neurotoxic agents, Alzheimer's disease, and aging. These conditions are readily recognized and diagnosed by those of ordinary skill in the art.

The term "cortico-striatal imbalance" is used to describe a state in which the balance of neuronal activities in the interconnected cortex and underlying striatal complex deviates from that normally found. 'Activity' can be assessed by electrical recording or molecular biological techniques. Imbalance can be established by applying these measures to the two structures or by functional (behavioral or physiological) criteria.

The term "affective disorder" or "mood disorder" describes the condition when sadness or elation is overly intense and continues beyond the expected impact of a stressful life event, or arises endogenously. As used herein, the term "effective disorder" embraces all types of mood disorders as described in, for example, *Diagnostic and Statistical Manual of Mental Disorders*, Fourth Edition (DSM IV), pages 317-391.

The term "schizophrenia" is used to describe a condition which is a common type of psychosis, characterized by a disorder in the thinking processes, such as delusions and hallucinations, and extensive withdrawal of the individual's interest from other people and the outside world, and the investment of it in his or her own. Schizophrenia is now considered a group of mental disorders rather than a single entity, and distinction is made between reactive and process schizophrenias. As used herein, the term schizophrenia or "schizophreniform" embraces all types of schizophrenia, including ambulatory schizophrenia, catatonic schizophrenia, hebephrenic schizophrenia, latent schizophrenia, process schizophrenia, pseudoneurotic schizophrenia, reactive schizophrenia, simple schizophrenia, and related psychotic disorders which are similar to schizophrenia, but which are not necessarily diagnosed as schizophrenia per se. Schizophrenia and other psychotic disorders may be diagnosed using guidelines established in, for example, *Diagnostic and Statistical Manual of Mental Disorders*, Fourth Edition (DSM IV) Sections 293.81, 293.82, 295.10, 295.20, 295.30, 295.40, 295.60, 295.70, 295.90, 297.1, 297.3, 298.8.

The term "brain function" is used to describe the combined tasks of perceiving, integrating, filtering and responding to external stimuli and internal motivational processes.

The term "impaired" is used to describe a function working at a level that is less than normal. Impaired functions can be significantly impacted such that a function is barely being carried out, is virtually non-existent or is working in a fashion that is significantly less than normal. Impaired functions may also be sub-optimal. The impairment of function will vary in severity from patient to patient and the condition to be treated.

II. Compounds that Increase AMPA Receptor Function

The present invention is directed, in one aspect, to compounds having the property of enhancing AMPA receptor function. These are compounds having the structure Ia or Ib, below:

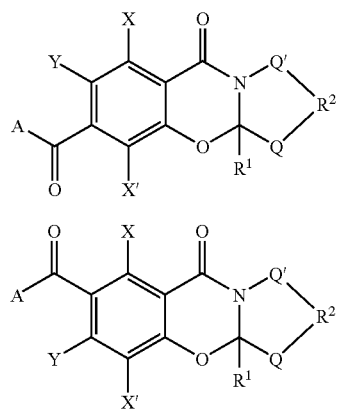

in which:
Q and Q' are independently hydrogen, —CH$_2$—, —O—, —S—, alkyl, or substituted alkyl,
R$^1$ is hydrogen, alkyl or together with Q may be a cycloalkyl ring,
R$^2$ may be absent, or if present may be —CH$_2$—, —CO—, —CH$_2$CH$_2$—, —CH$_2$CO—, —CH$_2$O—, —CRR'—, or —CONR—,
Y is hydrogen or —OR$^3$, or serves to link the aromatic ring to A as a single bond =N— or —NR—,
R$^3$ is hydrogen, alkyl, substituted alkyl, or serves to link the attached oxygen to A by being a lower alkylene such as a methylene or ethylene, or substituted lower alkylene such as —CRR'— linking the aromatic ring to A to form a substituted or unsubstituted 6, 7 or 8-membered ring, or a bond linking the oxygen to A in order to form a 5- or 6-membered ring, A is —NRR', —OR, alkyl, substituted alkyl, cycloalkyl, substituted cycloalkyl, cycloalkylalkyl, aryl, substituted aryl, a heterocycle or a substituted heterocycle containing one or two heteroatoms such as oxygen, nitrogen or sulfur, R is hydrogen, aryl, arylalkyl, substituted aryl, substituted arylalkyl, alkyl, substituted alkyl, cycloalkyl, substituted cycloalkyl, or heterocycloalkyl, R' is absent or hydrogen, aryl, arylalkyl, substituted aryl, substituted arylalkyl, alkyl, substituted alkyl, cycloalkyl, substituted cycloalkyl or may join together with R to form a 4- to 8-membered ring, which may be substituted by X and may be linked to Y to form a 6-membered ring and which may optionally contain one or two heteroatoms such as oxygen, nitrogen or sulfur, X and X' are independently R, halo, —CO$_2$R, —CN, —NRR', —NRCOR', —NO$_2$, —N$_3$ or —OR.

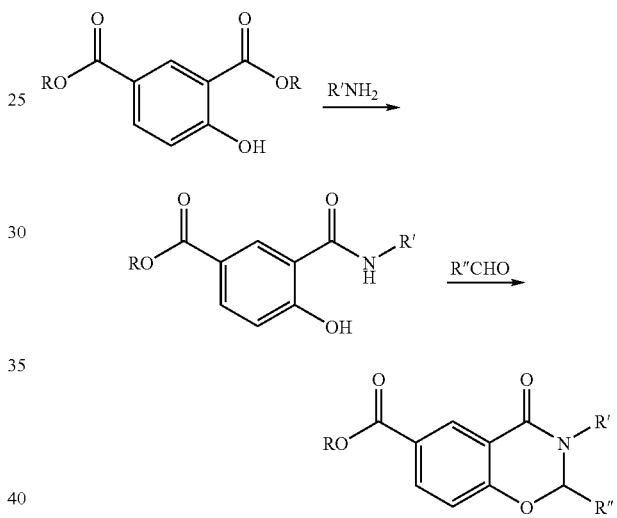

The synthesis of 1,3-benzoxazin-4-one structures substituted with carbonyl moieties at the 6- or 7-position are preferably carried out by the following routes. 1) 6-carbonyl substituted 1,3-benzoxazin-4-one structures may be synthesized by the trialkylaluminum-assisted selective aminolysis of esters of 4-hydroxyisophthalate, followed by ring closure using an aldehyde. Further reactions, known to those skilled in the art, may be carried on the ester remaining in the 6-position in order to transform the ester into a variety of other carbonyl containing, but not limited to moieties such as amides, aldehydes, ketones, oximes, or other esters.

In like manner, 7-carbonyl substituted 1,3-benzoxazin-4-one structures may be synthesized by an unassisted direct aminolysis of esters of 2-hydroxyterephthalate followed by reaction with an aldehyde as illustrated. Conversion of the unreacted ester to other carbonyl containing moieties as described for the 6-position above is within the scope of the invention. All compositions disclosed in the present application may be synthesized by the above-described method using analogous synthetic steps to these specifically presented in the examples described herein as well as those known in the art. Isolation of stereo- and/or optical isomers may be performed by methods which are well known in the art.

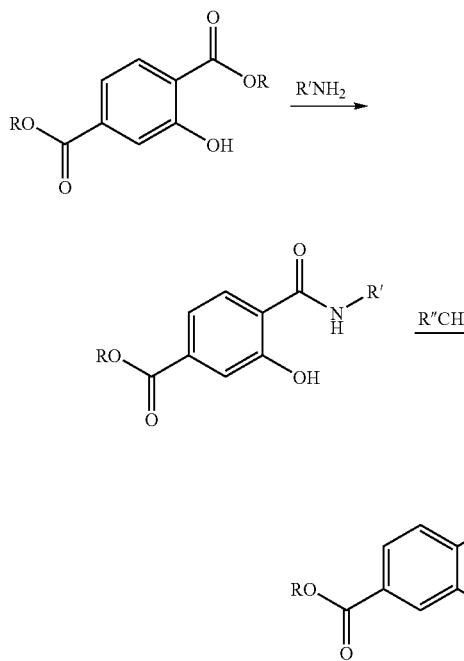

III. Method of Treatment

According to one aspect of the invention, a method is provided for treating a mammalian subject suffering from a hypoglutamatergic condition, or from deficiencies in the number or strength of excitatory synapses or in the number of AMPA receptors. In such a subject, memory or other cognitive functions may be impaired, or cortical/striatal imbalance may occur, leading to loss of memory, dementia, depression, attention disorders, sexual dysfunction, movement disorders, schizophrenia or schizophreniform behavior. Memory disorders and learning disorders, which are treatable according to the present, invention include those disorders that result from aging, trauma, stroke and neurodegenerative disorders. Examples of neurodegenerative disorders include, but are not limited to, those associated with drug-induced states, neurotoxic agents, Alzheimer's disease, and aging. These conditions are readily recognized and diagnosed by those of ordinary skill in the art and treated by administering to the patient an effective amount of one or more compounds according to the present invention.

In the present invention, the method of treatment comprises administering to the subject in need of treatment, in a pharmaceutically acceptable carrier, an effective amount of a compound having the formula:

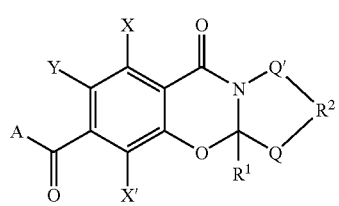

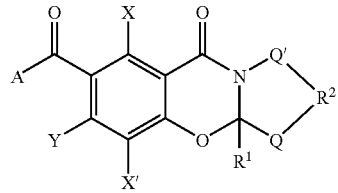

wherein

Q and Q' are independently hydrogen, —$CH_2$—, —O—, —S—, alkyl, or substituted alkyl, $R^1$ is hydrogen, alkyl or together with Q may be a cycloalkyl ring, $R^2$ may be absent, or if present may be —$CH_2$—, —CO—, —$CH_2CH_2$—, —$CH_2CO$—, —$CH_2O$—, —CRR'—, or —CONR—, Y is hydrogen or —$OR^3$, or serves to link the aromatic ring to A as a single bond, =N— or —NR—, $R^3$ is hydrogen, alkyl, substituted alkyl, or lower alkylene such as a methylene or ethylene, or substituted lower alkylene such as —CRR'— linking the aromatic ring to A to form a substituted or unsubstituted 5, 6 or 7-membered ring, or a bond linking the aromatic ring to A in order to form a 5- or 6-membered ring, A is —NRR', —OR, alkyl, substituted alkyl, cycloalkyl, substituted cycloalkyl, cycloalkylalkyl, aryl, substituted aryl, a heterocycle or a substituted heterocycle containing one or two heteroatoms such as oxygen, nitrogen or sulfur;

R is hydrogen, aryl, arylalkyl, substituted aryl, substituted arylalkyl, alkyl, substituted alkyl, cycloalkyl, substituted cycloalkyl, or heterocycloalkyl, R' is hydrogen, aryl, arylalkyl, substituted aryl, substituted arylalkyl, alkyl, substituted alkyl, cycloalkyl, substituted cycloalkyl or may join together with R to form a 4- to 8-membered ring, which may be substituted by R or X or linked to Y by $R^3$ and which may optionally contain one or two heteroatoms such as oxygen, nitrogen or sulfur, X and X' are independently R, halo, —$CO_2R$, —NRR', —NRCOR', —$NO_2$, —$N_3$ or —OR.

As noted above, treatment of a subject according to the method of the invention is useful for enhancing AMPA receptor activity, and thus may be used to facilitate the learning of behaviors dependent upon AMPA receptors, and to treat conditions, such as memory impairment, in which AMPA receptors, or synapses utilizing these receptors, are reduced in numbers or efficiency. The method is also useful for enhancing excitatory synaptic activity in order to restore an imbalance between brain subregions, which may manifest itself in schizophrenia or schizophreniform behavior, or other behavior as described above. The compounds administered in accordance with the method have been found to be more effective than previously described compounds in enhancing AMPA receptor activity, as shown in the in vitro and in vivo tests described below.

IV. Biological Activity

A. Enhancement of AMPA Receptor Function

Synaptic responses mediated by AMPA receptors are increased according to the method of the invention, using the compounds described herein. These compounds are demonstrated, in the Examples that follow, to be substantially more potent than previously-described compounds in increasing AMPA mediated whole cell currents in cultured neurons and AMPA receptor function in slices of rat hippocampus. These in vitro assays are described as follows, and in Example 64 below.

The field EPSP, (excitatory post-synaptic potential) recorded in field CA1 after stimulation of CA3 axons is known to be mediated by AMPA receptors, which are present in the synapses (Kessler et al., *Brain Res.* 560: 337-341 (1991)). Drugs that selectively block the receptor selectively block the field EPSP (Muller et al., *Science*, supra). Aniracetam, which has been shown to increase the mean open time of the AMPA receptor channel, increases the amplitude of the synaptic current and prolongs its duration (Tang et al., *Science*, supra). These effects are mirrored in the field EPSP (see, for example, Staubli et al., *Psychobiology*, supra; Xiao et al., *Hippocampus*, supra; Staubli et al., *Hippocampus* 2: 4958 (1992)). Similar results have been reported for the previously disclosed stable benzamide analogs of aniracetam (Lynch and Rogers, PCT Pubn. No. WO 94/02475).

To obtain the data shown in Table I, a bipolar nichrome stimulating electrode was positioned in the dendritic layer (stratum radiatum) of the hippocampal subfield CA1 close to the border of subfield CA3, as described in Example 64. Current pulses (0.1 msec) through the stimulating electrode activate a population of the Schaffer-commissural (SC) fibers, which arise from neurons in the subdivision CA3 and terminate in synapses on the dendrites of CA1 neurons. Activation of these synapses causes them to release the transmitter glutamate. Glutamate binds to post-synaptic AMPA receptors, which then transiently open an associated ion channel and permit a sodium current to enter the postsynaptic cell. This current results in a voltage in the extracellular space (the field EPSP), which is recorded by a high impedance recording electrode positioned in the middle of the stratum radiatum of CA1.

The intensity of the stimulation current was adjusted to produce half-maximal EPSPs (typically about 1.5-2.0 mV). Paired stimulation pulses were given every 40 sec with an interpulse interval of 200 msec, as described further in Example 64.

Hippocampal slices were maintained in a recording chamber continuously perfused with artificial cerebrospinal fluid (ACSF). During 15-30 minute intervals, the perfusion medium was switched to one containing various concentrations of the test compounds. Responses collected immediately before and at the end of drug perfusion were superimposed in order to calculate the percent increase in EPSP amplitude.

Invention compound 1A (the most active isomer of product of Example 1, as shown in FIG. 1), and reference compound CX516, disclosed in U.S. Pat. No. 5,747,492, were assayed in the physiological test system described above. The first data column of Table 1, below, shows the estimate of the concentration of each test compound that would be required to increase the amplitude of the field EPSP to a value 10% above the baseline level.

TABLE 1

| Compound # | Amp[1] ($\mu$M) | $EC_{2x}$[2] ($\mu$M) | $MED_C$[3] (mg/kg) |
|---|---|---|---|
| CX516* | 80 | 830 | 12.5 |
| Example 1A | 0.3 | 0.12 | 0.05[†] |

*Example # XIII of U.S. Pat. No. 5,747,492
[1]Concentration of compound that causes a 10% increase in the amplitude of the field EPSP in field CA 1 of rat hippocampal slice
[2]Concentration of compound that causes at least a doubling of the steady-state current induced in cortical neurons in primary culture by 300 $\mu$M glutamate.
[3]Minimum Effective Dose that produces a statistically significant improvement in behavior in the eight-arm radial maze task for cognition/memory enhancement.
[†]The unresolved product of Example 1 was used for this test.
ND = Not determined As the data in Table 1 show, the present invention compound produced an increase in the amplitude of the fEPSP in hippocampus and was effective at concentrations as low as 0.3 $\mu$M. The potency of the present compound on AMPA receptor mediated cell currents was also assessed in primary neuronal culture, wherein concentrations as low as 0.12 $\mu$M caused a doubling of the steady-state current in cultured neurons generated by 500 $\mu$M glutamate. The majority of the tested compounds were equally or more effective than the reference compounds, CX516 and the heteroatom substituted benzoxazine CX559, in increasing AMPA receptor function as shown in Table 2.

TABLE 2

| EXAMPLE | AMP[1] ($\mu$M) | $EC_{2x}$[2] ($\mu$M) |
|---|---|---|
| CX516* | 80 | 830 |
| CX559** | 300 | >10 |
| 1A[†] | 0.3 | 0.12 |
| 1B[††] | 30 | >10 |
| 2 | >10 | 2.6 |
| 5 | 10 | 2 |
| 6 | 100 | 1.4 |
| 11 | 1 | 0.09 |
| 18 | 100 | 4 |
| 21 | 10 | 1.8 |
| 22 | 10 | 0.2 |
| 27 | 10 | 1 |
| 28 | 10 | 6 |
| 38 | 30 | 15 |
| 46 | 3 | 2.4 |

[1]The concentration of modulator that increases the amplitude of the fEPSP by 10%
[2]The concentration of modulator required to double the steady state current induced by 300 $\mu$M glutamate on cultured neurons
*Example # XIII of U.S. Pat. No. 5,747,492
**Example # 4 of U.S. Pat. No. 5,962,447 (shown in FIG. 1)
[†]More active enantiomer of Example 1
[††]Less active enantiomer of Example 1

Studies that compared the effects of AMPA modulators on monosynaptic (as reported here) and polysynaptic responses demonstrated that a 10% increase in the amplitude of the monosynaptic field EPSP was amplified to an increase of 300% on a trisynaptic response (Servio et al., *Neuroscience* 74: 1025-1035 (1996)). Furthermore, the concentration of the modulator that evoked these responses was shown to exist in plasma from behaviorally relevant doses (Granger et al., *Synapse*, supra). Thus, the concentration of compound sufficient to produce a 10% increase in amplitude of the monosynaptic field EPSP, as reported in Table 1 and Table 2, is likely to represent a behaviorally relevant plasma concentration.

B. Behavioral Testing

The compounds of the invention are also effective in relevant animal behavioral tasks that have been shown to correlate with efficacy in the treatment of a variety of diseases, such as schizophrenia, and in models of cognitive performance, such as performance in an 8-arm radial maze.

The third data column shows the MED for efficacy to improve performance in the eight-arm radial maze task, which tests for improved memory and cognition ($MED_C$). This task has been described previously (Staubli et al., *PNAS* 91:777-781 (1994)) and Lynch and Rogers, PCT Pubn. No. WO 94/02475). The compound of Example 1 was 250-times more potent than CX516 in this test.

V. Administration, Dosages, and Formulation

As noted above, the compounds and method of the invention increase AMPA receptor-mediated responses, and are useful for the treatment of hypoglutamatergic conditions. They are also useful for treatment of conditions such as impairment of memory or other cognitive functions, brought on by a deficiency in the number or strength of excitatory synapses, or in the number of AMPA receptors. They may also be used in the treatment of schizophrenia or schizophreniform behavior resulting from a cortical/striatal imbalance, and in facilitation of learning of behaviors dependent upon AMPA receptors.

In subjects treated with the present compounds, pharmaceutical compositions and methods memory or other cognitive functions may be impaired, or cortical/striatal imbalance may occur, leading to loss of memory, dementia, depression, attention disorders, sexual dysfunction, movement disorders, schizophrenia or schizophreniform behavior. Memory disorders and learning disorders, which are treatable according to the present invention, include those disorders that result from aging, trauma, stroke and neurodegenerative disorders. Examples of neurodegenerative disorders include, but are not limited to, those associated with drug-induced states, neurotoxic agents, Alzheimer's disease, and aging. These conditions are readily recognized and diagnosed by those of ordinary skill in the art and treated by administering to the patient an effective amount of one or more compounds according to the present invention.

Generally, dosages and routes of administration of the compound will be determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, or intramuscular injection, among others, including buccal, rectal and transdermal administration. Subjects contemplated for treatment according to the method of the invention include humans, companion animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. Preferably, the composition will be about 0.5 to 75% by weight of a compound or compounds of the invention, with the remainder consisting essentially of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration will typically contain the compound in a suitable i.v. solution, such as sterile physiological salt solution. The composition may also be formulated as a suspension in a lipid or phospholipid, in a liposomal suspension, or in an aqueous emulsion.

Methods for preparing such dosage forms are known or will be apparent to those skilled in the art; for example, see *Remington's Pharmaceutical Sciences* (17th Ed., Mack Pub. Co, 1985). The composition to be administered will contain a quantity of the selected compound in a pharmaceutically effective amount for effecting increased AMPA receptor currents in a subject.

The following examples illustrate but are not intended in any way to limit the invention. Unless otherwise stated, all temperatures are given in degrees Celsius. Unless otherwise stated, all NMR spectra are $^1$H NMR spectra and were obtained in deuterochloroform or deuterated DMSO as solvent using tetramethylsilane as an internal standard. Infrared (IR) spectra were recorded as thin films on a Fresnel crystal, on NaCl crystals or in a KBr pellet in a ATI Mattson Gemini series FTIR. All names of compounds conform to IUPAC nomenclature as provided by the computer software Chemistry 4-D Draw™ Pro3.0 by ChemInnovation Software, Inc.

EXAMPLE 1

(R,S), (R,S)-3aH,9aH-pyrrolidino[2,1-b]pyrrolidino [2",1"-2',3'](1,3-oxazino)[5',6'-2,1]benzo[4,5-e]1,3-oxazaperhydroine-6,12-dione

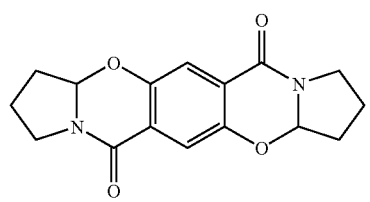

Method A 2,5-Dihydroxyterephthalic acid (3.75 g, 18.9 mmol) was added to a solution of carbonyl diimidazole (6.20 g, 38.2 mmol) in 50 mL anhydrous dimethyl formamide. The solution was allowed to stir at room temperature for 24 h at which time 4-aminobutyraldehyde diethyl acetal (6.30 g, 39.0 mmol) was added. The solution was stirred for an additional 24 h at room temperature, and then heated briefly to 80° C. The solvent was removed by vacuum distillation and the residue was purified by flash chromatography (hexane:ethyl acetate 2:1) on silica gel to yield 4.0 g of the crude bisacetal/amide. The intermediate was dissolved in 125 mL methylene chloride to which 2.0 mL trifluoroacetic acid, 20 mg camphorsulfonic acid and activated 4A molecular sieves were added. The reaction went to completion overnight as judged by tlc. The crude product was chromatographed on silica gel (hexane:ethyl acetate 95:5) to yield 1.9 g of solid, which was dissolved in methylene chloride (250 mL) and filtered. Concentration of the solution to 50 mL followed by dilution with diethyl ether promoted crystallization. The solution was cooled to 0° C. and 1.06 g (19%) white solid was collected by filtration. MP=270-271° C. IR: 2977, 2880, 1667, 1453, 1422, 1335, 1181, 1073, and 780 cm$^{-1}$. $^1$H NMR (500 MHz) δ 7.55 (1H, s) 7.53 (1H, s), 5.47 (2H, m) 3.86 (2H, m), 3.62 (2H, m), 2.44 (2H, m), 2.27 (2H, m), 2.12 (2H, m) and 1.96 ppm (2H, m).

Method B

Diethyl 2,5-dihydroxyterephthalate (500 mg, 1.97 mmol) and 4-aminobutyraldehyde diethyl acetal (≧90%) (1.30 g, ≧7.2 mmol) were combined and heated to reflux for 90 s. The reaction mixture was allowed to cool to ambient and subsequently diluted with 10 mL CH$_2$Cl$_2$. Trifluoroacetic acid (2.0 mL) and 5A molecular sieves were added to the reaction mixture, which was heated briefly to reflux and allowed to stand for 2 h. This mixture was concentrated on silica gel under reduced pressure and eluted with ethyl acetate. The fractions were concentrated under reduced pressure to yield 420 mg (71%) of product as a white solid with physical and spectroscopic characteristics essentially identical to those reported for product derived by Method A, above.

EXAMPLE 2

(R,S), (R,S)-3aH,6aH-pyrrolidino[2,1-b]pyrrolidino[2″,1″-3′,2′](1,3-oxazino)[6′,5′-2,1]benzo[4,5-e]1,3-oxazaperhydroine-10,12-dione

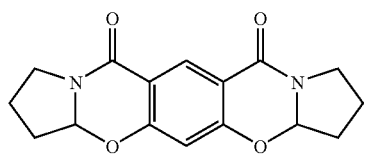

To a heated (40° C.) suspension of 2,4-dihydroxisophthalic acid (500 mg, 2.5 mmol) in a solution of SOCl$_2$ (8.0 mL, 100 mmol) and 2 mL dry CHCl$_3$ was added 3 drops DMF. The reaction mixture was heated for 1.5 h at which time it became transparent. The solution was concentrated under reduced pressure, diluted with CH$_2$Cl$_2$, and re-concentrated under reduced pressure. The residue was dissolved in 10 mL dry CHCl$_3$, to which 4-aminobutyraldehyde diethyl acetal (1.00 g, 6.2 mmol) was added dropwise. After chilling the solution to 0° C., 2.0 mL of triethylamine was added to the mixture, which was allowed to warm to ambient. After 1 h the solution was diluted with CH$_2$Cl$_2$, washed sequentially with 10% HCl, saturated NaHCO$_3$, saturated NaCl, and then dried over Na$_2$SO$_4$. The resulting oil was concentrated under reduced pressure and re-dissolved in 10 mL dry CHCl$_3$, to which was added 30 mg camphorsulfonic acid. The reaction mixture was stirred for 12 h and then concentrated onto silica gel under reduced pressure. Elution with EtOAc/MeOH (99:1) gave 270 mg (36%) of white crystalline powder with the following properties: MP=248-252° C. IR: 1673, 1432, 1356 and 1138 cm$^{-1}$. $^1$H NMR (500 MHz) δ 8.58 (0.5H, s), 8.52 (0.5H, s), 6.51 (1H, m), 5.50 (2H, m) 3.80-3.85 (2H, m), 3.60-3.65 (2H, m), 2.40-2.45 (2H, m), 2.20-2.30 (2H, m), 2.05-2.15 (2H, m) and 1.90-2.00 ppm (2H, m).

EXAMPLE 3

(R,S)-Methyl 9-oxo-3aH-benzo[e]pyrrolidino[2,1-b] 1,3-oxazaperhydroine-6-carboxylate

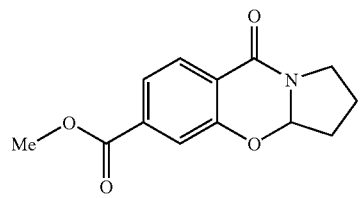

Trimethylaluminum (2.0 mL of 2 M in toluene, 4.0 mmol) was added to a solution of 810 mg dimethyl hydroxyterephthalate (3.85 mmol) in 15 mL dry CHCl$_3$, which was stirred for 20 min. 4-Aminobutyraldehyde diethyl acetal (750 mg, 4.65 mmol) was added and the reaction mixture was heated to reflux for 6 h. Trifluoroacetic acid (2.0 mL) and 5A molecular sieves were added to the cooled solution, which was heated to reflux briefly and allowed to stand for 30 min. The reaction mixture was concentrated onto silica gel under reduced pressure and eluted with hexane/EtOAc (1:1) to (1:1) to provide 387 mg of the title benzoxazine as a white solid with MP=76-78° C. IR: 1725, 1672, 1439, 1291, 1212 and 1088 cm$^{-1}$. $^1$H NMR (200 MHz) δ 8.01 (1H, d, J=8.0 Hz), 7.77 (1H, dd, J=8.0, 1.5 Hz), 7.64 (1H, d, J=1.5 Hz), 5.53 (1H, t, J=5.7 Hz), 3.94 (3H, s), 3.80-3.92 (3H, m) and 1.80-2.60 ppm (3H, m).

EXAMPLE 4

(R,S)-Methyl 9-oxo-3aH-benzo[3,4-e]pyrrolidino[2,1-b]1,3-oxazaperhydroine-7-carboxylate

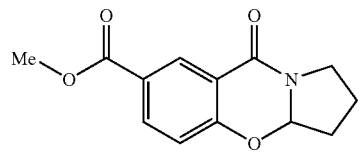

Dimethyl 4-hydroxyisophthalate (1.00 g, 4.8 mmol) and 4-aminobutyraldehyde diethyl acetal (1.60 g, 10 mmol) were combined and heated to reflux for 90 s. The mixture was allowed to cool to ambient and dissolved in 10 mL CHCl$_3$. Trifluoroacetic acid (1.0 mL) and 5A molecular sieves were added to the solution, which was stirred for 2 h. Concentration onto silica gel under reduced pressure and elution with hexane/EtOAc (2:1) yielded 500 mg (42%) white solid with MP=164-166° C. IR: 1711, 1669, 1615, 1445 and 1285 cm$^{-1}$. $^1$H NMR (200 MHz) δ 8.62 (1H, d, J=2.2 Hz), 8.12 (1H, dd, J=8.7 & 2.2 Hz), 7.02 (1H, d, J=8.6 Hz), 5.55 (1H, t, J=5.66 Hz), 3.92 (3H, s), 3.50-3.90 (3H, m) and 1.80-2.60 ppm (3H, m).

EXAMPLE 5

(R,S)-6-(Piperidylcarbonyl)-3aH-benzo[e]pyrrolidino[2,1-b]1,3-oxazaperhydroin-9-one

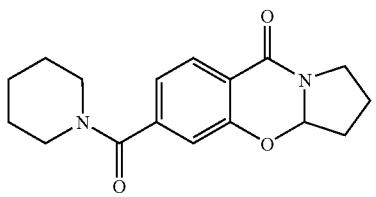

(R,S)-Methyl-9-oxo-3aH-benzo[e]pyrrolidino[2,1-b]1,3-oxazaperhydroine-6-carboxylate (Example 3, above) (387 mg, 1.56 mmol) was dissolved in 10 ml dry $CHCl_3$ to which trimethylaluminum (2.0 mL of 2M in toluene, 4.0 mmol) was added followed by 400 mg piperidine (4.7 mmol). The reaction mixture was heated to reflux for 3 h, cooled to ambient, and quenched with acetic acid. Concentration onto silica gel under reduced pressure and elution with EtOAc/MeOH (99:1) yielded 300 mg of a white crystalline solid with MP=149-151° C. IR: 1670, 1632 and 1440 cm$^{-1}$. $^1$H NMR (200 MHz) δ 7.96 (1H, d, J=7.9 Hz), 7.12 (1H, d, J=7.9 Hz), 7.00 (1H, s), 5.51 (1H, t, J=5.6 Hz), 3.50-4.00 (4H, m), 3.15-3.40 (2H, m), 1.80-2.60 (4H, m) and 1.40-1.60 ppm (6H, m).

EXAMPLE 6

(R,S)-6a-hydro-3aH-pyrrolidino[2,1-b]pyrrolidino[2',1'-2,3]quinazolino[7,6-e]1,3-oxazaperhydroine-6,12-dione

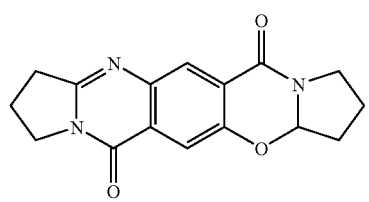

Hydroxyterephthalic acid (4.0 g, 22 mmol) was dissolved in 200 mL THF to which was added an excess of diazomethane in diethyl ether. The reaction mixture was quenched with acetic acid, diluted with $CH_2Cl_2$, concentrated onto silica gel under reduced pressure, and eluted with hexane/EtOAc (4:1) to yield 4.40 g as a waxy solid with MP=69-75° C. IR: 1720, 1678, 1436, 1319, 1212 and 1109 cm$^{-1}$.

Dimethyl hydroxyterephthalate (3.00 g, 14.3 mmol) was cooled to 5° C. and mixed with 7 mL fuming nitric acid for 40 min. The reaction mixture was poured onto ice and extracted with ethyl acetate. The organic layer was washed with pH 7 phosphate buffer, saturated NaCl, and dried over anhydrous $Na_2SO_4$. The solvent was removed under reduced pressure to yield crude 3.0 g dimethyl-2-hydroxy-4-nitroterephthalate. IR: 1739, 1688, 1549, 1442, 1338 and 1254 cm$^{-1}$ Dimethyl-2-Hydroxy-4-nitroterephthalate (3.0 g, 11.8 mmol) was reduced in 25 mL MeOH in a Parr hydrogenation bottle by 90 mg 10 % Pd-C under hydrogen (70 psi) for 3 h. The catalyst was removed by filtration and the solution was concentrated onto silica gel under reduced pressure. Elution with hexane/EtOAc (2:1) yielded 1.20.g dimethyl 2-amino-4-hydroxyterephthalate as a yellow solid, which was used without further purification.

$POCl_3$ (0.95 g, 6.2 mmol) was added to a stirred solution of 2-pyrrolidinone (1.00 g, 11.8 mmol) in 10 mL dry benzene. After 2 h, 1.20 g dimethyl 2-amino-4-hydroxyterephthalate (5.3 mmol) was added and the mixture was heated to reflux for 5 h: The reaction mixture was diluted with $CH_2Cl_2$, washed with saturated $NaHCO_3$. and concentrated under reduced pressure onto silica gel. Elution with EtOAc/MeOH (99:1) yielded 537 mg 9-carboxymethyl-8-hydroxy-2,3-dihydro-1H-pyrrolo[2,1-b][1,3]-quinazoline-6-one as white solid. IR: 1691, 1678, 1471, 1440 and 1249 cm$^{-1}$. NMR (200 MHz) δ 10.60 (1H, s), 8.21 (1H, s), 7.80 (1H, s), 4.19 (2H, t, J=7.2 Hz), 4.02 (3H, s), 3.15 (2H, t, J=7.9. Hz) and 2.20-2.40 ppm (2H, m).

9-carboxymethyl-8-hydroxy-2,3-dihydro-1H-pyrrolo[2,1-b][1,3]quinazoline-6-one (530 mg, 2.0 mmol) and 4-aminobutyraldehyde diethyl acetal (1.00 g, 6.2 mmol) were combined and heated to reflux for 90 s. The cooled reaction mixture was diluted with $CH_2Cl_2$, to which was added 2.0 mL trifluoroacetic acid and 5A molecular sieves. The mixture was stirred for 1 h, concentrated onto silica gel under reduced pressure, and eluted with EtOAc/MeOH (90:10). Decolonization of the solution with charcoal in $CHCl_3$/MeOH and removal of solvents under reduced pressure yielded 600 mg of product (99%) as a white solid with MP=245-250° C. IR: 1681, 1660, 1464, 1209 and 1137 cm$^{-1}$. $^1$H NMR (200 MHz) δ 8.21 (1H, s), 7.80 (1H, s), 5.58 (1H, t, J=5.8 Hz), 4.20 (2H, t, J=7.3 Hz), 3.75-3.95 (1H, m), 3.55-3.70 (1H, m), 3.19 (2H, t, J=8.0 Hz) and 1.90-2.60 ppm (6H, m).

EXAMPLE 7

(R,S)-Ethyl 7-hydroxy-9-oxo-3aH-benzo[e]pyrrolidino[2,1-b]1,3-oxazine-6-carboxylate

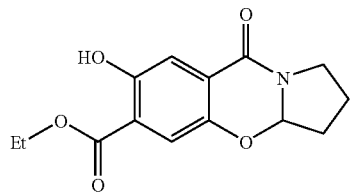

Diethyl 2,5-dihydroxyterephthalate (7.00 g, 27.5 mmol) and 4-aminobutyraldehyde diethylacetal (7.00 g, 43.4 mmol) were placed in a large test tube and boiled for 5 min. The reaction mixture was poured into a separatory funnel and thoroughly mixed with 800 mL EtOAc and 100 mL 6 N HCl. After 30 min the organic layer was dried over $Na_2SO_4$ and the solvent was evaporated to yield a yellow oil, which was purified on silica gel to provided 4.90 g (64%) colorless, fluffy crystals of the title compound with MP=139-141° C. IR: 1676, 1454, 1240 and 1200 cm$^{-1}$. $^1$H NMR (200 MHz) δ 10.48, (1H, s), 7.54 (1H, s), 7.47 (1H, s), 5.46 (1H, t, J=5.6

Hz), 4.42 (2H, q, J=7.2 Hz), 3.75-3.95 (1H, m), 3.50-3.70 (1H, m), 1.80-2.60 (4H, m) and 1.42 ppm (3H, t, J=7.2 Hz)

EXAMPLE 8

(R,S)-7-(Piperidylcarbonyl)-3aH-benzo[e]pyrrolidino[2,1-b]1,3-oxazaperhydroin-9-one

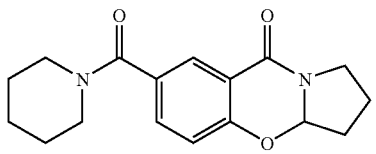

Trimethylaluminum (1.1 mL of 2M in toluene, 2.2 mmol) and 400 mg piperidine (4.7 mmol) were added to a solution of 500 mg methyl 9-oxo-3aH-benzo[3,4-e]pyrrolidino[2,1-b]1,3-oxazine-7-carboxylate (2.0 mmol) in 10 mL dry $CHCl_3$. The reaction mixture was heated to reflux for 4 h, cooled to ambient, and quenched with acetic acid. The mixture was concentrated onto silica gel under reduced pressure and eluted with hexane/EtOAc (1:1) to yield 537 mg (90%) white solid with MP=134-136° C. IR: 1673, 1626, 1434 and 1255 $cm^{-1}$. $^1$H NMR (200 MHz) δ 7.96 (1H, d, J=2.0 Hz), 7.53 (1H, dd, J=8.4, 2.2 Hz), 7.00 (1H, d, J=8.4 Hz), 5.52 (1H, t, J=5.7 Hz), 3.20-4.00 (6H, m) and 1.40-2.60 ppm (10H, m)

EXAMPLE 9

(R,S)-(7-methoxy-9-oxo(3aH-benzo[e]pyrrolidino[2,1-b]1,3-oxazin-6-yl))-N,N-dimethylcarboxamide

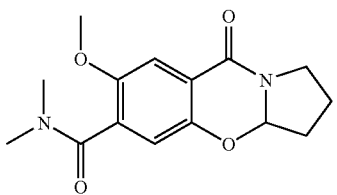

To 1.6 g (5 mmol) dimethylamine hydrochloride in 60 mL of dry $CH_2Cl_2$ was added 10 mL of 2.0 M $AlMe_3$ in toluene with stirring under Ar. Five mmoles (1.4 g) of the ester of Example 7 in 40 ml of $CH_2Cl_2$ was then added and refluxed for 0.5 h at which time the $CH_2Cl_2$ was distilled off and replaced with 40 mL of dry toluene. After refluxing for another hour the reaction mixture was mixed with 50 mL 3 M HCl. After the layers were separated, aqueous layer was extracted with 3×50 mL of $CH_2Cl_2$. The combined organic layers were dried over $NaSO_4$, and the solvent removed in vacuo to yield 810 mg crude phenolic amide (58% yield). IR: 1652 $cm^{-1}$. CI-MS 277.2 amu (M+H).

To the amide product from above (810 mg, 2.9 mmol) in 40 mL of anhydrous DMF under argon, was added 174 mg (4.35 mmol) 60% NaH all at once, with good stirring. After 10 min at room temperature, the bath temperature was raised to 65° C. and 0.25 mL of MeI (11.6 mmol) was added at once. After 2 h the reaction mixture was cooled to ambient and quenched with 5 mL of water. Water and DMF were then removed under vacuum and the residue was chromatographed on 150 g of silica gel with EtOAc. Combined fractions yielded 600 mg (71%). IR: 1666 and 1620 $cm^{-1}$. CI-MS 291.2 (M+H). $^1$H NMR (500 MHz) δ 7.43 (1H, s), 6.88 (1H, s), 5.49 (1H, m), 3.86 (3H, s), 3.84 (1H, m), 3.68 (1H, m), 3.11 (3H, s), 2.84 (3H, s), 2.49 (1H, m), 2.24 (1H, m), 2.16 (1H, m) and 1.95 ppm (1H, m).

EXAMPLE 10

(R,S)-N-(2-Hydroxyethyl)(7-hydroxy-9-oxo(3aH-benzo[e]pyrrolidino[2,1-b]1,3-oxazaperhydroin-6-yl))carboxamide

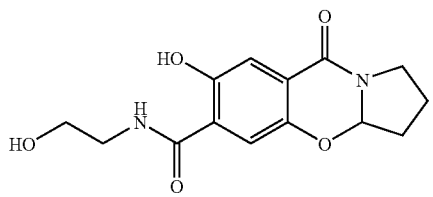

Ethyl 7-hydroxy-9-oxo-3aH-benzo[e]pyrrolidino[2,1-b]1,3-oxazine-6-carboxylate (Example 7 above) (1.20 g, 4.83 mmol) and ethanolamine (1.00 g, 16.3 mmol) were combined and heated to reflux for 90 s. The cooled reaction mixture was diluted with $CHCl_3$, acidified with acetic acid and concentrated onto silica gel under reduced pressure. Elution with $CH_2Cl_2$/MeOH (95:5) yielded 1.50 g hydroxyethylamide as a waxy solid. IR: 3000-3500, 1650, 1562, 1470, 1344, 1264, 1211 and 1066 $cm^{-1}$

EXAMPLE 11

(R,S), (R,S)-2H,3H,12aH,6aH-1,3-oxazolidino[2,3-b]pyrrolidino[2'',1''-2',3'](1,3-oxazino)[5',6'-2,1]benzo[4,5-e]1,3-oxazaperhydroine-4,10-dione

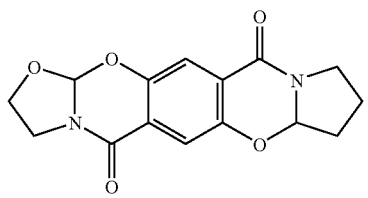

N-(2-Hydroxyethyl)(7-hydroxy-9-oxo(3aH-benzo[e]pyrrolidino[2,1-b]1,3-oxazaperhydroin-6-yl))carboxamide (product from Example 10) (1.50 g, 5.13 mmol) was suspended in 20 mL dry $CHCl_3$ together with 4.6 mL trimethylorthoformate (43 mmol) and 1.0 mL 96% formic acid (21 mmol) and heated to reflux for 6 h. The cooled reaction mixture was neutralized with potassium carbonate and concentrated onto silica gel under reduced pressure. Elution with hexane/EtOAc (1:1) and recrystallization from ethyl acetate afforded 430 mg white solid with MP=285-287° C. IR: 1675, 1458 and 1421 $cm^{-1}$. $^1$H NMR (200 MHz) δ 7.66 (0.5H, s), 7.64 (0.5H, s), 7.54 (0.5H, s), 7.51 (0.5H, s), 6.22 (0.5H, s), 6.21 (0.5H, s), 5.45-5.53 (1H, m), 4.20-4.40 (3H, m), 3.75-3.95 (1H, m), 3.55-3.70 (2H, m) and 1.90-2.58 ppm (4H, m).

EXAMPLE 12

(R,S), (R,S)-2H,3H,8H,9H,12aH,6aH-1,3-oxazolidino[2,3-b]1,3-oxazolidino[2'',3''-2',3'](1,3-oxazino)[5',6'-2,1]benzo[4,5-e]1,3-oxazaperhydroine-4,10-dione

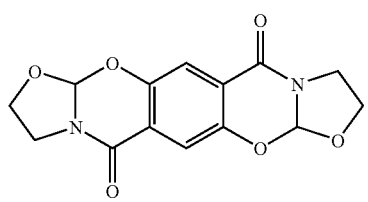

Diethyl 2,5-dihydroxyterephthalate and ethanolamine were mixed and heated to reflux for 90 s. The cooled mixture was diluted with chloroform, methanol, and acetic acid and concentrated onto silica gel under reduced pressure. Elution with $CH_2Cl_2$/MeOH (90:10) provided 1.20 g of crude bisamide. The crude amide was suspended in 20 mL dr $CHCl_3$ together with 4.6 mL trimethylorthoformate (43 mmol) and 1.0 mL 96% formic acid (21 mmol) and refluxed for 6 h. The cooled mixture was neutralized with potassium carbonate and concentrated onto silica gel under reduced pressure. Product was eluted and crystallized from ethyl acetate to yield 88 mg (3.5%) white powder with MP=305-306° C. IR: 1675, 1458 and 1421 $cm^{-1}$. $^1$H NMR (200 MHz) δ 7.62, (0.5H, s), 7.60 (0.5H, s), 6.24 (0.5H, s), 6.23 (0.5H, s), 4.20-4.42 (6H, m) and 3.50-3.70 ppm (2H, m).

EXAMPLE 13

(R,S), (R,S)-11aH,4aH-piperidino[2,1-b]piperidino[2'',1''-2',3'](1,3-oxazaperhydroino)[5',6'-4,5]benzo[e]1,3oxazine-7,14-dione

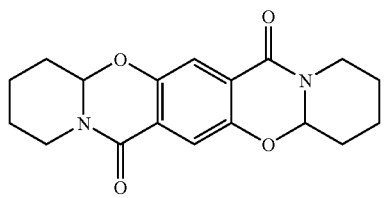

The synthesis was performed essentially as for Example 1, Method A except for substitution of 5-aminopentanal diethyl acetal for 4-aminobutyraldehyde diethyl acetal. $^1$H NMR (200 MHz) δ 7.502 (s), 7.493 (s), 5.19 (2H, dd, J=4.18 & 9.6 Hz), 4.47 (2H, dm, J=14 Hz), 2.78 (2H, tm, J=13 Hz), 2.24 (2H, m), 1.85 (6H, m) and 1.51 ppm (4H, m).

EXAMPLE 14

Preparation of (R,S)-6-(morpholin-4-ylcarbonyl)-3aH-benzo[e]pyrrolidino[2,1-b]1,3-oxazin-9-one

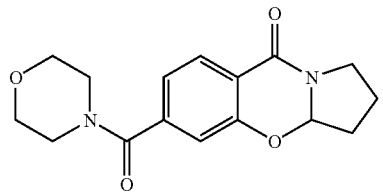

To a solution of methyl 9-oxo-3aH-benzo[e]pyrrolidino[2,1-b]1,3-oxazaperhydroine-6-carboxylate (compound of Example 3) in 20 mL methanol in a 125-mL Erlenmeyer flask was added 20 mL 1 N NaOH. After stirring vigorously for 30 min. the solution was acidified to pH 2 with 1N HCl. The resulting white precipitate was filtered and washed with 25 mL water. This solid was redissolved in ethyl acetate/methanol (1/1) and dried over anhydrous $Na_2SO_4$. The solution was concentrated to afford 703 mg (81%) of white solid. IR: 1712 and 1637 $cm^{-1}$.

To a suspension of 9-oxo-3aH-benzo[e]pyrrolidino[2,1-b]1,3-oxazine-6-carboxylic acid (300 mg, 1.29 mmol) in $CH_2Cl_2$ was added 1,1'-carbonyldiimidazole (209 mg, 1.29 mmol) in a 25-mL round bottom flask. After 2 h, morpholine was added via syringe. The resulting reaction mixture was stirred for 30 min and then washed with 1N HCl, saturated $NaHCO_3$, and brine. The organic layer was then dried over $Na_2SO_4$, filtered and concentrated to afford 375 mg of foam. The product was purified by chromatography on silica gel by eluting with ethyl acetate to yield 330 mg of off-white crystals (85%) with MP=184-186° C. IR: 1669 and 1636 $cm^{-1}$. $^1$H NMR δ 7.98 (1H, d, J=7.5 Hz), 7.10 (1H, d, J=8.9 Hz), 6.99 (1H, d, J=1.4 Hz), 5.51 (1H, t, J=6 Hz), 3.85 (1H, m), 3.78 (4H, bs), 3.60 (1H, m), 3.60 (2H, bs), 3.40 (2H, bs), 2.45 (1H, m), 2.27 (1H; m), 2.13 (1H, m) and 1.98 ppm (1H, m).

EXAMPLE 15

Preparation of (R,S)-6-[(4-Hydroxypiperidyl)carbonyl]-3aH-benzo[e]pyrrolidino[2,1-b]1,3-oxazin-9-one

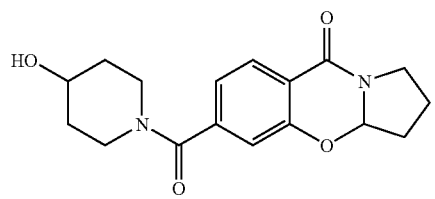

To a suspension of 9-oxo-3aH-benzo[e]pyrrolidino[2,1-b]1,3-oxazine-6-carboxylic acid (160 mg, 0.689 mmol) in 2 mL dichloromethane in a pear shaped 25-mL flask was added 1,1'-carbonyldiimidazole (112 mg, 0.689 mmol). Stirring was maintained under positive argon pressure and complete dissolution was achieved in 1 h. The solution was stirred an additional 2 h and then added slowly via syringe to a stirred solution of 4-hydroxypiperidine (148 mg, 3.44 mmol) in 5 mL $CH_2Cl_2$. The resulting reaction mixture was washed with 1N HCl, saturated NaHCO₃ and brine. The organic layer was dried over anhydrous Na₂SO₄, filtered and concentrated to afford 174 mg of white foam. The foam was crystallized from CH₂Cl₂/Et₂O to yield 158 mg of white solid (72%) with MP=130-135° C. IR: 3400, 1657 and 1619 cm⁻¹. ¹H NMR δ 7.96 (1H, d, J=7.9 Hz), 7.10 (1H, d, J=7.6 Hz), 7.00 (1H,s), 5.51 (1H, t, J=6.0 Hz), 4.16 (1H, bs), 3.99 (1H, m), 3.86 (1H, m), 3.63 (1H, m), 3.60 (1H, bs), 3.42 (1H, bs), 3.17 (1H, bs), 2.45 (1H, m), 2.27 (1H, m), 2.13 (1H, m), 2.0 (1H, bs), 1.99 (1H, m), 1.61 (2H, bs) and 1.49 ppm (1H, bs).

EXAMPLE 16

Preparation of (R,S)-6-[(4-methylpiperazinyl)carbonyl]-3aH-benzo[e]pyrrolidino[2,1-b]1,3-oxazin-9-one

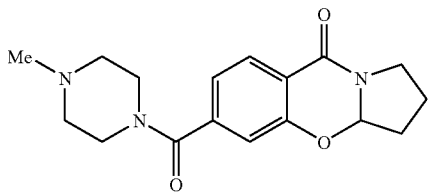

The procedure for the preparation of the compound of example 14 was followed with the substitution of 1-methylpiperazine for morpholine to give 378 mg (94%). IR: 1666 and 1633 cm. ¹H NMR δ 7.97 (1H, d), 7.10 (1H, d), 7.00 (1H, s), 5.51 (1H, t), 3.86 (1H, m), 3.79 (2H, bs), 3.62 (1H, m), 3.39 (1H, bs), 2.48 (4H, m), 2.32 (3H, s), 2.25 (2H, m), 2.13 (1H, m) and 1.96 ppm (1H, m).

EXAMPLE 17

Preparation of (R,S)-6-[(4-aminopiperidyl)carbonyl]-3aH-benzo[e]pyrrolidino[2,1-b]1,3-oxazin-9-one

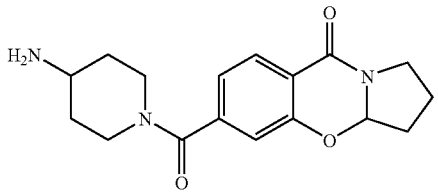

A 3-neck round-bottom flask fitted with a thermometer was charged with sodium azide (3.25 g, 50.0 mmol) and warm H₂O (3.25 mL). The resulting paste was stirred vigorously as 20 mL of benzene was added. The resulting heterogeneous solution was cooled to 5° C. and H₂SO₄ (1.34 mL, 25.0 mmol) was then added dropwise. The temperature of the solution was maintained below 10° C. and stirring was continued for an additional 5 min. The organic layer was decanted into an Erlenmeyer flask, dried over anhydrous Na₂SO₄, and used in the next reaction.

Diisopropylazodicarboxylate was added via syringe to a solution of 4-hydroxypiperidine (2.0 g, 20 mmol) and triphenylphosphine (6.75 g, 25.7 mmol) in CH₂Cl₂. The initial addition of a portion of the hydrazoic acid solution from above produced vigorous boiling and therefore the solution was cooled in an ice bath during the remainder of the addition. Stirring was continued in the ice bath, which was allowed to warm to ambient. After stirring at ambient for 16 hr, the solution was washed with H₂O followed by 1N HCl. The acidic solution was washed with Et₂O/EtOAc (2/1) and then made basic to pH 9 with 1N NaOH. The resulting cloudy aqueous solution was extracted with CH₂Cl₂. The organic layer was dried over Na₂SO₄, filtered and concentrated to afford 1.05 g of yellow oil (42%). IR: 2092 cm⁻¹. The crude product was used without further purification in the next step, which followed the procedure of Example 14 above with the substitution of 4-azidopiperidine for morpholine. The crude product was purified by chromatography on silica gel by elution with 3/1 hexane/ethyl acetate, which afforded 304 mg of 6-[(4-azidopiperidyl)carbonyl]-3aH-benzo[e]pyrrolidino[2,1-b]1,3-oxazin-9-one as a foam (73%). IR: 2095, 1670 and 1636 cm⁻¹

To a 50-mL Parr flask preflushed with argon was added 10% Pd/C (90 mg) followed by a solution of 304 mg of 6-[(4-azidopiperidyl)carbonyl]-3aH-benzo[e]pyrrolidino[2,1-b]1,3-oxazin-9-one (0.891 mmol) in 5 mL MeOH. The resulting solution was treated with hydrogen at 25 psi for 2 hr, filtered through celite and concentrated in vacuo. The residue was purified by chromatography on silica gel by eluting with 15/1 CH₂Cl₂/MeOH, followed by 15/1 CH₂Cl₂/MeOH (1% NH₄OH) to afford 220 mg of pure product. ¹H NMR (500 MHz) δ7.96 (1H, d, J=7.7 Hz), 7.09 (1H, d, J=8.5 Hz), 6.99 (1H, s), 5.51 (1H, t, J=5.9 Hz), 4.57 (1H, bd), 3.85 (1H, m), 3.67 (1H, bs), 3.63 (1H, m), 3.04 (1H, bs), 2.98 (1H, m), 2.94 (1H, bs), 2.45 (1H, m), 2.27 (1H, m), 2.13 (1H, m), 1.95 (1H, m), 1.95 (1H, bs), 1.77 (1H, bs), 1.39 (1H, bs) and 1.26 ppm (1H, bs).

EXAMPLE 18

Preparation of (R,S)-6-[(4-methylpiperidyl)carbonyl]-3aH-benzo[e]pyrrolidino[2,1-b]1,3-oxazin-9-one

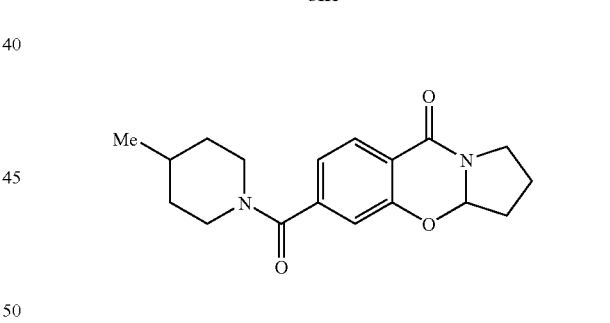

To a 2-neck, 100-mL round bottom flask fitted with a reflux condenser was added ethyl 9-oxo-3aH-benzo[e]pyrrolidino[2,1-b]1,3-oxazaperhydroine-6-carboxylate (343 mg, 1.41 mmol) and 20 mL CH₂Cl₂ under an argon atmosphere. The stirred solution was charged with trimethylaluminum (1.5 mL, 3.0 mmol) and after 30 min, 4-methylpiperidine (0.19 mL, 2.9 mmol) was added via syringe. After the solution was heated to reflux for 24 hr and allowed to stand at ambient temperature for an additional 72 hr, it was quenched with H₂O followed by slow addition of 6 N HCl. The organic layer was isolated and the aqueous layer was extracted with three 50-mL portions of CH₂Cl₂, which were combined with the organic layer and washed with water, brine, dried over Na₂SO₄, filtered and concentrated. The resulting oil was purified by chromatography on silica gel by eluting with 1:1 hexane/ethyl acetate. The pure fractions were concentrated to afford 323 mg of foam (54%). IR: 1668 and 1625 cm⁻¹. ¹H NMR (500 MHz) δ 7.96 (1H, d, J=7.5 Hz), 7.09 (1H, d), 6.99 (1H, s), 5.51 (1H, t, J=6.0 Hz), 4.66 (1H, bd), 3.86 (1H, m), 3.62 (2H, m), 2.96 (1H, bt), 2.76 (1H, bt), 2.44 (1H, m), 2.27 (1H, m), 2.12 (1H, m), 1.94 (1H, m), 1.77 (1H, bd), 1.65 (2H, m), 1.22 (1H, m), 1.08 (1H, m) and 0.98 ppm (3H, d, J=6.3 Hz).

EXAMPLE 19

Preparation of (R,S)-1-[(9-oxo-3aH-benzo[e]pyrrolidino[2,1-b]1,3-oxazin-6-yl)carbonyl]piperidine-4-carbonitrile

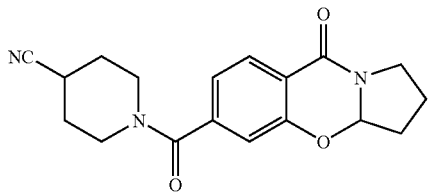

The procedure from the compound of Example 14 was followed except for the substitution of 4-cyanopiperidine for morpholine to yield 1-[(9-oxo-3aH-benzo[e]pyrrolidino[2,1-b]1,3-oxazin-6-yl)carbonyl]piperidine-4-carbonitrile as a white crystalline solid (61%). MP=154-156° C. IR: 1667 and 1633 cm$^{-1}$. $^1$H NMR δ 7.98 (1H, d, J=7.5 Hz), 7.08 (1H, d, J=7.4 Hz), 6.98 (1H, s), 5.52 (1H, t, J=5.96 Hz), 3.92 (1H, bs), 3.86 (1H, m), 2.27 (1H, m), 2.14 (1H, m), 1.96 (1H, m) and 1.85 ppm (4H, bs).

EXAMPLE 20

Preparation of (R,S),(R,S)-3-(hydroxymethyl)-6aH-chromano[7,6-e]pyrrolidino[2,1-b]1,3-oxazine-4,10-dione

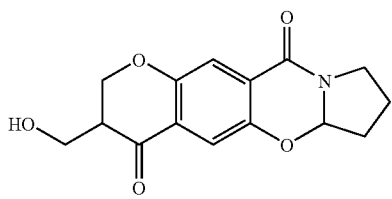

The isoxazoline of Example 18 (570 mg, 2.00 mmol) was dissolved in 100 mL methanol. A solution of boric acid (1.00 g) in 20 mL water and 1.00 g Raney-Nickel were added and the resulting mixture was treated with hydrogen at 1 atm for 2 hr at room temperature. The methanol was evaporated and the residue was extracted with 200 mL EtOAc, which was dried over Na$_2$SO$_4$. Evaporation of the solvent provided 420 mg of an oil, which was purified on silica gel with elution by 20% hexane/EtOAc. Crystallization from the elution solvent provided 202 mg of the ketone as a yellow solid with MP=189-190° C. MS: 290.1 (M+1). IR: 1667 and 1450 cm$^{-1}$. $^1$H NMR (500 MHz) δ 7.57 (1H, s), 7.56 (1H, s), 7.47, (2H, s), 5.43-5.46 (2H, m), 4.39-4.62 (4H, m), 3.99-4.06 (4H, m), 3.60-3.88 (4H, m), 3.00-3.05 (2H, m) and 1.92-2.47 ppm (8H, m) confirming the structure of the compound.

EXAMPLE 21

Preparation of 3,8-diethyl-2H,7H-1,3-oxazaperhydroino[5',6'-4,5]benzo[e]1,3-oxazine-4,9-dione

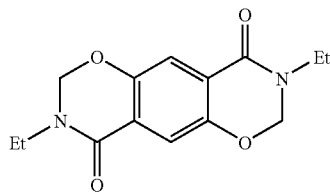

To 840 mg (3.0 mmol) diethyl 2,5-dihydroxyterephthalate in 100 mL anhydrous CHCl$_3$ under argon at 0° C. was added 10 mL (20 mmol) 2.0 M AlMe$_3$ in toluene with stirring. Following this 5.0 mL (77 mmol) of anhydrous ethyl amine was also added. During both additions gas evolution was extensive. The reaction mixture was slowly warmed to reflux and then refluxed under argon for 3 hr. At this point no starting material could be detected by TLC (1:1 EtOAc/hexanes). The reaction mixture was cooled to ambient and poured into 200 mL of 3 M HCl. The layers were separated and the aqueous layer was extracted with 3×100 mL of EtOAc. The combined organic layers were dried over Na$_2$SO$_4$ and the solvent was removed in vacuo to yield 600 mg of the diamide (79% yield). $^1$HNMR (500 MHz) δ 11.61 (2H, s), 6.94 (2H, s), 6.28 (2H, bs), 3.51 (4H, q) and 1.28 ppm (6H, t).

To 4.9 g (19.4 mmol) of accumulated diamide, 5.0 g (56 mmol) trioxane, and 4.6 g (20 mmol) camphor sulfonic acid in 340 mL of solvent (17% THF/CCl$_4$), was added 10 drops concentrated H$_2$SO$_4$. The colorless reaction mixture was then brought to reflux under argon with stirring. Water was removed azeotropically from the reaction mixture during the reflux by incorporating a 250 mL side arm addition funnel with 3A molecular sieves (100 g) in the vapor path. After 18 h the molecular sieves were changed, an additional 3.6 g (40 mmol) of trioxane was added and reflux was continued overnight. The following day the sieves were again changed, 3.8 g (42 mmol) trioxane was added, and the reaction mixture was refluxed another 4 h. No starting material remained in the coffee colored reaction mixture, which was cooled to 10-15° C. with an ice bath and then mixed with 200 mL of ice cold 0.5 M NaOH. The separated organic layer was washed with 100 mL of H$_2$O and dried over Na$_2$SO$_4$. Removal of solvent in vacuo yielded 2.5 g crude material, which was chromatographed on 150 g of silica gel using 2 L EtOAc to yield 1.5 g (28%) product with MP=236-237° C. Recrystallization from 3:1 Et$_2$O/CH$_2$Cl$_2$ provided 1.09 g (20%) of 3,8-diethyl-2H,7H-1,3-oxazaperhydroino[5',6'-4,5]benzo[e]1,3-oxazine-4,9-dione. CIMS m/z=220.1 and 277.2 amu. $^1$HNMR (500 MHz) d 7.57 (1H, s), 5.16 (2H, s), 3.60 (2H, q, J=7.23 Hz) and 1.25 (3H, t, J=7.23 Hz).

EXAMPLE 22

Preparation of (R,S)-3-methyl-2H,6aH-pyrrolidino[2",1"-3',2']1,3-oxazino[5',6'-4,5]benzo[e]1,3-oxazaperhydroine-4,10-dione

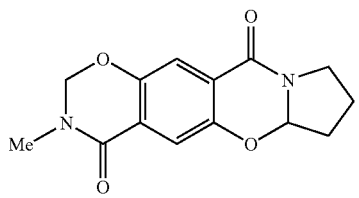

To 1.4 g (5.1 mmol) ethyl 7-hydroxy-9-oxo-3aH-benzo[e]pyrrolidino[2,1-b]1,3-oxazine-6-carboxylate (the product from Example 7) in 120 mL of dry $CHCl_3$ (0° C. water bath) was added 5.0 mL (10 mmol) 2.0 M $AlMe_3$ in $CH_2Cl_2$ and 6.0 mL (12 mmol) of a 2.0 M solution of methylamine in THF. After 15 min of steady gas evolution, the water bath was replaced with an oil bath and the reaction mixture was refluxed for 1.5 h, followed by overnight stirring at room temperature. After an additional 6.0 mL (12 mmol) of $AlMe_3$ solution and 6.0 mL (12 mmol) of methylamine in THF were added, the reaction mixture was refluxed for 2 h and poured into 200 mL of 3 M HCl with thorough mixing. The separated aqueous layer was extracted with 3×100 mL of $CHCl_3$ and the combined organic layers were dried over $MgSO_4$. The solvents were removed in vacuo to yield 1.2 g phenolic amide in 91% yield as a waxy solid. CI MS: 263.3 amu (M+1). IR: 3319, 1652, 1608 and 1455 $cm^{-1}$.

To 1.0 g (3.8 mmol) of the phenolic amide above in 300 mL anhydrous $CHCl_3$ under argon was added 900 mg (10.0 mmol) s-trioxane, followed by 2.0 g $H_2SO_4$ with stirring. The reaction mixture was refluxed overnight, cooled to room temperature, and then washed with 200 mL saturated $NaHCO_3$. The aqueous layer was back extracted with 4×100 mL of $CH_2Cl_2$ and the combined organic layers were dried over $MgSO_4$. The solvent was removed in vacuo to give 900 mg of a pale yellow residue, which was chromatographed on 400 g of silica gel (EtOAc) to yield 800 mg (77%) of a colorless powder. MP=195-196° C. IR 1672 and 1454 $cm^{-1}$. CI-MS 275.3 amu (M+1). $^1$H-NMR (500 MHz) δ 7.57 (1H, s), 7.54 (1H, s), 5.47 (1H, t, J=5.7 Hz), 5.16(2H, m), 3.83 (1H, m), 3.65(1H, m), 3.12 (3H, s), 2.45 (1H, m), 2.26 (1H, m), 2.14 (1H, m) and 1.96 ppm (1H, m).

EXAMPLE 23

Preparation of (R,S)-3-ethyl-2H,6aH-pyrrolidino[2",1"-3',2']1,3-oxazino[5',6'-4,5]benzo[e]1,3-oxazaperhydroine-4,10-dione

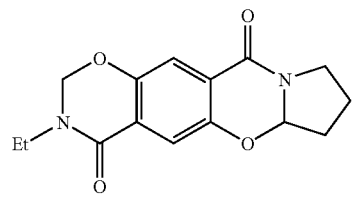

The synthesis of 3-ethyl-2H,6aH-pyrrolidino[2",1"-3',2']1,3-oxazino[5',6'-4,5]benzo[e]1,3-oxazaperhydroine-4,10-dione was performed essentially as described for Example 22 above with the substitution of anhydrous ethylamine for the solution of methylamine. The crude material was applied to 50 g of silica gel and eluted with EtOAc to yield pure product in 61% yield with MP=197-198° C. IR: 1667 and 1451 $cm^{-1}$. CI-MS 289.2 amu (M+H). $^1$H NMR (500 MHz) δ 7.57 (1H, s), 7.54 (1H, s), 5.47 (1H, t, J=6.0 Hz), 5.18 (2H, m), 3.66 (1H, m), 3.65 (2H, m), 2.48 (1H, m), 2.26 (1H, m), 2.17 (1H, m), 1.94 (1H, m) and 1.22 ppm (3H, t, J=7.2 Hz).

EXAMPLE 24

Preparation of (R,S)-3-propyl-2H,6aH-pyrrolidino[2",1"-3',2']1,3-oxazino[5',6'-4,5]benzo[e]1,3-oxazaperhydroine-4,10-dione

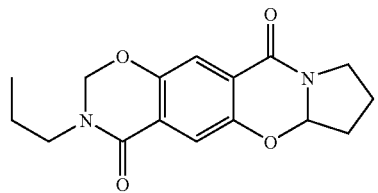

The synthesis of 3-propyl-2H,6aH-pyrrolidino[2",1"-3',2']1,3-oxazino[5',6'-4,5]benzo[e]1,3-oxazaperhydroine-4,10-dione was performed essentially as described for Example 22 above with the substitution of n-propylamine for the solution of methylamine to yield a waxy residue, which was chromatographed on silica gel to give a colorless solid with MP=153-154° C. IR (NaCl) 1667 and 1454 $cm^{-1}$. CI-MS 303.1 amu (M+1). $^1$H NMR δ 7.58 (1H, s), 7.54 (1H, s), 5.45 (1H, t, J=6.1 Hz), 5.17 (2H, m), 3.87 (1H, m), 3.65 (1H, m), 3.52 (2H, m), 2.48 (1H, m), 2.30 (1H, m), 2.15 (1H, m), 1.97 (1H, m), 1.69 (1H, m), 1.68 (2H, m) and 0.99 ppm (3H, t, J=7.5 Hz).

EXAMPLE 25

Preparation of (R,S)-3-(methylethyl)-2H,6aH-pyrrolidino[2",1"-3',2']1,3-oxazino[5',6'-4,5]benzo[e]1,3-oxazaperhydroine-4,10-dione

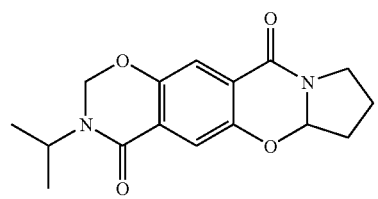

The synthesis of 3-(methylethyl)-2H,6aH-pyrrolidino[2",1"-3',2']1,3-oxazino[5',6'-4,5]benzo[e]1,3-oxazaperhydroine-4,10-dione was performed essentially as described for Example 22 above with the substitution of isopropylamine for the solution of methylamine. Final purification was by silica gel column chromatography (35% yield). MP=204-205° C. IR: 1664 and 1452 $cm^{-1}$. CI-MS 303.3 amu (M+1). $^1$H NMR (500 MHz) δ 7.58 (1H, s), 7.53 (1H, s), 5.49 (1H, t, J=5.9 Hz), 5.14 (2H, m), 4.87 (1H, sept, J=4.9 Hz), 3.88 (1H, dt, J=11.6 & 7.3 Hz), 3.65 (1H, m), 2.45 (1H, m), 2.27 (1H, m), 2.13 (1H, m), 1.96 (1H, m) and 1.26 ppm (6H, m).

EXAMPLE 26

Preparation of (R,S)-3-cyclopentyl-2H,6aH-pyrrolidino[2",1"-3',2']1,3-oxazino[5',6'-4,5]benzo[e]1,3-oxazaperhydroine-4,10-dione

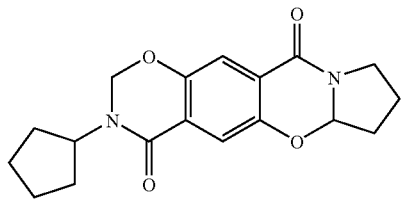

The synthesis of (R,S)-3-cyclopentyl-2H,6aH-pyrrolidino[2",1"-3',2']1,3-oxazino[5',6'-4,5]benzo[e]1,3-oxazaperhydroine-4,10-dione was performed essentially as described for Example 22 above with the following exceptions: Neat cyclopentylamine was substituted for the solution of methylamine in THF; toluene was used as the solvent for the reaction; instead of refluxing the solution over night it was heated to 80° C. Final purification was by silica gel column chromatography (56% yield). MP=184-188° C. CI-MS 329.1 amu (M+1). $^1$H-NMR (500 MHz) δ 7.58 (1H, s), 7.53 (1H, s), 5.47 (1H, t, J=6 Hz), 5.14 (2H, s), 4.94 (1H, p, J=8.5 Hz) 3.85 (1H, m), 3.63 (1H, m), 2.45 (1H, m), 2.26 (1H, m), 2.13 (1H, m), 1.99 (1H, m), 1.75 (1H, m), 1.66 (1H, m) and 1.53 ppm (1H, m).

EXAMPLE 27

Preparation of (R,S)-3-[3-(2-oxopyrrolidinyl)propyl]-2H,6aH-pyrrolidino[2",1"-3',2']1,3-oxazino[5',6'-4,5]benzo[e]1,3-oxazaperhydroine-4,10-dione

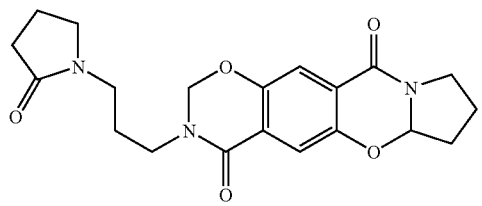

The synthesis was essentially as for the compound of Example 22 with the exception that five equivalents of camphorsulfonic acid were employed in the final cyclization step. MP =189-190° C. IR: 1667 cm$^{-1}$. CI-MS 386.3 amu (M+1). $^1$H NMR (500 MHz) δ 7.55 (2H, s), 5.47 (1H, t, J=6.0 Hz), 5.22 (2H, s), 3.85 (1H, m), 3.64 (1H, m), 3.52 (2H, m), 3.42 (2H, m), 3.37 (2H, m), 2.46 (1H, m), 2.41 (2H, m), 2.26 (1H, m), 2.14 (1H, m), 2.05 (2H, m) and 1.87-2.0 ppm (3H, m).

EXAMPLE 28

Preparation of (R,S)-3-(2H-benzo[d]1,3-dioxolen-5-ylmethyl)-2H,6aH-pyrrolidino[2",1"-3',2']1,3-oxazino[5',6'-4,5]benzo[e]1,3-oxazaperhydroine-4,10-dione

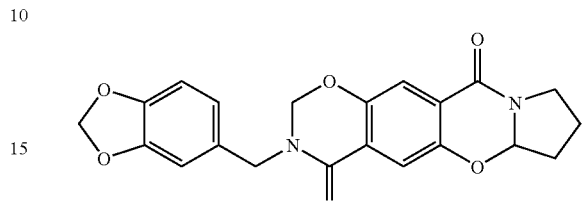

The synthesis of 3-(2H-benzo[d]1,3-dioxolen-5-ylmethyl)-2H,6aH-pyrrolidino[2",1"-3',2']1,3-oxazino[5',6'-4,5]benzo[e]1,3-oxazaperhydroine-4,10-dione was carried out essentially in the same manner as for Example 22 above with the exception that piperonylamine was substituted for methylamine. IR spectroscopy (NaCl) 1680 and 1445 cm$^{-1}$. CI-MS 395.3 amu, (M+H). $^1$H-NMR (500 MHz): δ 7.62 (1H, s), 7.53 (1H, s), 6.87 (1H, s), 6.78 (1H, s), 6.79 (1H, s), 5.96 (2H, s), 5.49 (1H, m), 5.14 (2H, m), 4.70 (2H, dd), 3.88 (1H, m), 3.65(1H, m), 2.48 (1H, m), 2.24 (1H, m), 2.15 (1H, m) and 1.97 ppm (1H, m).

EXAMPLE 29

Preparation of (R,S)-3-(2,2,2-trifluoroethyl)-2H,6aH-pyrrolidino[2",1"-3',2']1,3-oxazino[5',6'-4,5]benzo[e]1,3-oxazaperhydroine-4,10-dione

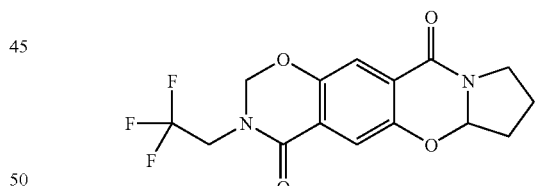

The procedure for the synthesis of 3-(2,2,2-trifluoroethyl)-2H,6aH-pyrrolidino[2",1"-3',2']1,3-oxazino[5',6'-4,5]benzo[e]1,3-oxazaperhydroine-4,10-dione was essentially the same as for example 22 with the exception that trifluoroethylamine was substituted for methylamine.

The trioxane procedure was performed on a 5 mmol scale resulting in 1.2 g purified trifluoroethylbenzoxazine, in 70% yield with m.p. 179-180° C. IR spectroscopy (NaCl) 1672 and 1454 cm$^{-1}$. CI-MS, 343.1 (M+H). $^1$H-NMR (500 MHz) δ 7.58 (1H, s), 7.57 (1H, s), 5.48 (1H, m), 5.29 (2H, m), 4.21 (2H, m), 3.84 (1H, m), 3.67 (1H, m), 2.52 (1H, m), 2.30 (1H, m), 2.18 (1H, m) and 2.00 ppm (1H, m).

EXAMPLE 30

Preparation of (R,S)-4-ethyl-2H,3H,7aH-pyrrolidino[2",1"-3',2']1,3-oxazino[5',6'-4,5]benzo[f]1,4-oxaza-perhydroepine-5,11-dione

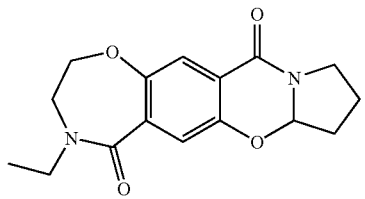

Commercially available 2,5-dihydroxyterephtalic acid diethylester (7.00 g; 27.5 mmol) and 4-aminobutyraldehyde diethylacetal (7.00 g; 43.4 mmol) were placed in a test tube and heated to reflux for 5 min. The reaction mixture was poured into a separatory funnel with 800 mL EtOAc and 100 mL 6N HCl. After 30 min the organic layer was separated, dried over $Na_2SO_4$ and the solvent evaporated to yield a yellow oil. Flash chromatography (silica gel, ethyl acetate/hexane 80/20) yielded 4.90g (64%) of colorless, fluffy crystals with the following properties: MP=139-141° C. $^1$H NMR (300 MHz, $CDCl_3$) δ 10.41 (1H, s), 7.49 (1H, s), 7.44 (1H, s), 5.41 (1H, t, J=5.7 Hz), 4.38 (2H, q, J=7.2 Hz), 3.86-3.76 (1H, m), 3.64-3.53 (1H, m), 2.46-2.33 (1H, m), 2.25-2.02 (2H,m), 1.99-1.82 (1H, m), 1.38 ppm (3H, t, J=7.2 Hz).

To a solution of 2.0 g (7.21 mmol) of the intermediate phenol in 50 mL toluene were added 15 mL 1,2-dibromoethane and 2.4 g (17.4 mmol) $K_2CO_3$. The mixture was refluxed for 48 hr, until the starting material was consumed. The solvent was evaporated and 200 mL EtOAc and 100 mL water were added. The organic phase was dried over $Na_2SO_4$, and the solvent evaporated. Flash chromatography on silica gel (EtOAc/Hexane 60/40) yielded a colorless oil, which crystallized after 1 hr. (2.1 g, 76%). MP=98-99° C. $^1$H NMR (300 MHz, $CDCl_3$) δ 7.47 (1H, s) 7.36 (1H, s), 5.46 (1H, t, J=5.9 Hz), 4.45-4.30 (4H, m), 3.89-3.79 (1H, m), 3.66 (2H, t, J=6.0 Hz), 3.69-3.57 (1H, m), 2.50-2.38 (1H, m), 2.31-2.06 (2H, m), 2.05-1.87 (1H, m), 1.39 ppm (3H, t, J=7.1 Hz).

720 mg (1.87 mmol) of the intermediate bromide was dissolved in 30 mL ethanol. A solution of 350 mg KOH (6.25 mmol) in 10 mL water was added. The reaction was complete after 10 minutes. 100 mL water and 200 mL EtOAc were added, and the mixture was acidified with HCl to pH2. The organic phase was dried over $Na_2SO_4$, and the solvent evaporated, which yielded a colorless oil (700 mg).

The oil was dissolved in 50 mL THF and 1 mL $H_2NEt$ was added and the mixture was stirred for 72 hr at room temperature. The solvent was evaporated and the residue redissolved in 50 mL THF. To the solution was added 253 mg (1.87 mmol) HOBT, 228 mg (1.87 mmol) DMAP, 189 mg (1.87 mmol) $NEt_3$ and 1.08 g (5.61 mmol) EDCI and the mixture was stirred for 24 hr. The solvent was evaporated and 100 mL EtOAc and 100 mL aqueous HCl (pH=2) were added. The organic phase was dried over $Na_2SO_4$ and evaporated. Flash chromatography on silica gel (EtOAc/Hexane 75/25) yielded 335 mg of a colorless oil (59%). Crystallization from EtOAc/Hexane yielded 283 mg white crystals with the following properties: MP=180-181° C. IR: 1670, 1631, 1475, 1443, 1034 $cm^{-1}$. $^1$H NMR (500 MHz, $CDCl_3$) δ 7.58 (1H, s), 7.36 (1H, s), 5.47 (1H, t, J=6 Hz), 4.36 (1H, ddd, J=10.9; 8.5 and 4.1 Hz), 4.29 (1H, ddd, J=10.9; 4.6 and 4.2 Hz), 3.88-3.81 (1H, m), 3.66 (2H, q, J=7.1 Hz), 3.65-3.58 (1H, m), 3.52 (1H, ddd, J=15.8; 8.5 and 4.2 Hz), 3.40 (1H, ddd, J=15.8; 4.6 and 4.1 Hz), 2.48-2.41 (1H, m), 2.30-2.22 (1H, m), 2.17-2.08 (1H, m), 2.00-1.90 (1H, m), 1.26 ppm (3H, t, J=7.1 Hz).

EXAMPLE 31

Preparation of (R,S)-3-(4-oxo-4-pyrrolidinylbutyl)-2H,6aH-pyrrolidino[2",1"-3',2']1,3-oxazino[5',6'-4,5]benzo[e]1,3-oxazaperhydroine-4,10-dione

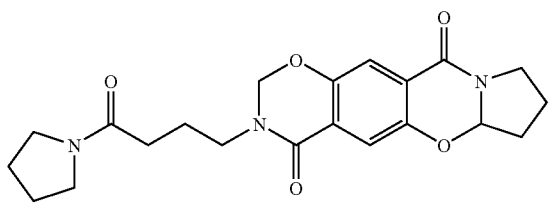

To 4.8 g (20 mmol) CBZ-GABA (Org. Syn. Vol. III, Pg. # 167) in 50 mL of $CHCl_3$ was added 3.5 g (22 mmol) CDI under argon atmosphere with stirring. After 1 hr, 5 mL (excess) pyrrolidine was added. The reaction mixture was stirred for another hour before it was washed with 100 mL of 1 M aqueous HCl, 100 mL of saturated aqueous $NaHCO_3$, and dried over $Na_2SO_4$. Concentration in vacuo yielded 6.0 g of intermediate amide (one spot to TLC, EtOAc). The amide was dissolved in 50 mL of EtOH and hydrogenated overnight at 30 psi with 800 mg of 10% Pd/C. Removal of the solvent yielded 3.5 g intermediate amine as a pale yellow waxy liquid.

To 1.3 g (5.22 mmol) of salicylic acid intermediate (see Example 33 below for its synthesis) suspended in 40 mL of DMF was added 930 mg (5.74 mmol) of CDI. After 10 min the suspension became a clear brown solution and it was heated at 60-80° C. for 4 hr. The solution was then cooled to room temperature before 1.5 g (10 mmol) of the intermediate amine was added. The reaction mixture was allowed to stir overnight before the solvent was removed at oil pump pressure (40° C.). The residue was dissolved into 200 mL of $CH_2Cl_2$, washed with 50 mL of 1 M HCl and 50 mL saturated $NaHCO_3$, dried over $Na_2SO_4$, and concentrated in vacuo, to yield 1.1 g of amide intermediate (one spot on TLC).

To 1.1 g (2.9 mmol) of amide intermediate in 150 mL of 33% $CH_2Cl_2/CHCl_3$ was added 5.4 g (60 mmol) trioxane, 2.3 g (100 mmol) camphor sulfonic acid and 10 drops $H_2SO_4$, with stirring under argon atmosphere. The resulting two-phase system was heated to reflux and water was removed by 50 g of 4 Å molecular sieves contained in a 125 mL side arm addition funnel. After the mixture was refluxed overnight, the sieves were changed and refluxing was continued another 3 hours. The reaction mixture was cooled to room temperature and shaken with 100 mL of 1 M NaOH. The aqueous layer was extracted with 3 ×100 mL of $CH_2Cl_2$. The combined organic layers were washed with 200 mL of water, dried over $Na_2SO_4$, and concentrated in vacuo to yield 1.5 g of crude product. Flash chromatography on 150 g silica gel with 20% ETOH in EtOAc gave 750 mg of product (63%), as a pale green crystalline solid, 98% pure by LC-MS (M+H)=400 amu with the following properties: IR: 1666, 1638, 1454, 1428 $cm^{-1}$. $^1$H NMR (300 MHz, $CDCl_3$), δ 7.54 (1H, s), 7.53 (1H, s), 5.46 (1H, t, J=5.6 Hz), 5.21 (2H, s), 3.85 (1H, m), 3.62 (1H, m), 3.61 (2H, t, J=7.0 Hz), 3.40 (4H, m), 2.44 (1H, m), 2.33 (2H, t, J=6.9 Hz), 2.26 (1H, m), 2.13 (1H, m), 2.0 (4H, m), 1.96 (1H, m) and 1.85 ppm (2H, m).

EXAMPLE 32

Preparation of (R,S)-3-(3-morpholin-4-ylpropyl)-2H, 6aH-pyrrolidino [2",1"-3',2']1,3-oxazino[5',6'-4,5] benzo[e]1,3-oxazaperhydroine-4,10-dione

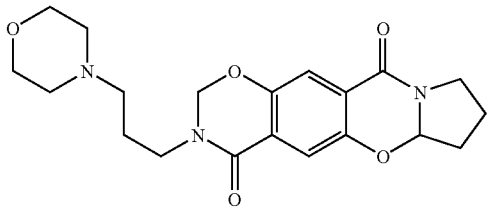

The synthesis of 3-(3-morpholin-4-ylpropyl)-2H,6aH-pyrrolidino[2",1"-3',2']1,3-oxazino[5',6'-4,5]benzo[e]1,3-oxazaperhydroine-4,10-dione was carried out as generally indicated for Example 22 above. More specifically, to 1.15 g (4.0 mmol) ethyl 7-hydroxy-9-oxo-3aH-benzo[e]pyrrolidino[2,1-b]1,3-oxazine-6-carboxylate (the product from Example 7) in 30 mL $CH_2Cl_2$ under argon was added 3.0 mL (6.0 mmol) $AlMe_3$ with stirring. 1-(3-Aminopropyl)-morpholine (0.45 mL; 3.0 mmol) was added and the resulting mixture was allowed to stir overnight at room temperature. An additional 0.6 mL of 1-(3-aminopropyl)-morpholine was added over a period of 3.5 hr as the mixture was refluxed. The reaction was incomplete as indicated by TLC, therefore the reaction mixture was cooled to room temperature and 1.0 mL (2.0 mmol) 2.0 M $AlMe_3$ in toluene was added. The mixture was refluxed for another 2 hr and at this time TLC indicated completion. The reaction mixture was cooled to 5° C. and then quenched by the careful addition of 12 M HCl with stirring. The mixture was adjusted to pH 7 with 10 M NaOH and extracted with 2×250 mL of THF. The solution was dried over $Na_2SO_4$ and evaporation of the solvent yielded 1.8 g of crude phenolic amide with only traces of primary amine.

To 1.8 g of the crude intermediate in 75 mL 88% formic acid was added 400 mL benzene and the resulting two phase system was brought to reflux under argon. After removal of 350 mL benzene by distillation, an additional 400 mL of benzene was added and the reaction mixture was refluxed overnight with stirring under argon. All of the benzene was removed by distillation at atmospheric pressure and then 2×200 mL of benzene was added and subsequently removed in vacuo to leave 2.2 g of an oily residue. The residue was treated with 50 mL of triethylamine, which was then removed in vacuo. The residue from this operation was passed through a short column (50 g silica, 50% EtOH/EtOAc) to remove any primary amine. After removal of solvent from the chromatography fractions in vacuo, the 1.5 g of residue as taken up in 1.0 L of EtOAc and subsequently washed with 2×50 ml of 1.0 M NaOH, 2×50 mL brine and then dried over $Na_2SO_4$. Solvent was removed in vacuo to yield 700 mg of a thick brown residue, which was chromatographed on 75 g of silica gel (EtOH/EtOAc, 2:3) to yield a colorless solid with m.p.=153-155° C. IR spectroscopy (NaCl): 1665 and 1454 $cm^{-1}$. CI-MS 388 amu (M+1). $^1$H NMR (500 MHz) δ 7.56 (1H, s); 7.54 (1H, s); 5.47 (1H, m); 5.22 (2H, dd); 3.85 (1H, s), 3.71 (5H, m), 3.66 (3H, m), 2.50 (6H, m), 2.28 (1H, m), 2.18 (1H, m), 2.01 (1H, m) and 1.87 ppm (2H, m).

EXAMPLE 33

Preparation of (R,S)-methyl 2-(4,10-dioxo-2H,6aH-pyrrolidino[2",1"-3',2']1,3-oxazino[5',6'-4,5]benzo[e]1,3-oxazaperhydroin-3-yl)acetate

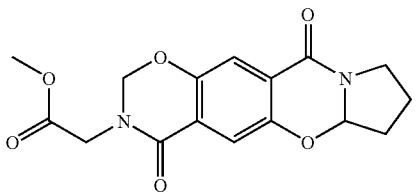

To 2.5 g (9.0 mmol) of ester (the product from Example 7) in 50 mL of THF/MeOH, 1:1 was added 50 mL of 1.0 M aqueous NaOH. The resulting yellow solution was heated at 40° C. for 1 hr under argon, with stirring. TLC indicated that no starting ester remained. The reaction mixture was concentrated to 20 mL in vacuo, then cooled to 4° C. in an ice bath and adjusted to pH 4 with conc. HCl. We copious white precipitate was collected on a Buchner funnel, washed with several small portions of cold water and dried under vacuum overnight. The yield was 1.3 g (54%) of the salicylic acid intermediate as a fine colorless solid.

The salicylic acid from above was suspended in 20 mL of dry DMF with stirring under argon atmosphere. To the dry suspension was added 0.92 g (5.7 mmol) CDI and the stirred mixture was heated to 50° C. for 1 hr, at which point a yellow solution formed. To this solution was added 1.0 g (8.0 mmol) glycine methyl ester hydrochloride followed by 5 mL (28.7 mmol) of diisopropyl ethylamine at 42° C. with stirring. The reaction mixture was stirred at 40-45° C. overnight under argon. Concentration of the solution gave a residue, which was placed under vacuum for 16 h at 0.1 mm Hg. The dry residue (5.8 g) was dissolved into 500 mL of EtOAc, washed with 100 mL 3 M HCl, 2×100 mL water, dried over $Na_2SO_4$ and then filtered through 200 g of silica gel. The silica gel was washed with 1500 mL of EtOAc. Evaporation of EtOAc from the purified phenolic amide intermediate yielded 1.2 g (72%) of a white solid. CI-MS 321, (M+1); 362 amu, (M+$CH_3$CN+H).

To 2.0 g of phenolic amide (combined yield from two batches) in 300 mL of 33% $CH_2Cl_2$/$CHCl_3$ was added 4.6 g (20 mmol) of camphor sulfonic acid and 2.0 g (22 mmol) trioxane. The resulting solution was refluxed for 3 hrs. Five drops of concentrated $H_2SO_4$ were added to the reaction mixture, after which it was refluxed for another 2 h. The reaction mixture was cooled to 10° C. with an ice bath, then poured into 100 mL of 1 M NaOH with stirring. The aqueous layer was separated and extracted with 3×50 mL of $CH_2Cl_2$. The combined organic layers were then washed with 100 mL water, dried over $MgSO_4$ and the solvent was removed in vacuo, to give 1.1 g of crude bis-benzoxazine as a waxy solid. The crude product was chromatographed on 150 g of silica gel with EtOAc as the eluent to yield 650 mg (31%) of crystalline material with MP=161-162° C. IR (NaCl) 1748, ester carbonyl; 1665, amide carbonyls and 1453 $cm^-$C—O. CI-MS 333 amu, (M+1). $^1$H-NMR ($CDCl_3$) δ 7.60 (1H, s), 7.58 (1H, s), 5.5 (1H, m), 5.30 (2H, m), 4.35 (2H, m), 4.89

(1H, m), 3.78 (3H, s), 3.68 (1H, s), 2.50 (1H, m), 2.39 (1H, m), 2.15 (1H, m) and 1.90 ppm (1H, m).

EXAMPLE 34

Preparation of (R,S)-3-(2-oxo-2-pyrrolidinylethyl)-2H,6aH-pyrrolidin[2″,1″-3′,2′]1,3-oxazino[5′,6′-4,5]benzo[e]1,3-oxazaperhydroine-4,10-dione

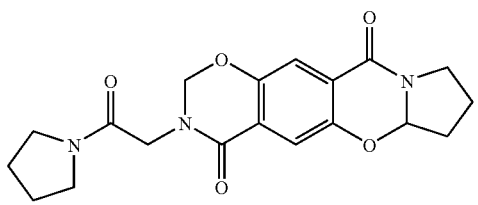

To 450 mg (1.2 mmol) (R,S)-methyl 2-(4,10-dioxo-2H,6H-pyrrolidino[2″,1″-3′,2′]1,3-oxazino[5′,6′-4,5]benzo[e]1,3-oxazaperhydroin-3-yl)acetate (Example 33) in 80 mL dry CHCl$_3$ was added 0.15 mL (1.8 mmol) pyrrolidine, followed by 0.9 mL (1.8 mmol) 2.0 M. ALMe$_3$ in toluene. The addition was performed at room temperature under argon atmosphere with vigorous stirring. The reaction mixture was refluxed for 1 hr followed by stirring overnight at room temperature. Pyrrolidine (0.3 mL; 3.6 mmol) was added followed by 1.8 mL (3.6 mmol) 2.0 M ALMe$_3$ in toluene. The reaction mixture was refluxed for 5 hr, at which point no starting material was visible by TLC. The reaction mixture was cooled to 5° C. and then stirred with 50 mL of 1 M HCl. The aqueous layer was separated and extracted with 3×50 mL CH$_2$Cl$_2$. The combined organic layers were washed with 50 mL saturated aqueous NaHCO$_3$, dried over Na$_2$SO$_4$, and concentrated in vacuo. The crude amide (600 mg) was chromatographed on 150 g silica gel by eluting with 10% EtOH in EtOAc, followed by crystallization from 10 mL of EtOAc to yield 458 mg (99%) of a crystalline powder with MP =257-259° C. IR (NaCl) 1748 carbonyl, 1665, amide carbonyl and 1453 cm$^{-1}$ C—O. CI-MS 372, (M+H); 394, (M+Na), 435 amu, (M+Na+CH$_3$CN). $^1$H-NMR (500 MHz, CDCl$_3$), δ 7.56 (1H, s), 7.55 (1H, s), 5.50 (1H, m), 5.41 (2H, m), 4.38 (2H, m), 3.87 (1H, m), 3.68 (1H, m), 3.52 (4H, m), 2.49 (1H, m), 2.28 (1H, m), 2.18 (1H, m), 2.08 (2H, m), 2.03 (1H, m) and 1.95 ppm (1H, m).

EXAMPLE 35

Preparation of 7-(cyclohexylcarbonyl)-3-(2-methoxyethyl)-2H-benzo[e]1,3-oxazaperhydroin-4-one

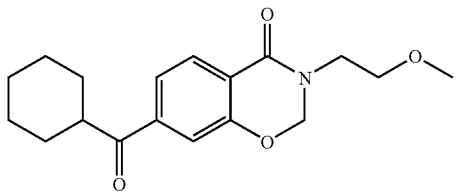

Commercially available 3-hydroxybenzaldehyde (10.0 g; 81.9 mmol) was dissolved in 40 mL CH$_2$Cl$_2$ and 40 mL HC(OEt)$_3$ at room temperature followed by the addition of 3.0 mL of a 1 M solution of BCl$_3$ in hexane. After the mixture was stirred for 30 min, it was filtered through 3 cm of silica gel and the silica gel was washed with a mixture of 150 mL hexane and 250 mL EtOAc. The resulting orange oil, which was obtained after removal of the solvent, was dissolved in 40 mL THF and 3.5 g of NaH (~87 mmol, ~60% in mineral oil) was added in portions. The mixture was heated to 170° C. in a steel cylinder in the presence of CO$_2$ (600 psi) for 2 hr. After cooling and venting of excess CO$_2$, the mixture was partitioned between 150 mL EtOAc and 200 ml water. The water phase was treated with H$_2$SO$_4$ (pH 2), extracted with 250 mL EtOAc and dried over Na$_2$SO$_4$. The solvent was evaporated to yield 9.2 g of a dark brown oil.

The dark brown oil (9.2 g, ~38 mmol) was dissolved in 80 mL CH$_2$Cl$_2$ and 9.2 g (56.7 mmol) of CDI was added in portions. After stirring the solution for 90 min at rt, 6.8 g (90.5 mmol) of H$_2$N(CH$_2$)$_2$OMe was added and the mixture was stirred for an additional 10 hr. The mixture was partitioned between 200 mL water and 200 mL EtOAc. The organic phase was dried over Na$_2$SO$_4$ and removal of solvent resulted in a dark brown oil. Flash chromatography on silica gel (EtOAc/Hexane 30/70) yielded 5.0 g (21%) of an almost colorless oil. $^1$H NMR (300 MHz, CDCl$_3$) δ 12.30 (1H, s), 7.35 (1H, d, J=8.3 Hz), 7.10 (1H, d, J=1.5 Hz), 6.97 (1H, dd, J=8.3 and 1.5 Hz), 6.67 (1H, bs), 5.44 (1H, s), 3.69-3.35 (8H, m), 3.40 (3H, s) and 1.28-1.20 ppm (6H, m).

The protected aldehyde (5.0 g/16.8 mmol) was dissolved in 100 mL ethanol. 40 mL water and 1 mL 12 N HCl was added. The solvent was removed completely after 30 minutes, which yielded the aldehyde as a reddish/beige solid (3.6 g). The crude aldehyde was dissolved in 60 mL CH$_2$Cl$_2$, followed by the addition of 10 g (111 mmol) trioxane and 10 g CuSO$_4$. With vigorous stirring, 1.3 mL conc. H$_2$SO$_4$ was added dropwise. After 30 min, the product mixture was filtered through silica gel, which was further washed with 300 mL EtOAc. The combined organic solution was washed with 30 mL 1 M NaOH and dried over Na$_2$SO$_4$. Removal of solvent followed by flash chromatography on silica gel (EtOAc/Hexane 40/60→60/40) yielded 1.7 g (43%) of colorless crystals with the following properties: MP=71-73° C. $^1$H NMR (300 MHz, CDCl$_3$) δ 10.01 (1H, s), 8.12 (1H, d, J=8.1 Hz), 7.61 (1H, dd, J=8.1 and 1.5 Hz), 7.46 (1H, d, J=1.5 Hz), 5.31 (2H, s), 3.76 (2H, t, J=4.8 Hz), 3.60 (2H, t, J=4.8 Hz) and 3.36 ppm (3H, s).

To 500 mg (20.6 mmol) magnesium in 10 mL THF under a nitrogen atmosphere was added a crystal of I$_2$, 0.2 mL 1,2-dibromoethane and 1 mL of a solution of 2.45 g (15 mmol) bromocyclohexane in 10 mL THF. The remainder of the bromocyclohaxane solution was added portionwise within 5 min after the Grignard reaction started. The reaction mixture was kept at room temperature and stirred for 45 min, after which time some magnesium salts precipitated. The supernatant solution was added to a solution of the intermediate aldehyde (1.7 g; 7.22 mmol) in 20 mL THF. A yellow solution resulted, which was stirred for an additional 5 min. Twenty mL water was added slowly followed by 200 mL EtOAc and a small amount of HCl (enough to dissolve the magnesium salts). The organic phase was dried over Na$_2$SO$_4$ and concentrated to yield a yellow oil. Flash chromatography on silica gel (acetone/toluene 20/80) yielded 1.3 g (56%) of a slightly yellowish oil (which crystallized after several days) with the following properties: MP=78-79° C. IR; 3431, 2926, 2852, 1657, 1620, 1438, 1117, 780 cm$^{-1}$. $^1$H NMR (300 MHz, CDCl$_3$) δ 7.85 (1H, d, J=7.8 Hz), 7.00 (1H, dd, J=7.8 and 1.5 Hz), 6.91 (1H, d, J=1.5 Hz), 5.24 (2H, s), 4.39 (1H, d, J=6.6 Hz), 3.74-3.68 (2H, m), 3.58 (2H, t, J=4.8 Hz), 3.35 (3H, s), 2.28 (1H, bs), 1.94-0.90 ppm (11H, m).

The intermediate alcohol (1.0 g/3.1 mmol) was dissolved in 50 mL CH$_2$Cl$_2$ to which was added 1.6 g (7.4 mmol) PCC. After 50 of stirring, the mixture was filtered through 3 cm silica gel, which was washed with a mixture of 175 mL EtOAc/75 mL hexane. Concentration and flash chromatography on silica gel (EtOAc/hexane 40/60→50/50) yielded 700 mg (70%) of a colorless oil with the following properties: IR: 2930, 2854, 1677, 1449, 1427, 1314, 986 cm$^{-1}$. $^1$H NMR (300 MHz, CDCl$_3$) δ 8.03 (1H, d, J=7.8 Hz), 7.62 (1H, dd, J=7.8 and 1.5 Hz), 7.49 (1H, d, J=1.5 Hz), 5.28 (2H, s), 3.75 (2H, t, J=5.0 Hz), 3.59 (2H, t, J=5.0 Hz), 3.35 (3H, s), 3.27-3.15 (1H, m) and 1.95-1.25 ppm (10H, m).

EXAMPLE 36

Preparation of 7-(cyclopentylcarbonyl)-3-ethyl-2H-benzo[e]1,3-oxazaperhydroin-4-one

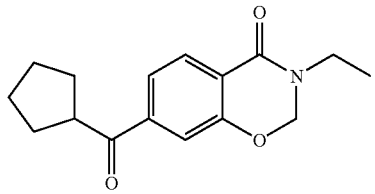

The synthesis was performed essentially as for Example 35 with the following exceptions: substitution of ethylamine for 2-methoxyethylamine and bromocyclopentane for bromocyclohexane. Flash chromatography on silica gel (EtOAc/hexane 40/60) yielded a colorless oil, which was crystallized from MTBE/hexane to yield white crystals with the following properties: MP=53-54° C. IR: 1677, 1664, 1491, 1427, 1316 cm$^{-1}$. NMR (300 MHz, CDCl$_3$) δ 8.04 (1H, d, J=8.3 Hz), 7.66 (1H, dd, J=8.3 and 1.5 Hz), 7.53 (1H, d, J=1.5 Hz), 5.23 (2H, s), 3.72-3.58 (1H, m), 3.62 (2H, q, J=7.2 Hz), 1.98-1.60 (8H, m) and 1.26 ppm (3H, t, J=7.2 Hz).

EXAMPLE 37

Preparation of 3-ethyl-7-(perhydro-2H-pyran-4-yl-carbonyl)-2H-benzo[e]1,3-oxazaperhydroin-4-one

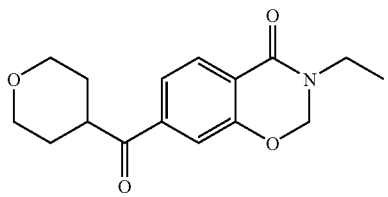

The synthesis was performed essentially as for Example 36 except for substitution of 4-chlorotetrahydropyrane for bromocyclopentane. MP=93-94° C. IR: 1682, 1663, 1430, 1311 cm$^{-1}$. $^1$H NMR (300 MHz, CDCl$_3$) δ 8.06 (1H, d, J=8.1 Hz), 7.63 (1H, dd, J=8.1 and 1.5 Hz), 7.50 (1H, d, J=1.5 Hz), 5.23 (2H, s), 4.10-4.00 (2H, m), 3.62 (2H, q, J=7.2 Hz), 3.60-3.38 (3H, m), 1.94-1.73 (4H, m) and 1.26 ppm (3H, t, J=7.2 Hz).

EXAMPLE 38

Preparation of 7-(cyclohexylcarbonyl)-3-ethyl-2H-benzo[e]1,3-oxazaperhydroin-4-one

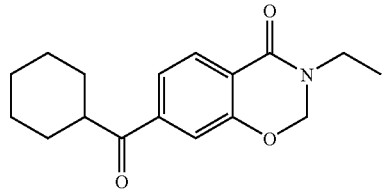

The synthesis was performed essentially as for Example 36 except for substitution of bromocyclohexane for bromocyclopentane. Crystallization from EtOAc/hexane provided white crystals with the following properties: MP=69-70° C. IR: 2932, 1678, 1667, 1427, 1316 cm$^{-1}$. $^1$H NMR (300 MHz, CDCl$_3$) δ 8.04 (1H, d, J=8.1 Hz), 7.63 (1H, dd J=8.1 and 1.8 Hz), 7.49 (1H, d, J=1.8 Hz), 5.22 (2H, s), 3.62 (2H, q, J=7.2 Hz), 3.25-3.14 (1H, m), 1.94-1.25 (10H, m) and 1.26 ppm (3H, t, J=7.2 Hz).

EXAMPLE 39

Preparation of 7-(2-cyclohexylacetyl)-3-ethyl-2H-benzo[e]1,3-oxazaperhydroin-4-one

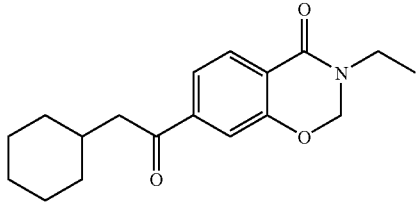

The synthesis was performed essentially as for Example 36 except for substitution of bromomethylcyclohexane for bromocyclopentane. Crystallization from MTBE/hexane yielded white crystals with the following properties: MP=55-58° C. IR: 2924, 2851, 1670, 1667, 1428, 1317, 894 cm$^{-1}$. $^1$H NMR (300 MHz, CDCl$_3$) δ 8.04 (1H, d, J=8.1 Hz), 7.63 (1H, dd J=8.1 and 1.5 Hz), 7.50 (1H, d, J=1.5 Hz), 5.22 (2H, s), 3.62 (2H, q, J=7.5 Hz), 2.80 (2H, d, J=6.6 Hz), 2.03-1.88 (1H, m), 1.80-0.92 (10H, m) and 1.26 ppm (3H, t, J=7.5 Hz).

EXAMPLE 40

Preparation of (R,S), (R,S)-3-ethyl-7-[(2-hydroxycyclohexyl)carbonyl]-2H-benzo[e]1,3-oxazaperhydroin-4-one

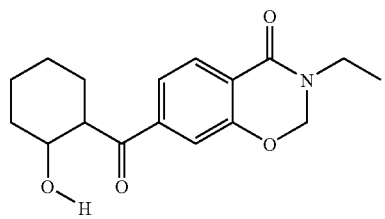

The intermediate aldehyde was synthesized as in Example 36. To 1.2 g (5.85 mmol) aldehyde in 40 mL ethanol was added a solution of 1.04 g (15 mmol) H$_2$NOH*HCl and 1.59 g Na$_2$CO$_3$ (15 mmol) in 50 mL water. The solution was stirred for 30 min at rt and the white precipitate that formed was redissolved by heating the solution to 50° C. After an additional 30 min at rt, the aqueous ethanol was removed by evaporation and 50 mL water was added. The mixture was extracted with 1×200 mL and 1×100 mL EtOAc. The organic phase was dried over $Na_2SO_4$ and the evaporation of the solvent yielded the oxime as a slightly yellow solid.

The oxime (1.2 g; 5.45 mmol) was dissolved in 30 mL DMF to which was added 800 mg (6.0 mmol) NCS and 30 mL HCl gas. The mixture was stirred for 60 min at rt until the starting material was consumed. The mixture was diluted with 300 mL EtOAc and extracted with 2×150 mL water. The organic phase was dried over $Na_2SO_4$, and the volume reduced to 100 mL. To this mixture were added 5 mL DMF, 25 mL cyclohexene and a solution of 1.5 mL $NEt_3$ in 25 mL $CH_2Cl_2$ (dropwise over night). The solvent was evaporated and 150 mL water was added. The mixture was extracted with 250 mL EtOAc and the organic phase was concentrated after drying over $Na_2SO_4$. Flash chromatography on silica gel (EtOAc/hexane 50/50) yielded a colorless oil (800 mg, 49%), which was crystallized from EtOAc/hexane. MP=102-104° C. IR: 2934, 1664, 1621, 1432, 1314, 838 $cm^{-1}$. $^1$H NMR (300 MHz, $CDCl_3$) δ 7.98 (1H, d, J=8.1 Hz), 7.42 (1H, dd J=8.1 and 1.5 Hz), 7.31 (1H, d, J=1.5 Hz), 5.21 (2H, s), 4.55-4.50 (1H, m), 3.61 (2H, q, J=6.9 Hz), 3.27-3.20 (1H, m), 2.31-1.20 (8H, m) and 1.25 ppm (3H, t, J=6.9 Hz).

To a solution of the isoxazoline from above (749 mg; 2.49 mmol) in 100 mL methanol was added 1.2 g $B(OH)_3$ in 70 mL water and 1 g Raney Nickel. After hydrogenation for 4 hr, the mixture was filtered and concentrated and partitioned between 50 mL brine and 200 mL EtOAc. The two phases were separated and the aqueous layer was extracted with an additional 200 mL EtOAc. The combined organic layers were dried over $Na_2SO_4$ and concentrated. Flash chromatography on silica gel with EtOAc/hexane (50/50) gave 522 mg (69%) of a colorless oil. Crystallization from EtOAc/hexane yielded 250 mg of a white solid with the following properties: MP=106-108° C. IR: 3460, 2933, 1661, 1431, 1319, 988 $cm^{-1}$. $^1$H NMR (300 MHz, $CDCl_3$) δ 8.06 (1H, d, J=8.1 Hz), 7.61 (1H, dd, J=8.1 and 1.5 Hz), 7.48 (1H, d, J=1.5 Hz), 5.23 (2H, s), 4.30-4.25 (1H, m), 3.62 (2H, q, J=7.2 Hz), 4.33-4.27 (1H, m), 2.05-1.35 (8H, m) and 1.26 ppm (3H, t, J=7.2 Hz).

EXAMPLE 41

Preparation of 7-(cyclohexylcarbonyl)-3-methyl-2H-benzo[e]1,3-oxazaperhydroin-4-one

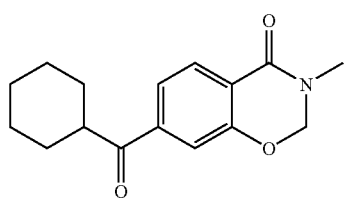

The synthesis was performed essentially as for Example 38 except for substitution of methylamine for ethylamine. MP=99-101° C. IR: 2934, 2855, 1676, 1665, 1574, 1497, 1426, 1350, 1263, 984 $cm^{-1}$. $^1$H NMR (300 MHz, $CDCl_3$) δ 8.04 (1H, d, J=8.1 Hz), 7.63 (1H, dd, J=8.1 and 1.5 Hz), 7.49 (1H, d, J=1.5 Hz), 5.21 (2H, s), 3.23-3.15 (1H, m), 3.15 (3H, s) and 1.93-1.20 ppm (10H, m).

EXAMPLE 42

Preparation of 7-(cyclohexylcarbonyl)-3-(methyl-ethyl)-2H-benzo[e]1,3-oxazaperhydroin-4-one

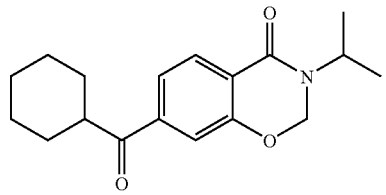

The synthesis was performed essentially as for Example 38 except for substitution of isopropylamine for ethylamine. Crystallization from MTBE/hexane yielded white crystals with the following properties: MP=88-90° C. IR: 2931, 2854, 1676, 1654, 1450, 1427, 1335, 1218, 991 $cm^{-1}$. $^1$H NMR (300 MHz, $CDCl_3$) δ 8.04 (1H, d, J=8.1 Hz), 7.62 (1H, dd, J=8.1 and 1.5 Hz), 7.49 (1H, d, J=1.5 Hz), 5.19 (2H, s), 4.96-4.82 (1H, m), 3.25-3.14 (1H, m), 1.95-1.20 (10H, m) and 1.26 ppm (6H, d, J=6.9 Hz).

EXAMPLE 43

Preparation of (R,S)-6-(cyclohexylcarbonyl)-3aH-benzo[e]pyrrolidino[2,1-b]1,3-oxazaperhydroin-9-one

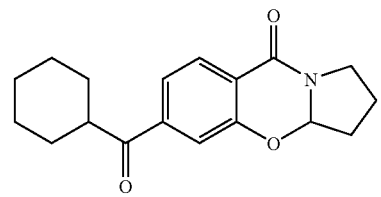

The synthesis was performed essentially as for Example 38 with the following exceptions: substitution of 4-aminobutyraldehyde for ethylamine yielded an oil which was treated with HBr/HOAc in methylene chloride to form the intermediate aldehyde. The final product had the following properties: MP=110-111° C. IR: 2927, 2855, 1676, 1665, 1439, 1078 $cm^{-1}$. $^1$H NMR (300 MHz, $CDCl_3$) δ 8.00 (1H, d, J=7.8 Hz), 7.63 (1H, dd, J=7.8 and 1.5 Hz), 7.50 (1H, d, J=1.5 Hz), 5.52 (1H, t, J=6.0 Hz), 3.91-3.82 (1H, m), 3.67-3.59 (1H, m), 3.23-3.13 (1H, m), 2.53-2.42 (1H, m),2.35-2.22 (1H, m), 2.20-2.07 (1H, m) and 2.05-1.20 ppm (12H, m).

EXAMPLE 44

Preparation of 6-(cyclohexylcarbonyl)-3-ethyl-2H-benzo[e]1,3-oxazaperhydroin-4-one

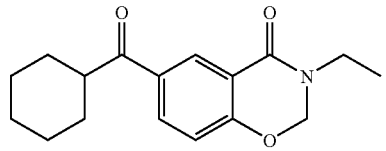

5-Formylsalicylic acid (2.8 g, 16.8 mmol) was dissolved in 150 mL methanol and 10 mL thionyl chloride was added dropwise. After stirring the solution for 18 hr at room temperature, another 5 mL thionyl chloride was added dropwise and the mixture was refluxed for 5 hr. The solvent was evaporated and the remaining mixture was filtered through silica gel, which was washed with 300 mL EtOAc/hexane (1:1). Concentration of appropriate fractions yielded 3.0 g orange solid, which was dissolved in 30 mL $CH_2Cl_2$. Ethylamine (5.0 g) was added and the solution was stirred for 3 days at rt. The solvent was evaporated and 100 mL aqueous HCl was added until the pH=1. The mixture was extracted with EtOAc (250 mL and 100 mL), dried over $Na_2SO_4$ and concentrated to yield 1.4 g yellow amide.

The crude amide was dissolved in 40 mL $CH_2Cl_2$ containing 6.0 g trioxane (67 mmol) and 5.0 g $CUSO_4$ The resulting mixture was stirred vigorously with the dropwise addition of 1.0 mL conc. $H_2SO_4$. After 30 minutes the mixture was filtered through silica gel, which was washed with 250 mL EtOAc. The organic phase was concentrated, which resulted in a beige solid. Flash chromatography on silica gel (EtOAc/hexane 50/50) yielded 550 mg of a colorless oil, which solidified after 1 hr. The intermediate aldehyde had the following properties: MP=47-50° C. $^1$H NMR (300 MHz, $CDCl_3$) δ 9.97 (1H, s), 8.47 (1H, d, J=1.8 Hz), 8.00 (1H, dd, J=8.4 and 1.8 Hz), 7.09 (1H, d, J=1.8 Hz), 5.28 (2H, s), 3.63 (2H, q, J=7.2 Hz) and 1.27 ppm (3H, t, J=7.2 Hz).

The conversion of the aldehyde to the cyclohexylketone was completed essentially following the procedure in example 38. IR: 2933, 2855, 1683, 1614, 1494, 1463, 1372, 1311, 1247, 1209, 978 $cm^{-1}$. $^1$H NMR (300 MHz, $CDCl_3$) δ 8.53 (1H, d, J=2.1 Hz), 8.09 (1H, dd, J=8.7 and 2.1 Hz), 7.03 (1H, d, J=8.7 Hz), 5.25 (2H, s), 3.63 (2H, q, J=7.2 Hz), 3.37-3.25 (1H, m), 1.92-1.20 (10H, m) and 1.27 ppm (3H, t, J=7.2 Hz).

EXAMPLE 45

Preparation of (3S)-3-benzyl-(R,S)-2H,3H,4H,7aH-pyrrolidino[2",1"-2',3']1,3-oxazaperhydroino[5',6'-5,4]benzo[f]1,4-oxazepine-5,11-dione

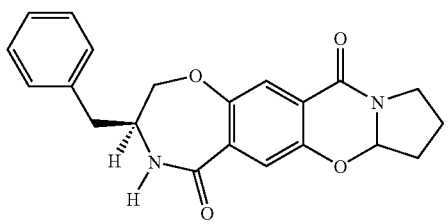

Commercially available carbonylbenzyloxyphenylalanine (10.0 g; 33.4 mmol) was dissolved in 150 mL $CH_2Cl_2$. CDI (8.0 g 49.3 mmol) was added and the mixture was stirred for 60 min at rt. Methanol (25 mL) was added and the mixture was stirred for another 60 min at rt. The solvent was evaporated, 150 mL water was added and the mixture was extracted with 250 mL EtOAc. The organic phase was dried over $Na_2SO_4$ and concentrated, which yielded a colorless oil (10.1 g).

The carbonylbenzyloxyphenylalanine methylester was dissolved in 120 mL THF and 1.2 g (55 mmol) $LiBH_4$ was added, causing the mixture to warm up to 60° C. The mixture was refluxed for 5 min until the starting material was consumed. The reaction was quenched by the slow addition of 25 mL 2 N HCl followed by 100 mL methanol. After the solution was concentrated, 100 mL brine was added and the mixture was extracted with 2×200 mL EtOAc/hexane (1:1). The organic phase was dried over $Na_2SO_4$ and concentrated, which yielded 9.1 g (31.9 mmol) of a white solid with the following properties: MP: 85-87° C. $^1$H NMR (300 MHz, $CDCl_3$) δ 7.35-7.15 (10H, m), 5.07 (2H, s), 5.02-4.93 (1H, m), 4.00-3.89 (1H, m), 3.74-3.54 (2H, m) and 2.86 ppm (2H, d, J=6.9 Hz).

The alcohol from above was dissolved in 80 mL pyridine followed by 400 mg DMAP and 4.6 g (40.1 mmol) $CH_3SO_2Cl$ at 0° C. After the mixture was stirred for 18 hr at rt, 700 mL EtOAc was added and the solution was extracted with 3×200 mL 2N HCl. The organic phase was dried over $Na_2SO_4$ and concentrated, which yielded 9.7 g of a beige solid with the following properties: MP: 82-85° C. $^1$H NMR (300 MHz, $CDCl_3$) δ 7.35-7.18 (10H, m), 5.08 (2H, s), 5.00-4.94 (1H, m), 4.29-4.10 (3H, m), 2.96 (3H, s) and 2.95-2.84 ppm (2H, m).

To a solution of 1.5 g (5.4 mmol) of the phenol (synthesized as in Example 30) in 100 mL toluene were added 2.0 g $K_2CO_3$ and 1.0 g of the methylsulfonate. The mixture was refluxed for 7 hours, then 2.0 g $K_2CO_3$ and 2.5 g of the methylsulfonate were added. The mixture was refluxed for 18 hr, then 2.0 g $K_2CO_3$ and 5.0 g of the methylsulfonate were added and the mixture refluxed another 24 hr. Water (100 mL) was added and the mixture was extracted with EtOAc (250 mL and 150 mL). The organic phase was dried over $Na_2SO_4$, and the solvent evaporated. Flash chromatography on silica gel (EtOAc/hexane 45/55, then 66/34) yielded 1.6 g of a slightly yellowish oil with the following properties: $^1$H NMR (300 MHz, $CDCl_3$) δ 7.44-7.18 (12H, m), 5.88-5.80 (1H, m), 5.46 (0.5H, t, J=6 Hz), 5.44 (0.5H, t, J=6 Hz), 5.10 (2H, s), 4.39 (2H, q, J=6.9 Hz), 4.29-4.00 (2H, m), 3.96-3.77 (2H, m), 3.65-3.56 (1H, m), 3.13-2.96 (2H, m), 2.50-2.37 (1H, m), 2.30-1.86 (3H, m) and 1.38 ppm (3H, t, J=6.9 Hz).

This oil was dissolved in 100 mL methanol. Pd/C (600 mg) was added and the mixture was hydrogenated for 2 hr. The mixture was filtered and the solvent evaporated. The resulting oil was heated to 150° C. for 5 min. Flash chromatography of the resulting oil on silica gel (EtOAc/hexane 85/15) yielded a yellowish oil (250 mg). Crystallization from EtOAc/MTBE yielded 175 mg white crystals with the following properties: MP=159-162° C. IR: 1670, 1442 $cm^{-1}$. $^1$H NMR (300 MHz, $CDCl_3$) δ 7.64-7.13 (7H, m), 6.28-6.20 (1H, m), 5.46 (1H, t, J=6 Hz), 4.29-4.14 (2H, m), 3.90-3.77 (2H, m), 3.66-3.58 (1H, m), 2.96-2.76 (2H, m), 2.50-2.39 (1H, m), 2.31-2.06 (2H, m) and 2.03-1.87 ppm (1H, m).

EXAMPLE 46

Preparation of (R,S), (R,S)-2H,3H,3aH,9aH--1,2-oxazolidino[3,2-b]pyrrolidino[2",1"-3',2'](1,3-oxazino)[5',6'-5,4]benzo[e]1,3-oxazaperhydroine-6,12-dione

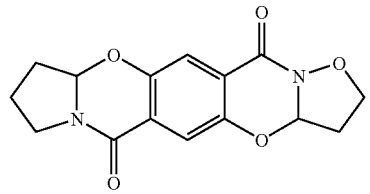

To a solution of N-hydroxyphthalimide (7.5 g, 44.6 mmol) in 200 mL DMF that was sparged with argon gas was added 2.14 g of 60% sodium hydride (53.5 mmol) in portions over a period of 1 hr. The resulting solution was heated to 80° C. for 3 hr and then cooled to room temperature. To this solution was added chloropropionaldehyde diethyl acetal 11.2 mL, 66.9 mmol) and sodium iodide (10.0 g, 66.9 mmol). The resulting suspension was heated to 80° C. for 4 hr. The solution was cooled to room temperature and then partitioned between 1.5 L H$_2$O/0.5 L Et$_2$O. The organic layer was washed with brine, dried over Na$_2$SO$_4$, filtered and evaporated in vacuo. Flash chromatography of the residue (EtOAc:hexanes 1:4) afforded 9.3 g (71%) of a white solid. The intermediate was dissolved in 250 mL of anhydrous ethyl alcohol, to which was added anhydrous hydrazine (1.99 mL, 63.4 mmol). Immediate precipitation of a fluffy white solid was noted. After 2 hr the mixture was filtered to remove the precipitated material, which was washed with ethyl alcohol. The combined ethyl alcohol solutions were evaporated in vacuo and the resulting residue partitioned between CH$_2$Cl$_2$/H$_2$O. The organic layer was washed with brine, dried over Na$_2$SO$_4$, filtered and evaporated in vacuo. The resulting oil was distilled under vacuum (2 mm Hg, 65° C.) to afford 3.25 g (63%) of the intermediate amine. IR: 2974, 2930, 2876, 1126 and 1059 cm$^{-1}$. $^1$H NMR (500 MHz) δ 5.37 (2H, s), 4.63 (1H, t, J=6.0 Hz), 3.74 (2H, t, J=6.5 Hz), 3.65 (2H, m), 3.51 (2H, m), 1.91 (2H, q, J=6.2 Hz) and 1.21 ppm (6H, t, J=7.1 Hz).

Argon was bubbled into a solution of 7.5 g (27 mmol) ethyl 7-hydroxy-9-oxo-3aH-benzo[e]pyrrolidino[2,1-b]1,3-oxazine-6-carboxylate (compound of Example 7) in 75 mL of 1:1 MeOH:1 M NaOH. The resulting solution was stirred overnight and MeOH was then removed in vacuo. The pH of the bright yellow solution was adjusted to 4.0 with concentrated hydrochloric acid. The heavy white precipitate was collected on a Buchner funnel and washed with small portions of water, yielding 6.6 g of the intermediate salicylic acid (98%) after drying for several hours at 0.2 mm Hg.

To a suspension of the intermediate salicylic acid (400 mg, 1.59 mmol) in 10 mL dry DMF was added 1,1'-carbonyldiimidazole (257 mg, 1.59 mmol). The reaction mixture became homogeneous after 5 min. After stirring at room temperature for 18 hr, the amine (0.45 mL, 2.7 mmol) was added to the solution. The reaction was then stirred for 1 hr at room temperature and then washed with EtOAc/H$_2$O. The organic layer was washed with five 50-mL portions of EtOAc. The combined organic phases ere washed with 1 N HCl, saturated NaHCO$_3$ and brine, dried over Na$_2$SO$_4$, filtered and concentrated in vacuo. After drying on at reduced pressure for 1 hr, flash chromatography of the residue (EtOAc:hexanes, 1:1) afforded pure material. This intermediate was dissolved in 5 mL CH$_2$Cl$_2$ and treated with 3 drops H$_2$SO$_4$ and stirred at room temperature for 2 hr. The reaction mixture was then washed with saturated NaHCO$_3$, dried over Na$_2$SO$_4$, filtered and evacuated in vacuo. The solid was crystallized from CH$_2$Cl$_2$/Et$_2$O to afford 240 mg (32%) of an off-white powder. MP: 245-250° C. IR: 1666 and 1458 cm$^{-1}$. $^1$H NMR (500 MHz) δ 7.58 (0.5H, s), 7.56 (0.5H, s), 7.54 (0.5H, s), 7.52 (0.5H, m), 5.76 (1H, m), 5.47 (1H, q, J=5.7 Hz), 4.31 (1H, m), 4.24 (1H, m), 3.85 (1H, m), 3.62 (1H, m), 2.80 (1H, m), 2.71 (1H, m), 2.45 (1H, m), 2.27 (1H, m), 2.14 (1H, m) and 1.96 ppm (1H, m).

EXAMPLE 47

Preparation of (R,S), (R,S)-6-[(2-ethoxypyrrolidinyl) carbonyl]-7-hydroxy-3aH-benzo[e]pyrrolidino[2,1-b]1,3-oxazaperhydroin-9one

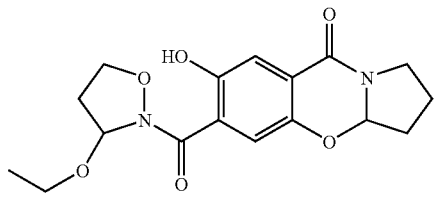

To a suspension of the intermediate salicylic acid (see Example 46) (411 mg, 1.65 mmol) in 10 mL dry DMF was added 1,1'-carbonyldiimidazole (267 mg, 1.65 mmol). Immediately, the reaction mixture became homogeneous. After stirring at room temperature for 16 h, O-3,3-diethoxypropyl hydroxylamine (344 μL, 2.06 mmol) was added to the solution. After 1 h, the reaction was washed with 1 N HCl, saturated NaHCO$_3$ and brine, dried over Na$_2$SO$_4$, filtered and concentrated in vacuo. The intermediate was dissolved in 15 mL dry CH$_2$Cl$_2$ and treated with camphorsulfonic acid (100 mg, 0.430 mmol). After 0.5 hr, the reaction was washed with saturated NaHCO$_3$, dried over Na$_2$SO$_4$, filtered and concentrated. Flash chromatography of the oily residue (CH$_2$Cl$_2$:MeOH, 50:1) afforded 220 mg (38%) of a yellow solid. MP: 138-140° C. IR: 1667 and 1451cm$^{-1}$. $^1$H NMR (500 MHz) δ 10.83 (0.5H, s), 10.79 (0.5H, s), 7.78 (0.5H, s), 7.76 (0.5H, s), 7.52 (0.5H, s), 7.50 (0.5H, m), 6.02 (1H, m), 5.46 (1H, m), 4.34 (1H, m), 3.99 (0.5H, m), 3.93 (0.5H, m), 3.84 (1H, m), 3.78(1H, m), 3.70 (1H, m), 3.63 (1H, m), 2.51 (1H, m), 2.43 (1H, m), 2.38 (1H, m), 2.23 (1H, m), 2.12 (1H, m), 1.93 (1H, m) and 1.25 ppm (3H, m).

EXAMPLE 48

Preparation of (R,S), (R,S)-6-[(3-hydroxypyrrolidinyl)carbonyl]-3aH-benzo[e]pyrrolidino[2,1-b]1,3-oxazaperhydroin-9-one

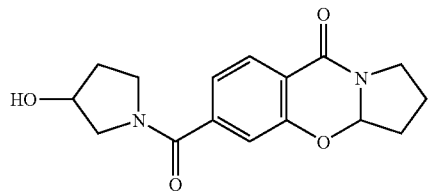

A solution of 3-hydroxypyrrolidine (1.0 g, 11.5 mmol) and imidazole (1.72 g, 25.2 mmol) in 20 mL CH$_2$Cl$_2$ was prepared in a 3-neck 100 mL flask fitted with a thermometer and subsequently cooled to 0° C. A solution of t-butyldimethylsilyl chloride (3.80 g, 25.2 mmol) in 15 mL CH$_2$Cl$_2$ was added via a syringe pump over a period of 1 hr. The solution was stirred at room temperature, noting the slow precipitation of a white solid (imidazole hydrochloride). After 18 hr the precipitate was filtered off and washed with CH$_2$Cl$_2$. The solution was then concentrated in vacuo and the resulting orange oil was redissolved in methanol. After stirring the alcoholic solution for 2 hr, the solution was again evaporated in vacuo and then partitioned between $CH_2Cl_2/H_2O$. The organic layer was washed with brine, dried over $Na_2SO_4$, filtered and concentrated. The residue was dried under vacuum for several hours affording 1.9 g (83%) of 3-hydroxy-pyrrolidine t-butyl-dimethylsilylether as a viscous orange oil. IR: 3150, 2953, 2928, 2888, 1413 and 1255 cm$^{-1}$.

To a suspension of the intermediate salicylic acid (see Example 46 for its synthesis) (430 mg, 1.84 mmol) in 10 mL dry $CH_2Cl_2$ was added 1,1'-carbonyldiimidazole (373 mg, 2.30 mmol). The reaction mixture became homogeneous very slowly and $CO_2$ gas evolution was also slow. After 1 h at room temperature, a solution of the 3-hydroxypyrrolidine t-butyl-dimethylsilylether (556 mg, 2.76 mmol) in 3 mL $CH_2Cl_2$ was added. After 16 hr at room temperature, the reaction mixture was concentrated in vacuo. The residue was partitioned between EtOAc/1 N HCl and the organic layer was washed with saturated $NaHCO_3$, brine, dried over $Na_2SO_4$, filtered and concentrated in vacuo. Flash chromatography of the crude solid (EtOAc:hexanes 1:1-1.5) afforded 648 mg (84%) of silyl ether as a pure oil. IR: 1671, 1630 and 1434 cm$^{-1}$.

To a solution of the silyl ether (598 mg, 1.43 mmol) in 10 mL THF was added tetraethylammonium fluoride hydrate (321 mg, 2.15 mmol). After 1 hr the reaction was evaporated in vacuo and the resulting residue was partitioned between $CH_2Cl_2/H_2O$. The organic layer was washed with brine, dried over $Na_2SO_4$, filtered and concentrated in vacuo. Flash chromatography of the residue ($CH_2Cl_2$:MeOH, 30:1) afforded 323 mg (75%) of the product alcohol as a white solid. MP: 187-188° C. IR: 3400, 1668, 1620 and 1430 cm$^{-1}$. $^1$H NMR: 7.98 (1H, m), 7.20 (1H, m), 7.10 (1H, m), 5.50 (1H, m), 4.60 (0.5H, s), 4.47 (0.5H, s), 3.86-3.38 (7H, m), 2.45 (1H, m), 2.27 (1H, m) and 2.15-1.92 ppm (4H, m).

EXAMPLE 49

Preparation of (R,S), (R,S)-2-methyl-13aH,7aH-piperazino[2,1-b]pyrrolidino[2″,1″-3',2'](1,3-oxaza-perhydroino)[5',6'-5,4]benzo[e]1,3-oxazine-3,5,11-trione

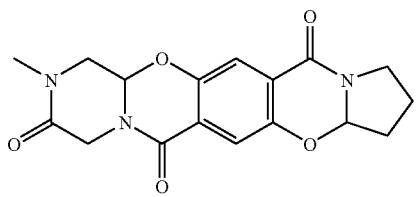

A neat mixture of the ethyl salicylate (Example 7) (632 mg, 2.28 mmol) and N-2,2-dimethoxy-methyl-N-methylglycina-mide (2.0 g, 11.3 mmol) was heated to 130° C. The mixture formed a homogeneous melt which was heated for 10 min. The residue was chromatographed (EtOAc) and the intermediate was dissolved in 20 mL $CH_2Cl_2$ and treated with 6 drops conc. $H_2SO_4$. After 6 hr the reaction was neutralized with saturated $NaHCO_3$, extracted with $CH_2Cl_2$, dried over $Na_2SO_4$, filtered and evaporated. Flash chromatography of the residue (EtOAc) afforded 325 mg (42%) of white solid. MP: 253-256° C. IR: 1660 and 1459 cm$^{-1}$. $^1$H NMR (500 MHz) δ 7.57 (0.5H, s), 7.56 (0.5H, s), 7.56 (0.5H, s), 7.54 (0.5H, m), 5.57 (1H, dd, J=4.2/6.8 Hz), 5.48 (1H, q, J=6.1 Hz), 445 (1H, dd, J=6.1/17 Hz), 4.26 (1H, d, J=17 Hz), 4.23 (1H, d, J=17 Hz), 3.86(2H, m), 3.76 (1H, m), 3.62 (1H, m), 3.10 (1.5H, s), 3.10 (1.5H, s), 2.45 (1H, m), 2.27 (1H, m), 2.14 (1H, m) and 1.96 ppm (1H, m).

EXAMPLE 50

Preparation of (R,S), (R,S)-5-nitro-3aH,9aH-pyrroli-dino[2,1-b]pyrrolidino[2″,1″-3',2'](1,3-oxazaperhy-droino)[5',6'-2,1]benzo[4,5-e]1,3-oxazine-6,12-dione

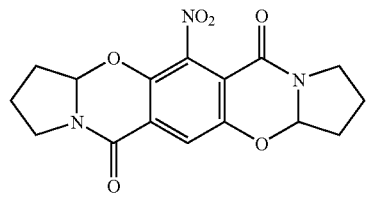

Method A:

To 300 mg (1 mmol) (R,S), (R,S)-3aH,9aH-pyrrolidino[2,1-b]pyrrolidino[2″,1″-2',3'](1,3-oxazino)[5',6'-2,1]benzo[4,5-e]1,3-oxazaperhydroine-6,12-dione (the product from Example 1) in 30 mL of acetic anhydride was added 3.5 mL (43 mmol) 90% nitric acid, dropwise over 10 min at room temperature. After 30 min the reaction mixture was partitioned between 100 mL of $CH_2Cl_2$ and 200 mL of saturated aqueous $NaHCO_3$. The aqueous phase was extracted with 3×100 mL of $CH_2Cl_2$ and the combined organic layers were dried with $MgSO_4$. Concentration of the solution in vacuo produced 408 mg of brown foam after 4 hr under vacuum at 0.1 mm Hg. Chromatography on 200 g of silica (eluting with EtOAc) gave 220 mg of product, which was resolved into two spots with similar Rf values in TLC experiments using EtOAc. LC/MS analysis (C-18) showed two peaks containing 95.5% of the material: 346 (M+1). IR: 1778, 1548, 1463 and 1426 cm$^{-1}$.

Method B:

To 900 mg (3.0 mmol) of the product from Example 1 in 20 mL of 0° C. $H_2SO_4$ was added dropwise over 10 min, 2 mL of 90% $HNO_3$. After 30 min, the reaction mixture was poured into 200 mL of cold water and the organic products were extracted with 3×50 mL $CH_2Cl_2$. The combined organic layers were washed with 100 mL of water and dried over $MgSO_4$. Solvent was removed in vacuo to give 1.1 g of 5-nitro-3aH,9aH-pyrrolidino[2,1-b]pyrrolidino[2″,1″-3',2'] (1,3-oxazaperhydroino)[5',6'-2,1]benzo[4,5-e]1,3-oxazine-6,12-dionic.

This sulfuric acid based nitration gives a nitration product consisting mostly of the less mobile TLC spot, i.e. the more polar two, of the four possible diastereomers. The process above was repeated with 800 mg (2.7 mmol) starting material to give an additional 1.0 g of product. The combined crude nitro compound (2.1 g) was filtered through 40 g of silica gel in 50 mL of EtOAc, followed by 300 mL of EtOAc to yield 1.9 g of colorless material that produced a foam when taken to dryness. Crystallization from the minimum volume of EtOAc gave 450 mg of purified, more polar isomer (86%) as judged by NMR. The mother liquor gave the less polar isomer (2:1) as a colorless solid upon standing overnight.

EXAMPLE 51

Preparation of (R,S), (R,S)-5-amino-3aH,9aH-pyrrolidino[2,1-b]pyrrolidino[2",1"-3',2'](1,3-oxazino)[5',6'-4,5]benzo[e]1,3-oxazaperhydroine-6,12-dione

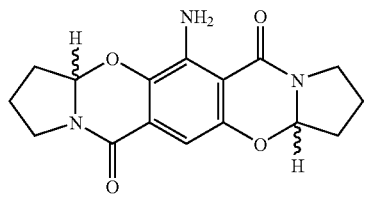

To 400 mg (1.15 mmol) of (R,S), (R,S)-5-nitro-3aH,9aH-pyrrolidino[2,1-b]pyrrolidino[2",1"-3',2'](1,3-oxazaperhydroino)[5',6'-2,1]benzo[4,5-e]1,3-oxazine-6,12-dione (the product from Example 50, Method A) in 40 mL of EtOAc, was added 200 mg of 10% Pd/C, while sparging with argon. The resulting suspension was treated with hydrogen at 50-60 psi overnight in a Parr hydrogenator. The catalyst was removed by vacuum filtration with the aid of celite and the filtrate was concentrated to a solid in vacuo. Silica gel chromatography on the residue with 25% EtOAc in $CH_2Cl_2$ gave 253 mg (70% yield) of a colorless solid with the following properties: IR: 3447, 3333, 1670, 1654, 1595, 1431, 1388, 1341, 1079 and 775 $cm^{-1}$. $^1H$ NMR (300 MHz, $CDCl_3$) δ 6.73 (1H, s), 6.72 (1H, s), 6.04 (2H, br s), 5.46 (1H, t, J=6.0 Hz), 5.38 (1H, t, J=6.0), 3.81 (2H, m), 3.58 (2H, m), 2.43 (2H, m), 2.29 (2H, m) 2.15 (2H, m) and 1.94 ppm (2H, m).

EXAMPLE 52

Preparation of (R,S), (R,S)-5-amino-3aH,9aH-pyrrolidino[2,1-b]pyrrolidino[2",1"-3',2'](1,3-oxazino)[5',6'-4,5]benzo[e]1,3-oxazaperhydroine-6,12-dione

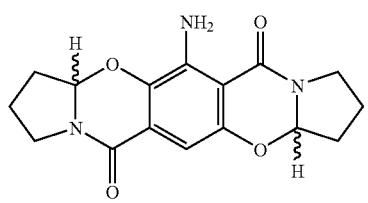

To 450 mg (1.30 mmol) of the product from Example 50, Method B in 80 mL $CH_2Cl_2$, was added 180 mg 10% Pd/C, under argon. The resulting suspension was hydrogenated overnight at 50-60 psi in a Parr hydrogenator. The catalyst was removed by filtering through a pad of celite and the solution concentrated to yield 470 mg crude product. Silica gel chromatography using 25% EtOAc in $CH_2Cl_2$ yielded 380 mg (93%) as a colorless solid with the following properties. IR: 3470, 3329, 1673, 1650, 1592, 1542, 1429, 1388, 1340, 1224, 1098, 1079 and 775 $cm^{-1}$. $^1H$ NMR (300 MHz, $CDCl_3$) d 6.72 (1H, s), 6.05 (2H, br s), 5.46 (1H, t, J=6.0 Hz), 5.38 (1H, t, J=6.0 Hz), 3.80 (2H, m), 3.61 (2H, m), 2.42 (2H, m), 2.23 (2H, m), 2.10 (2H, m) and 1.96 ppm (2H, m).

EXAMPLE 53

Preparation of (R,S), (R,S)-5-amino-11-bromo-3aH,9aH-pyrrolidino[2,1-b]pyrrolidino[2",1"-3',2'](1,3-oxazino)[5',6'-4,5]benzo[e]1,3-oxazaperhydroine-6,12-dione

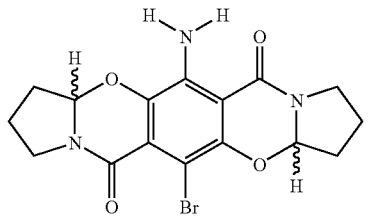

To 450 mg (1.5 mmol) of the product from Example 50 in 60 mL of EtOAc was added 200 mg Pd/C under argon and the resulting suspension was hydrogenated in a Parr hydrogenator for 18 h at 50-60 psi. The reaction mixture was filtered, and the solvent removed in vacuo to yield 212 mg (0.67 mmol, 45%) of the aniline intermediate as a crystalline yellow solid. Thin layer chromatography (EtOAc) indicates a complete conversion. NMR indicates (1:1:1:1) mixture of diastereomers. LC-MS analysis indicates 98.2% purity by total ion current with (M+H)=315.9 as the dominant peak and consistent with structure.

The aniline was dissolved in 25 mL of $CH_2Cl_2$ (anhydrous) and 450 mg (2.8 mmol) of $Br_2$ was added at 0° C. under argon atmosphere. The first drop of $Br_2$ instantly decolorized. After 15 min at 0-5° C. the reaction mixture was diluted to 50 mL with $CH_2Cl_2$. The organic phase was washed with 20 mL 10% aqueous sodium bisulfite and 30 mL saturated aqueous $NaHCO_3$, dried over $Na_2SO_4$ and concentrated in vacuo to yield 240 mg (91%) of a pale green solid, which had the following properties: IR: 3473, 3333, 2977, 2883, 1652, 1591, 1527, 1451, and 1386 $cm^{-1}$. 1H NMR (300 MHz, $CDCl_3$) δ 6.1 (2H, br s), 3.94 (1H, m), 3.83 (1H, m), 3.53 (2H, m), 2.42 (2H, m), 2.28 (2H, m), 2.11 (2H, m) and 1.99 ppm (2H, m).

EXAMPLE 54

Preparation of (R,S), (R,S)-N-(6,12-dioxo-3aH,9aH-pyrrolidino[2,1-b]pyrrolidino[2",1"-3',2'](1,3-oxazino)[5',6'-4,5]benzo[e]1,3-oxazaperhydroin-5-yl)acetamide

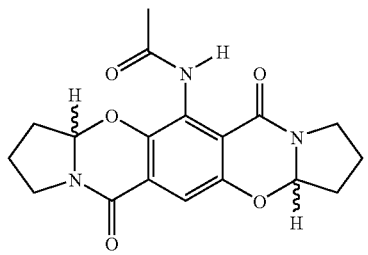

To 850 mg of the aniline (intermediate of Example 53) in 20 mL of $Ac_2O$ was added 1 drop of $H_2SO_4$. After 1 hr the reaction mixture was stirred with 50 mL ice water. Solids formed were recovered by filtration, washed with several small portions of water and air dried to give 700 mg of crude acetamide. This crude material was crystallized from 10% EtOH in EtOAc to yield 400 mg of a colorless solid (1:1 isomeric composition by LC-MS), with the following properties: IR: 3279, 2983, 1651, 1464, 1428, 1391, 1246, 1080 and 777 cm$^{-1}$. $^1$H NMR (300 MHz, CDCl$_3$) δ 9.76 (0.5H, s), 9.67 (0.5H, s), 7.40 (0.5H, s), 7.38 (0.5H, s), 5.63 (0.5H, t, J=60 Hz), 5.46 (1H, m), 5.40 (0.5H, t, J=6.0 Hz), 3.84 (2H, m), 3.60 (2H, m), 2.41 (2H, m), 2.22 (2H, m), 2.20 (3H, s), 2.15 (2H, m) and 1.96 ppm (2H, m).

The mother liquor from the ethyl acetate crystallization was concentrated in vacuo and the residue was chromatographed on 100 g silica gel with 10% EtOH in EtOAc to yield 160 mg of the more mobile isomer. This material had the following properties: Purity: 98.8% with isomeric composition of 50:1 by C-18 LC/MS; (M+H)=357.9. IR: 3272, 1656, 1466, 1421, 1367, 1243, 1080 and 779 cm$^{-1}$. $^1$H NMR (300 MHz, CDCl$_3$) δ 9.76 (1H, s), 7.38 (1H, s), 5.63 (1H, t, J=5.4 Hz), 5.46 (1H, t, J=6.0 Hz), 3.86 (2H, m), 3.60 (2H, m), 2.46 (2H, m), 2.27 (2H, m), 2.20 (3H, s), 2.05 (2H, m) and 1.91 ppm (2H, m).

EXAMPLE 55

Preparation of (R,S), (R,S)-N-(11-chloro-6,12-dioxo-3aH,9aH-pyrrolidino[2,1-b]pyrrolidino[2",1"-3',2'](1,3-oxazino)[5',6'-4,5]benzo[e]1,3-oxazaperhydroin-5-yl)acetamide

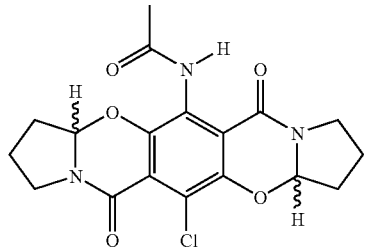

Into a solution of 250 mg (0.70 mmol) of the product from Example 54 in 50 mL of CH$_2$Cl$_2$ was bubbled Cl$_2$ from a lecture bottle for 2 sec. The reaction mixture was washed with 50 mL 20% aqueous NaHSO$_3$ and 50 mL saturated aqueous NaHCO$_3$, dried over MgSO$_4$, and concentrated in vacuo. After recrystallization from EtOAc, the yield was 250 mg (64%) of a colorless solid with the following properties: LC-MS (C-18) indicates 96.3% purity (M($^{35}$Cl)+H)=391.8, (M($^{37}$Cl)+H)=393.8. IR: 3272, 1673, 1458, 1422, 1246, 1064 and 732 cm$^{-1}$.

EXAMPLE 56

Preparation of (R,S)-3-(3-oxo-3-pyrrolidinylpropyl)-2H,6aH-pyrrolidino[2",1"-3',2']1,3-oxazino[5',6'-4,5]benzo[e]1,3-oxazaperhydroine-4,10-dione

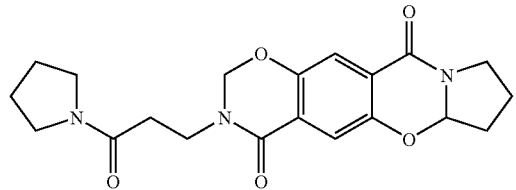

To 2.5 g (10 mmol) salicylic acid intermediate (See Example 46 for the hydrolysis of the ethyl salicylate from Example 7) in 40 mL of DMF was added 1.8 g (11 mmol) CDI under argon atmosphere with stirring. The resulting suspension was heated to 85-100° C. at which point it became a homogeneous brown solution. After 5 hr at the same temperature, 3.0 g β-alanine HCl was added followed by 5 mL of diisopropyl ethyl amine, and the resulting solution was stirred overnight at room temperature. The reaction mixture was concentrated at 1 mm Hg/40° C. and the residue partitioned between 200 mL of CH$_2$Cl$_2$ and 100 mL of 1 M aqueous HCl. The aqueous layer was washed with 3×50 mL of CH$_2$Cl$_2$. The combined organic layers were washed with 100 mL of water, dried over Na$_2$SO$_4$, and concentrated in vacuo to yield 3.8 g of a brown oil. Chromatography on 75 g of silica gel with 1 L of EtOAc yielded 1.2 g (34%) of the ester intermediate as a colorless solid with the following properties: CI-MS, M+1=390 amu.

To 1.2 g (3.5 mmol) of the ester suspended in 90 mL of EtOH was added 10 mL of EtOH followed by 10 mL of water and 1.0 mL (10 mmol) 10 N NaOH. After 5 min a bright yellow solution resulted and 30 min later no starting material remained (TLC, EtOAc). The reaction mixture was concentrated in vacuo and the aqueous residue was extracted with 100 mL of EtOAc, acidified to pH 3.0 with 6 N HCl, and then extracted with 3×100 mL of EtOAc. The organic layers were combined, dried over MgSO$_4$, and concentrated in vacuo to yield 1.0 g of carboxylic acid intermediate (91%).

To 1.0 g (3.1 mmol) of the carboxylic acid in 20 ml of DMF was added 0.55 g (3.4 mmol) CDI followed by 12 mg (0.1 mmol) DMAP, under argon atmosphere with stirring. After 4 hr, 2 mL of pyrrolidine was added and the reaction was allowed to continue overnight. DMF was removed in vacuo and the residue was partitioned between 100 mL of CH$_2$Cl$_2$ and 50 mL of 1 M HCl. After drying over MgSO$_4$, the solvent was removed in vacuo to yield 1.2 g of crude amide intermediate. Column chromatography on 50 g of silica gel (EtOAc) yielded 700 mg pure amide intermediate (54%).

To 0.60 g (1.9 mmol) of the amide in 200 mL 40% CH$_2$Cl$_2$/CHCl$_3$ (anhydrous) was added 11 g of trioxane (122 mmol) followed by 4.6 g (20 mmol) camphor sulfonic acid and 18 drops of H$_2$SO$_4$. The reaction mixture was stirred at reflux under argon atmosphere. Water formed in the reaction was removed by 100 g of 3 A molecular sieves contained in a side arm addition funnel. After 4 hr the reaction was complete (TLC, 10% EtOH in EtOAc). The reaction mixture was cooled to room temperature and washed with 100 mL of ice cold 1 M NaOH. The aqueous layer was washed with 2×100 mL of CHCl$_3$. The combined organic layers were washed with 100 mL water, dried over NaSO4, and concentrated in vacuo. Drying the sample overnight under vacuum (0.1 mm Hg) resulted in 600 mg crude bisbenzoxazine. Chromatography on 75 g silica gel with EtOAc yielded 360 mg of colorless solid. The solid was recrystallized by dissolving it in 1 mL of CHCl$_3$ and slowly adding 30 mL of ether. The yield was 260 mg (36%) of colorless crystals with the following properties: MP=170-171° C. IR (thin film): 1665, 1638 and 1453, cm$^{-1}$. $^1$H NMR (500 MHz, CDCl$_3$) δ 7.53 (s, 1H) 7.52 (1H, s), 5.34 (1H, t, J=6.0 Hz), 5.33 (2H, m), 3.84 (1H, m) 3.85 (2H, m) 3.63 (1H, m) 3.45 (2H, t, J=6.7 Hz) 3.38 (2H, t, J=6.6 Hz) 2.71 (2H, m) 2.42 (1H, m) 2.23 (1H, m) 2.14 (1H, m) 1.97 (2H, m), 1.95 (1H, m) and 1.85 ppm (2H, m).

EXAMPLE 57

Preparation of (R,S)-3-(hydroxymethyl)-2H,6aH-pyrrolidino[2",1"-3',2']1,3-oxazino[5',6'-4,5]benzo[e]1,3-oxazaperhydroine-4,10-dione

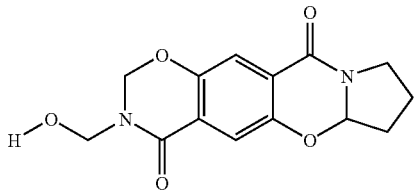

The product (2.7 g; 10 mmol) from Example 7 was heated under argon atmosphere with stirring to 180-200° C. for 3 min with 8.0 g (48.4 mmol) 2,4-dimethoxybenzylamine. After the reaction mixture was cooled to 100° C., it was dissolved in 100 mL CHCl$_3$ and washed with 100 mL of 3 M HCl and 100 mL of water. The organic solution was dried over MgSO$_4$ and concentrated in vacuo to yield 10 g of crude intermediate (one spot on TLC with EtOAc). The crude intermediate was dissolved in 50 mL of TFA under argon atmosphere. After 2 hr no starting material was visible by TLC. The TFA solution was poured slowly into 300 mL of saturated aqueous NaHCO$_3$ and the precipitate was collected by filtration. After drying overnight on the vacuum line, the yield of salicylamide intermediate was 3.0 g.

To 3.0 g of the salicylamide in 20 ml 37% aqueous formaldehyde was added 20 mL of formic acid and the resulting suspension was brought to reflux under argon atmosphere. The resulting solution was refluxed for 3 hr, after which most of the solvent was distilled off. After the resulting residue was cooled to room temperature, it was suspended in 200 mL cold 1 M NaOH. The product was extracted from the aqueous solution with 5×150 mL of CHCl$_3$. The combined organic fractions were dried over NaSO$_4$ and concentrated in vacuo to yield 1.7 g of crude product (mostly one spot on TLC with EtOAc). Chromatography with 1:1 CHCl$_3$/EtOAc on 200 g of silica gel yielded 1.1 g of product (one spot on TLC), which was crystallized from CHCl$_3$/diethyl ether to yield 900 mg of product with the following properties: MP=194-196° C. IR (KBr) 3373, 1677, 1485, 1454 and 1291 cm$^{-1}$. $^1$H NMR (500 MHz CDCl$_3$), δ 7.49 (1H, s) 7.45 (1H, s) 5.46 (1H, t, J=6.0) 5.32 (2H, s) 5.04 (2H, s) 4.05 (1H, br s) 3.84 (1H, m) 3.62 (1H, m) 2.44 (1H, m) 2.26 (1H, m) 2.14 (1H, m) and 1.95 (1H, m) ppm.

EXAMPLE 58

Preparation of (R,S)-2H,3H,6aH-pyrrolidino[2",1"-3',2']1,3-oxazino[5',6'-4,5]benzo[e]1,3-oxazaperhydroine-4,10-dione

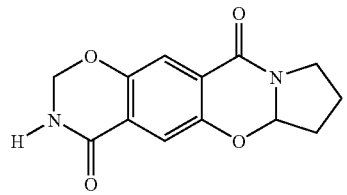

In 40 ml of dry toluene was suspended 158 mg (0.54 mmol) of the product from Example 58 under argon atmosphere with stirring. After refluxing for 1 hr, the reaction mixture was cooled and concentrated in vacuo. The residue was suspended in 20 mL of hexanes and recovered by vacuum filtration to yield 135 mg (95%) of product, which had the following properties: MP=270-275° C. dec. IR: (KBr) 3183, 3055, 1695, 1677, 1664, 1454 and 1069 cm−1. $^1$H NMR (300 MHz, CDCl$_3$) δ 7.57 (1H, s), 7.56, (1H, s), 6.42 (1H, br s), 5.47 (1H, t, J=6.0 Hz), 5.22 (1H, s), 5.21 (1H, s), 3.83 (1H, m) 3.63 (1H, m) 2.45 (1H, s) 2.25 (1H, s) 2.14 (1H, s) and 1.96 ppm (1H, s). LC-MS: (C-18) shows single peak (M+H) 261.

EXAMPLE 59

Preparation of 3,8-bis(2-hydroxyethyl)-2H,7H-1,3-oxazaperhydroino[5',6'-4,5]benzo[e]1,3-oxazine-4,9-dione

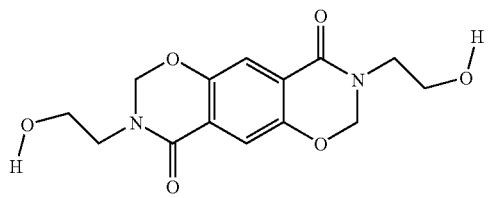

To 40 mL of anhydrous ethanol amine was added 4.0 g (15.7 mmol) of diethyl-(2,5)-dihydroxy terephthalate. The resulting solution was refluxed for 18 h under argon atmosphere. The reaction mixture was cooled to 100° C. and then poured into 200 mL of 3 N HCl. The hot, acidic solution was slowly cooled to room temperature, as copious quantities of pale yellow crystals formed. The solids were collected by vacuum filtration, washed with 3×50 mL cold water, and then dried overnight in vacuo (200 μm Hg) to yield 2.5 g (56%) of diamide intermediate as a pale yellow solid, with the following properties: CI-MS (m+1), 285.1 amu; LC-MS (TIC) indicates 100% purity.

The diamide was dissolved into 20 mL of refluxing anhydrous HCO$_2$H and the solution treated with 40 mL of anhydrous CH$_2$Cl$_2$, 6.0 g (66.7 mmol) trioxane, 1.0 g CuSO$_4$, and 5 drops of H$_2$SO$_4$. The resulting suspension was stirred and refluxed overnight under argon atmosphere. After cooling to room temperature, the reaction mixture was treated with celite, diluted to 300 mL with CH$_2$Cl$_2$ and then filtered. The filtrate was washed with 3×100 mL saturated aqueous NaHCO$_3$, dried over Na$_2$SO$_4$, and dried in vacuo to yield a residue which solidified. Silica gel chromatography of the residue in EtOAc yielded 1.9 grams (33%) of di-formate of the above bis-benzoxazine, as a colorless crystalline solid, with the following properties: CI-MS (m+1) 364.9 amu.

To 1.9 g (5.2 mmol) of the di-formate in 200 mL of hot MeOH was added 12 drops of 10 N aqueous NaOH. The resulting solution was stirred and refluxed for 6 h under argon atmosphere, then cooled to room temperature. The solids which formed upon cooling were collected and washed with 3×20 mL cold MeOH, then dried under vacuum for 18 h at room temperature (200 μm Hg). This yielded 580 mg of the bis-benzoxazine diol (36%). The white fibrous needles had the following properties: MP=237-238° C. IR: 3443, 2953, 1659, 1494, 1452, 1299, 1167, 1050, 1028, 906, 770, 748: LC-MS (CD) indicated 100% purity (TIC) with m+1 at 309.0 amu: $^1$H NMR (300 MHz, DMSO d$^6$), δ 7.37 (1H, s), 5.32 (4H, s), 4.86 (2H, s), and 3.55 ppm (8H, s). $^{13}$C NMR (75.45 MHz) DMSO d$^6$ δ 159.81, 152.00, 123.15, 114.72, 78.95, 59.07 and 47.21 ppm. Another 450 mg of less pure diol was recovered upon concentration of the mother liquors, bringing the hydrolysis yield up to 83%.

EXAMPLE 60

Preparation of 3,8-bis(2-methoxyethyl)-2H,7H--1,3-oxazaperhydroino[5',6'-4,5]benzo[e]1,3-oxazine-4,9-dione

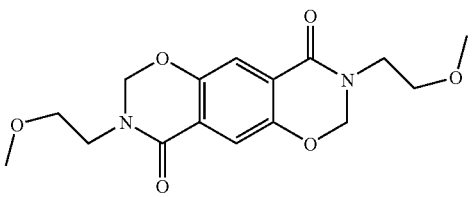

To 405 mg (1.31 mmol) of diol (the product from Example 60) in 15 mL of anhydrous DMF was added 120 mg (3 mmol) of 60% oil dispersed NaH, followed by 5 mL (81 mmol) of MeI. There was a considerable evolution of gas, followed by copious precipitation. The solids redissolved over 20 min to form a clear yellow solution. TLC (1:1, hexane:EtOAc) indicated no starting material. The solvent was removed in vacuo and the residue recrystallized from 15 mL to toluene. This yielded 250 mg (57%) of product with the following properties: MP=149-150° C.: FTIR 2922, 1672, 1487, 1455, 1305, 1103, 1019, 747 cm$^{-1}$: CI-MS: (m+1) 336.9 amu. $^1$H NMR (500 MHz, CDCl$_3$) δ 7.56(2H, s) 5.23 (4H, s), 3.74 (4H, t, J=5.1 Hz), 3.58 (4H, t, J=5.1 Hz) and 3.35 ppm (6H, s).

EXAMPLE 61

Preparation of 3-ethyl-9a-hydro-2H--1,3-oxazaperhydroino[6,5-g]pyrrolidino[2,1-b]quinazoline-4,10-dione

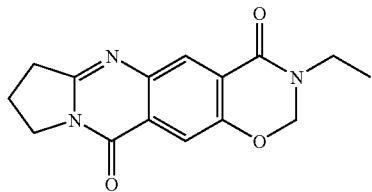

To a well stirred solution of 20 g (84 mmol) diethyl hydroxy terephthalate in 200 mL of anhydrous CHCl$_3$ was added 80 mL (160 mmol) of a 2.0 M solution of AlMe$_3$ in toluene. The addition was performed slowly under argon atmosphere and a room temperature silicone oil bath was used to control temperature. When the rather vigorous gas evolution (CH$_4$) had ceased, the reaction mixture was heated to reflux. After refluxing for 18 h, and cooling to room temperature, the reaction mixture was poured into 500 mL of ice cold 3 N HCl and the resulting suspension stirred for 30 min. After separating the layers the aqueous layer was extracted with 3×200 mL of EtOAc. The combined organic layers were dried over Na$_2$SO$_4$, and concentrated in vacuo, to yield 17 g (86%) of phenolic diamide intermediate. This material was one spot to TLC (EtOAc) and had the following property: FTIR 3283, 1638, 1598, 1552 cm$^{-1}$, KBr.

To 6.5 g (27 mmol) of the phenolic diamide in 200 mL of anhydrous CH$_2$Cl$_2$ was added 6.5 g CuSO$_4$, 2.3 g (10 mmol) camphor sulfonic acid, 36 g (400 mmol) trioxane, and 10 drops H$_2$SO$_4$ with rapid stirring. The resulting suspension was heated to reflux under argon atmosphere and refluxed for 72 hr. The reaction mixture as concentrated to 100 mL by simple distillation at which point no starting material was seen by TLC (EtOAc). The reaction mixture was diluted to 400 mL with CH$_2$Cl$_2$, and then filtered through celite. The filtrate was washed with 100 mL of 1 N NaOH, dried over Na$_2$SO$_4$, and concentrated in vacuo yielding 6.0 g crude benzoxazine intermediate. The crude benzoxazine was chromatographed on 200 g of silica gel (EtOAc) yielding 4.0 g (59%) of intermediate with one spot to TLC and the following property: FTIR 3327, 1664, 1641, 1552, 1428, 1329.

Nitration of the benzoxazine intermediate was performed as follows. To 50 mL H$_2$SO$_4$ at 10° C. was added 2.5 g (10 mmol) benzoxazine with stirring under argon atmosphere. After 30 min at 10° C. a homogeneous solution resulted and 20 mL (443 mmol) of 90% HNO$_3$ was added drop wise. After 45 minutes at the same temperature no starting material remained by TLC (1:1, hexane/EtOAc) and a fine solid had formed in the reaction mixture. The reaction mixture was poured into 200 mL crushed ice. After the ice melted the mixture was extracted with 4×100 mL CHCl$_3$. The chloroform layer was then washed with 200 mL of aqueous NaHCO$_3$, dried over Na$_2$SO$_4$, and concentrated in vacuo to yield 2.8 g of a pale yellow solid. The solid was recrystallized by dissolving it in 30 mL of hot chloroform and diluting the solution to 150 mL with ether. After cooling to room temperature, 2.3 g (78%) of solid nitro-benzoxazine intermediate and was collected by vacuum filtration. It had the following properties: one spot on TLC (1:1 hexane/EtOAc). $^1$H NMR (500 MHz, CDCl$_3$) δ 8.47 (1H, s), 7.06 (1H, s), 6.33 (1H, m) 5.30 (2H, s) 3.59 (2H, q, J=4.32 Hz), 3.50 (2H, q, J=4.22 Hz) 1.28 (3H, t, J=4.62 Hz) and 1.26 ppm (3H, t, J=4.35 Hz).

To 2.0 g (6.6 mmol) of nitro-benzoxazine in 60 mL of 20% HOAc/OAc$_2$ was slowly added 15 g (220 mmol) of NaNO$_2$. The addition was performed over 2 h in small portions, with good stirring at 5-10° C. The reaction mixture was allowed to sit at 0° C. for 18 h, at which point the TLC (1% EtOH/EtOAc) indicated a complete consumption of starting material. The mixture was diluted to 500 mL with sat aqueous NaHCO$_3$, then extracted with 4×100 mL to CH$_2$Cl$_2$ which was dried over Na$_2$SO$_4$ and concentrated in vacuo. The yield was 1.9 g (98%) of solid nitro-benzoxazine ester. This material had the following properties: FTIR 1725, 1679, 1532, 1342 cm$^{-1}$. CI-MS: (m+1) 295 amu. $^1$H NMR (500 MHz, CDCl$_3$) δ 8.90 (1H, s), 7.14 (1H, s), 5.35 (2H, s), 3.99 (2H, q, J=4.2 Hz), 3.66 (2H, q, J=4.3 Hz) 1.27 (3H, t, J=4.4 Hz) and 1.12 ppm (3H, t, J=4.3 Hz).

To 1.0 g (3.4 mmol) the nitrobenzoxazine ester in 40 mL of argon-sparged EtOAc was added 500 mg of 10% Pd/C catalyst and the resulting suspension was hydrogenated for 2 h at 50-60 psi. The catalyst was removed by filtration and the solvent was removed in vacuo, as TLC indicated no starting material. The 900 mg (100%) of colorless solid aniline intermediate was 91% pure by LC-MS (TIC) and one spot on TLC.

To 400 μl (5 mmol) 2-pyrrolidinone in 15 mL of anhydrous toluene under argon atmosphere, was added drop wise 250 in of POCl$_3$ with stirring. After 1 hr at room temperature, 1.1 g (4.2 mmol) of aniline (pooled) was added and the reaction mixture was refluxed under argon atmosphere for 6 hr, at which point no starting material was present by TLC (EtOAc). The reaction mixture was cooled to room temperature and treated with 50 mL of saturated NaHCO$_3$. The aqueous layer was extracted with 5×50 mL of CHCl$_3$ and the organic layers were combined, dried over MgSO$_4$ and concentrated in vacuo to yield 1.3 g of a semi-solid crude product. The crude product was chromatographed on 50 g of silica gel to yield 400 mg (33%) of pale brown product with the following properties: MP=252-253° C.: FTIR 1659, 1453 and 1294 cm$^{-1}$. CI-MS (m+1) 286 amu: $^1$H NMR (500 MHz, CDCl$_3$) δ8.27 (1H, s), 7.80 (1H, s), 5.26 (2H, s), 4.19 (2H, t, J=7.3 Hz), 3.65 (2H, q, J=7.2 Hz), 3.18 (2H, t, J=7.6 Hz), 2.30 (2H, m, J=7.6) and 1.28 ppm (3H, t, J=7.2).

EXAMPLE 62

Preparation of (R,S)-6-(pyrrolidinylcarbonyl)-3aH-benzo[e]pyrrolidino[2,1-b]1,3-oxazin-9-one

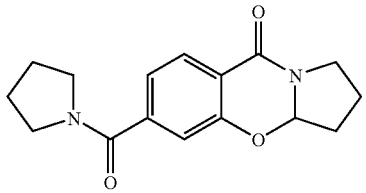

To 1.5 g (6 mmol) of the product from Example 3 in 40 mL of dry, room temperature, toluene was added, under argon atmosphere, 0.75 mL pyrrolidine (9 mmol) followed by 4.5 mL 2.0 molar Me$_3$Al in hexanes (9.0 mmol). After stirring for 0.5 hr, the reaction mixture was heated and refluxed for 3 hr, at which point no starting material remained (TLC, EtOAc). The reaction mixture was cooled to 10° C. and stirred with 50 mL of 1 M HCl along with 200 mL of EtOAc. The aqueous layer was extracted with 3×100 mL of EtOAc. The combined organic layers were washed with 50 mL of brine, 50 mL 1 M aqueous NaOH, 2×50 mL brine, and then dried over MgSO$_4$. After removal of the solvent and chromatography on 100 g silica gel, the product yield was 0.700 g (70%).

EXAMPLES 63-76

The following compounds were synthesized by procedures essentially similar to their congeners of the previously described examples employing reactions and methods known to the skilled artisan. All products were found to exhibit desirable activity in the electrophysiological screen for activity on the AMPA receptor as described above. In all cases the associated value for EC$_{2x}$ (as described in Table 2 above) was less than 10 μM.

EXAMPLE 63

(R,S)-2,2,3-trimethyl-6aH-pyrrolidino[2",1"-3',2']1,3-oxazaperhydroino[5',6'-4,5]benzo[e]1,3-oxazine-4,10-dione $^1$HNMR (300 MHz, CDCl$_3$) δ 7.54 (1H, s), 7.46 (1H, s), 5.47 (1H, t, J=5.8 Hz), 3.83 (1H, m), 3.61 (1H, m), 3.07 (3H, s), 2.45 (1H, m), 2.26 (1H, m), 2.14 (1H, m) 1.96 (1H, m), 1.65 (3H, s) and 1.59 ppm (3H, s).

EXAMPLE 64

(R,S)-3-cyclopropyl-2H,6aH-pyrrolidino[2",1"-3',2']1,3-oxazaperhydroino[5',6'-5,4]benzo[e]1,3-oxazine-4,10-dione $^1$HNMR (300 MHz, CDCl$_3$) δ 7.57 (1H, s), 7.51 (1H, s), 5.45 (1H, t, J=5.8 Hz), 5.17 (2H, s), 3.83 (1H, m), 3.62 (1H, m), 2.69 (1H, m), 2.44 (1H, m), 2.27 (1H, m), 2.13 (1H, m), 1.95 (1H, m), 0.95 (2H, m) and 0.81 ppm (2H, m).

EXAMPLE 65

(R,S), (R,S)-8-hydroxy-3-methyl-2H,6aH-pyrrolidino[2",1"-3',2']1,3-oxazaperhydroino[5',6'-5,4]benzo[e]1,3-oxazine-4,10-dione $^1$HNMR (300 MHz, CDCl$_3$) δ 7.55 (1H, s), 7.49 (1H, s), 5.51 (1H, dd, J=3 Hz and 6.6 Hz), 5.16 (2H, m), 4.54 (1H, m), 4.05 (1H, m), 3.60 (1H, dd, J=4.5 Hz and 12.6 Hz), 3.12 (3H, s) and 2.42-2.66 ppm (2H, m).

EXAMPLE 66

(R,S), (R,S)-2-[(2-oxopyrrolidinyl)methyl]-2H,3H,6aH-pyrrolidino[2",1"-3',2']1,3-oxazaperhydroino[5',6'-4,5]benzo[e]1,3-oxazine-4,10-dione $^1$HNMR (300 MHz, CDCl$_3$) δ 7.553 (0.5H, 5), 7.543 (0.5H, s), 7.540 (0.5H, s), 7.524 (0.5H, s), 7.120 (0.5H, br s), 7.084 (0.5H, br, s), 5.464 (1H, td, J=6.3 Hz, J=1.2 Hz), 5.40 (1H, m), 3.5-4.0 (6H, m), 2.4-2.55 (3H, m) and 1.90-2.34 ppm (5H, m).

EXAMPLE 67

(3R), (R,S)-3-benzyl-2H,7aH-pyrrolidino[2",1"-2',3']1,3-oxazaperhydroinio[5',6'-5,4]benzo[f]1,4-oxazepine-5,11-dione $^1$HNMR (300 MHz, CDCl$_3$) δ 7.63-7.15 (7H, m), 6.23 (1H, NH), 5.46 (1H, t, J=5.9 Hz), 4.28-4.16 (2H, m), 3.88-3.80 (2H, m), 3.66-3.58 (1H, m), 2.96-2.76 (2H, m), 2.48-2.39 (1H, m) and 2.31-1.90 ppm (31H, m).

EXAMPLE 68

(R,S)-4-methyl-2H,3H,7aH-pyrrolidino[2",1"-3',2']1,3-oxazaperhydroino[5',6'-4,5]benzo[f]1,4-oxazepine-5,11-dione $^1$HNMR (300 MHz, CDCl$_3$) δ 7.57 (1H, s), 7.35 (1H, s), 5.47 (1H, t, J=5.9 Hz), 4.43-4.27 (2H, m), 3.88-3.80 (1H, m), 3.66-3.52 (2H, m), 3.44-3.36 (1H, m), 3.22 (3H, s), 2.50-2.40 (1H, m) and 2.32-1.87 ppm (3H, m).

EXAMPLE 69

(R,S)-2H,3H,4H,7aH-pyrrolidino[2",1"-3',2']1,3-oxazaperhydroino[5',6'-4,5]benzo[f]1,4-oxazepine-5,11-dione $^1$HNMR (300 MHz, CDCl$_3$) δ 7.61 (1H, s), 7.46 (1H, s), 6.81 (1H, NH), 5.47 (1H, t, J=5.7 Hz),4.40-4.27(2H, m), 3.89-3.80(1H, m),3.66-3.58 (1H, m), 3.51-3.38 (2H, m), 2.49-2.40 (1H, m) and 2.32-1.88 ppm (3H, m).

EXAMPLE 70

(3R), (R,S)-3-((1S)-1-hydroxy-2-methoxyethyl)-6aH-chromano[7,6-e]pyrrolidino[2,1-b]1,3-oxazaperhydroine-4,10-dione $^1$HNMR (300 MHz, CDCl$_3$) δ 7.56 (1H, s), 7.46 (1H, s), 5.44 (1H, t, J=5.7 Hz), 4.62-4.57 (1H, m), 4.42-4.34 (1H, m), 4.23-4.15 (1H, m), 3.89-3.80 (1H, m), 3.66-3.55 (2H, m), 3.40 (3H, s), 3.24-3.04 (2H, m), 2.50-2.40 (1H, m) and 2.30-1.87 ppm (3H, m).

EXAMPLE 71

(R,S)-3-(2-methoxyethyl)-2H,6aH-pyrrolidino[2",1"-3',2']1,3-oxazaperhydroino[5',6'-5,4]benzo[e]1,3-oxazine-4,10-dione $^1$H NMR (300 MHz, CDCl$_3$) δ 7.55 (1H, s), 7.52 (1H, s), 5.46 (1H, t, J=5.9 Hz), 5.23 (2H, s), 3.84 (1H, dt, J=12.1 and 7.0 Hz), 3.73 (2H, m), 3.63 (1H, m), 3.57 (2H, t, J=4.8 Hz), 3.35 (31H, s), 2.44 (1H, m), 2.25 (1H, m), 2.14 (1H, m) and 1.96 ppm (1H, m).

EXAMPLE 72

(R,S)-3-(2-phenylethyl)-2H,6aH-pyrrolidino[2",1"-2',3']1,3-oxazaperhydroino[5',6'-5,4]benzo[e]1,3-oxazine-4,10-dione $^1$HNMR (300 MHz, CDCl$_3$) δ 7.55 (1H, s), 7.48 (1H, s), 7.23 (5H, m), 5.45 (1H, t, J=5.9 Hz), 4.87 (2H, s), 3.83 (1H, m), 3.78 (2H, t, J=7.3 Hz), 3.61 (1H, m), 2.95 (2H, t, J=7.3 Hz), 2.44 (1H, m), 2.24 (1H, m), 2.12 (1H, m) and 1.95 ppm (1H, m).

EXAMPLE 73

(R,S)-3-(3-imidazolylpropyl)-2H,6aH-pyrrolidino[2",1"-2',3']1,3-oxazaperhydroino[5',6'-5,4]benzo[e]1,3-oxazine-4,10-dione $^1$HNMR (300 MHz, CDCl$_3$) δ 7.56 (1H, s), 7.55 (1H, s), 7.53 (1H, s), 7.08 (1H, s), 6.98 (1H, s), 5.47 (1H, t, J=5.9 Hz), 5.11 (1H, d, J=11.4 Hz), 5.08 (1H, d, J=11.0 Hz), 4.04 (2H, t, J=7.0 Hz), 3.85 (1H, dt, J=11.7 and 7.3 Hz), 3.62 (1H, m), 3.53 (2H, m), 2.45 (1H, m), 2.26(1H, m), 2.14(2H, t, J=7.0 Hz), 2.13 (1H, m) and 1.95 ppm (1H, m).

EXAMPLE 74

(R,S)-3-(2-(2-pyridyl)ethyl)-2H,6aH-pyrrolidino[2",1"-2',3']1,3-oxazaperhydroino[5',6'-5,4]benzo[e]1,3-oxazine-4,10-dione $^1$HNMR (300 MHz, CDCl$_3$) δ 8.54 (1H, d, J=4.4 Hz), 7.60 (1H, td, J=7.3 and 1.5 Hz), 7.54 (1H, s), 7.47 (1H, s), 7.17 (2H, m), 5.45 (1H, t, J=5.9 Hz), 4.97 (2H, s), 3.97 (2H, t, J=7.0 Hz), 3.84 (1H, dt, J=11.7 and 7.3 Hz), 3.61 (1H, m), 3.15 (2H, t, J=7.0 Hz), 2.44 (1H, m), 2.27 (1H, m), 2.13 (1H, m) and 1.96 ppm (1H, m).

EXAMPLE 75

(R,S)-3-(2-(2-thienyl)ethyl)-2H,6aH-pyrrolidino[2",1"-3',2']1,3-oxazaperhydroino[5',6'-5,4]benzo[e]1,3-oxazine-4,10-dione $^1$HNMR (300 MHz, CDCl$_3$) δ 7.56 (1H, s), 7.50(1H, s), 7.16 (1H, d, J=5.1 Hz), 6.92 (1H, m), 6.86 (1H, d, J=3.7 Hz), 5.46 (1H, t, J=5.9 Hz), 4.93 (2H, s), 3.84 (1H, m), 3.80 (2H, t, J=6.6 Hz), 3.62 (1H, m), 3.20 (2H, t, J=6.6 Hz), 2.44 (1H, m), 2.27 (1H, m), 2.12 (1H, m) and 1.96 ppm (1H, m).

EXAMPLE 76

(R,S)-3-(2-(3-pyridyl)ethyl)-2H,6aH-prrolidino[2",1"-2',3']1,3-oxazaperhydroino[5',6'-5,4]benzo[e]1,3-oxazine-4,10-dione $^1$HNMR (300 MHz, CDCl$_3$) δ 8.50 (2H, m), 7.58 (1H, ddd, J=7.7, 2.2, and 1.6 Hz), 7.55 (1H, s), 7.51 (1H, s), 7.24 (1H, ddd, J=7.9, 4.9, and 0.9 Hz), 5.46 (1H, t, J=5.9 Hz), 4.98 (1H, d, J=10.2 Hz), 4.96 (1H, d, J=10.2 Hz), 3.80 (3H, m), 3.62 (1H, m), 2.97 (2H, t, J=7.0 Hz), 2.44 (1H, m), 2.28 (1H, m), 2.13 (1H, m) and 1.97 ppm (1H, m).

EXAMPLE 77

Enantiomeric Resolution of the Compound of Example 1

Resolution of the three components of Example 1 was achieved by a combination of fractional crystallization and column chromatography on a chiral support. A 0.7 g sample was dissolved in 20 mL CH$_2$Cl$_2$ and diluted with 7 mL CCl$_4$. The volume was reduced to 25 mL by warming and further diluted with 4 mL CCl$_4$. The solution was evaporated by warming until crystallization began, and then allowed to cool to ambient. The collected crystals were washed with CCl$_4$/CH$_2$Cl$_2$ and CCl$_4$. Weight of the predominately meso form was 165 mg. The mother liquor was further concentrated and diluted with CCl$_4$ in order to induce crystallization of a second crop of material, which was collected and washed with CCl$_4$ to yield 178 mg of material that contained only about 8% of the meso form.

Material (19.8 mg) from the second crop above was dissolved in 2 mL warm ethanol, of which 0.5 mL was injected onto a Chiralpak AD (Daicel) column (20 mm×250 cm) and eluted with a gradient of 25-40% ethanol/hexane at 3 mL/min. Fractions from multiple injections were pooled and crystallized to yield 5.84 mg of the first enantiomer (1A), which was active on the AMPA receptor by electrophysiological analysis and 3.51 mg of the second enantiomer (1B), which demonstrated significantly less activity than the first eluted enantiomer.

EXAMPLE 78

In vitro Physiological Testing

The physiological effects of invention compounds were tested in vitro on primary cultures of rat cortical neurons as described by Hamill, O P, et al. in *Pflügers Arch* 391: 85-100 (1981) or on slices of rat hippocampus according to the following procedure. Excitatory responses (field EPSPs) were measured in hippocampal slices, which were maintained in a recording chamber continuously perfused with artificial cerebrospinal fluid (ACSF). During a 15-30 minute interval, the perfusion medium was switched to one containing various concentrations of the test compounds. Responses collected immediately before and at the end of drug perfusion were superimposed in order to calculate the percent increase in EPSP amplitude.

To conduct these tests, the hippocampus was removed from anesthetized, 2 month old Sprague-Dawley rats and in vitro slices (400 μm thick) were prepared and maintained in an interface chamber at 35° C. using conventional techniques [see, for example, Dunwiddie and Lynch, *J. Physiol.* 276: 353-367 (1978)]. The chamber was constantly perfused at 0.5 mL/min with ACSF containing (in mM): NaCl 124, KCl 3, $KH_2PO_4$ 1.25, $MgSO_4$ 2.5, $CaCl_2$ 3.4, $NaHCO_3$ 26, glucose 10 and L-ascorbate 2. A bipolar nichrome stimulating electrode was positioned in the dendritic layer (stratum radiatum) of the hippocampal subfield CA1 close to the border of subfield CA3.

Current pulses (0.1 msec) through the stimulating electrode activate a population of the Schaffer-commissural (SC) fibers, which arise from neurons in the subdivision CA3 and terminate in synapses on the dendrites of CA1 neurons. Activation of these synapses causes them to release the transmitter glutamate. Glutamate binds to the post-synaptic AMPA receptors, which then transiently open an associated ion channel and permit a sodium current to enter the postsynaptic cell. This current results in a voltage in the extracellular space (the field EPSP) which is recorded by a high impedance recording electrode positioned in the middle of the stratum radiatum of CA1.

For the experiments summarized in the table, the intensity of the stimulation current was adjusted to produce half-maximal EPSPs (typically about 1.5-2.0 mV). Paired stimulation pulses were given every 40 s with an interpulse interval of 200 msec (see below). The field EPSPs of the second response were digitized and analyzed to determine amplitude. If the responses were stable for 15-30 minutes (baseline), test compounds were added to the perfusion lines for a period of about 15 minutes. The perfusion was then changed back to regular ACSF.

Paired-pulse stimulation was used since stimulation of the SC fibers, in part, activates interneurons which generate an inhibitory postsynaptic potential (IPSP) in the pyramidal cells of CA1. This feed forward IPSP typically sets in after the EPSP reaches its peak. It accelerates the repolarization and shortens the decay phase of the EPSP, and thus could partially mask the effects of the test compounds. One of the relevant features of the feed-forward IPSP is that it can not be reactivated for several hundred milliseconds following a stimulation pulse. This phenomenon can be employed to advantage to eliminate IPSP by delivering paired pulses separated by 200 ms and using the second ("primed") response for data analysis.

The first data column of Table 1 shows the estimate of the concentration of each test compound that would be required to increase the amplitude of the field EPSP to a value 10% above the baseline level. Values were estimated by interpolation in most cases, but by extrapolation from determined values for others.

EXAMPLE 79

Behavioral Testing

The third data column in Table 1 shows the MED for efficacy to improve performance in the eight-arm radial maze task, which tests for improved memory and cognition ($MED_C$). This test has been described previously by Staubli et al., *PNAS* 91:777-781 (1994) and Lynch and Rogers, U.S. Pat. No. 5,747,492.

While the invention has been described with reference to specific methods and embodiments, it will be appreciated that various modifications may be made without departing from the invention.

What is claimed is:
1. A compound having the Structure Ia or Ib:

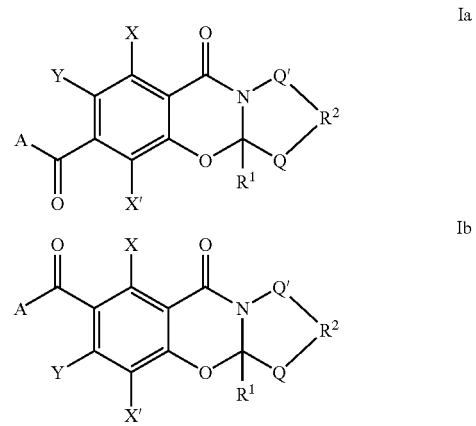

wherein:
Q and Q' are independently hydrogen, —$CH_2$—, —O—, —S—or alkyl, or, when Y or $R^3$ serve to link the aromatic ring to A, hydroxyalkyl or alkoxyalkyl, $R^1$ is hydrogen, alkyl or together with Q may be a cycloalkyl ring, $R^2$ is absent when Q and Q' are independently hydrogen, alkyl, hydroxyalkyl or alkoxyalkyl, or if present, is —$CH_2$—, —CO—, —$CH_2CH_2$—, —$CH_2CO$—, —$CH_2O$—, —CRR'—, or —CONR—, Y is hydrogen or —$OR^3$, or serves to link the aromatic ring to A or A' as a single bond, =N— or —NR—, $R^3$ is hydrogen, alkyl, substituted alkyl, or serves to link the attached oxygen to A or A' by being a lower alkylene or substituted lower alkylene linking the aromatic ring to A or A' to form a substituted or unsubstituted 6, 7 or 8—membered ring, or a bond linking the oxygen to A or A' in order to form a 5—or 6—membered ring, A is —NRR', —OR, alkyl, substituted alkyl, cycloalkyl, substituted cycloalkyl, cycloalkylalkyl, aryl, substituted aryl, a heterocycle or a substituted heterocycle containing one or two heteroatoms selected from the group consisting of oxygen, nitrogen, sulfur and mixtures thereof, A' is —NRR', R is hydrogen, aryl, arylalkyl, substituted aryl, substituted arylalkyl, alkyl, substituted alkyl, cycloalkyl, substituted cycloalkyl, or heterocycloalkyl, R' is absent or is hydrogen, aryl, arylalkyl, substituted aryl, substituted arylalkyl, alkyl, substituted alkyl, cycloalkyl, substituted cycloalkyl or may join together with R to form a 4- to 8- membered ring, which may be substituted by X and may be linked to Y to form a 6-membered ring and which may optionally contain one or two heteroatoms selected from the group consisting of oxygen, nitrogen, sulfur and mixtures thereof, X and X' are independently R, halo, —$CO_2R$, —CN, —NRR', —NRCOR', —$NO_2$, —$N_3$ or —OR.

2. A compound according to claim 1 with the structure Ia above wherein:

$R^1$ is hydrogen, alkyl or together with Q may be a cycloalkyl ring, $R^2$ may be absent, or if present is —$CH_2$—, —CO—, $CH_2CH_2$, —$CH_2CO$—, —$CH_2O$—, or —CONR—, Y is hydrogen or —OR$^3$, or serves to link the aromatic ring to A as a single bond, =N— or —NR—, R$^3$ is hydrogen, alkyl, substituted alkyl, or serves to link the attached oxygen to A by being a lower alkylene or substituted lower alkylene linking the aromatic ring to A to form. a substituted or unsubstituted 6, 7 or 8- membered ring, or a bond linking the oxygen to A in order to form, a 5- or 6- membered ring, A is —NRR', —OR, alkyl, substituted alkyl, cycloalkyl, substituted cycloalkyl, cycloalkylalkyl, aryl, substituted aryl, a heterocycle or a substituted heterocycle containing one or two heteroatoms, R is hydrogen, aryl, arylalkyl, substituted aryl, substituted arylalkyl, alkyl, substituted alkyl, cycloalkyl, substituted cycloalkyl, or heterocycloalkyl, R' is absent or is hydrogen, aryl, arylalkyl, substituted aryl, substituted arylalkyl, alkyl, substituted alkyl, cycloalkyl, substituted cycloalkyl or may join together with R to form a 4- to 8- membered ring, which may be substituted by X and may be linked to Y and which may optionally contain one or two heteroatoms, and X and X' are independently R, halo, —CO$_2$R, —CN, —NRR', —NRCOR', —NO$_2$, —N$_3$ or —OR.

3. A compound according to claim 1 with the structure Ib above wherein:

Q and Q' are independently hydrogen, —CH$_2$—, —O—, —S—, or alkyl,

R' is hydrogen, alkyl or together with Q may be a cycloalkyl ring,

R$^2$ may be absent, or if present is —CH$_2$—, —CO—, —CH$_2$CH$_2$—, —CH$_2$CO—, —CH$_2$O—, or —CONR—, Y is hydrogen or —OR$^3$, or serves to link the aromatic ring to A' as a single bond, =N—or —NR—, R$^3$ is hydrogen, alkyl, substituted alkyl, or serves to link the attached oxygen to A' by being a lower alkylene or substituted lower alkylene linking the aromatic ring to A' to form a substituted or unsubstituted 6, 7 or 8-membered ring, or a bond linking the oxygen to A' in order to form a 5- or 6-membered ring, A' is —NRR';

R is hydrogen, aryl, arylalkyl, substituted aryl, substituted arylalkyl, alkyl, substituted alkyl, cycloalkyl, substituted cycloalkyl, or heterocycloalkyl, R' is absent or is hydrogen, aryl, arylalkyl, substituted aryl, substituted arylalkyl, alkyl, substituted alkyl, cycloalkyl, substituted cycloalkyl or may join together with R to form a 4- to 8-membered ring, which may be substituted by X and may be linked to Y to form a 6-membered ring and which may optionally contain one or two heteroatoms, and X and X' are independently R, halo, —CO$_2$R, —CN, —NRR', —NRCOR', —NO$_2$, —N$_3$ or —OR.

4. A compound according to any one of claims 1-3 in which Q and Q' are —CH$_2$— and R$^2$ is —CH$_2$—.

5. A compound according to any one of claims 1-3 in which R$^1$ is hydrogen.

6. A compound according to any one of claims 1-3 wherein Q and Q' are —CH$_2$— and R$^2$ is —CH$_2$CH$_2$—.

7. A compound according to any one of claims 1-3 in which Q' is —CH$_2$—, R$^2$ is —CH$_2$—and Q is —O— or —S—.

8. A compound according to any one of claims 1-3 in which Q is —O—.

9. A compound according to any one of claims 1-3 in which Q and Q' are alkyl and R$^2$ is absent.

10. A compound according to any one of claims 1-3 in which Q and Q' are alkyl, R$^2$ is absent and R$^1$ is hydrogen.

11. A compound according to any one of claims 1-2 in which Y is —OR$^3$ and A is —NRR', —OR, alkyl, substituted alkyl, cycloalkyl substituted cycloalkyl, cycloalkylalkyl, aryl, substituted aryl, a heterocycle or a substituted heterocycle containing one or two heteroatoms.

12. A compound according to any one of claims 1-2 in which A is alkyl, substituted alkyl, cycloalkyl, substituted cycloalkyl, cycloalkylalkyl, aryl, substituted aryl, a heterocycle or a substituted heterocycle containing one or two heteroatoms.

13. A compound according to any one of claims 1-2 in which A is alkyl, substituted alkyl, cycloalkyl, substituted cycloalkyl, cycloalkylalkyl, a heterocycle or a substituted heterocycle.

14. A. compound according to any one of claims 1-3 in which A or A' is —NRR', R is hydrogen, aryl, arylalkyl, substituted aryl, substituted arylalkyl, alkyl, substituted alkyl, cycloalkyl, substituted cycloalkyl, or heterocycloalkyl, R' is hydrogen, aryl, arylalkyl, substituted aryl, substituted arylalkyl, alkyl, substituted alkyl, cycloalkyl, substituted cycloalkyl or may join together with R to form a 4- to 8-membered ring, which may be substituted by X and linked to Y by R$^3$ and which may optionally contain one additional heteroatom and X and X' are independently R, halo, —CO$_2$R, —CN, —NRR', —NRCOR', —NO$_2$, —N$_3$ or —OR.

15. A compound according to any one of claims 1-3 in which A or A' is —NRR', R is alkyl, substituted alkyl, cycloalkyl, substituted cycloalkyl, or heterocycloalkyl, R' is hydrogen, alkyl, substituted alkyl, cycloalkyl, substituted cycloalkyl or may join together with R to form a 4- to 8-membered ring, which may be substituted by X and linked to Y by R$^3$ and which may optionally contain, one additional heteroatom and X and X' are independently R, halo, —CO$_2$R, —CN, —NRR', —NRCOR', —NO$_2$, —N$_3$ or —OR.

16. A compound according to claim 15 in which A or A' is —NRR' and R' is joined together with R to form a 4-to 8-membered ring, which may be substituted by X and linked to Y by R$^3$ and which may optionally contain one additional heteroatom and X and X' are independently R, halo, —CO$_2$R, —CN, —NRR', —NRCOR', —NO$_2$, —N$_3$ or —OR.

17. A compound according to claim 16 in which A or A' is —NRR', and R' is joined together with R to form a 5-membered ring, which may be substituted by X and linked to Y by R$^3$ and which may optionally contain one additional heteroatom and X and X' are independently R, halo, —CO$_2$R, —CN, —NRR', —NRCOR', —NO$_2$, —N$_3$ or —OR.

18. A compound according to claim 17 in which A or A' is —NRR', and R' is joined together with R to form a 5-membered ring, which may be substituted by X and linked to Y by R$^3$ and which may optionally contain one additional heteroatom and X and X' are independently R, halo, —CO$_2$R, —CN, —NRR', —NRCOR', —NO$_2$, —N$_3$ or —OR.

19. A compound according to claim 18 in which A or A' is —NRR', and R' is joined together with R to form a 5-membered ring, which is linked to Y by R$^3$.

20. A compound according to claim 16 in which A or A' is —NRR', and R' is joined together with R to form a 6-membered ring, which may be substituted by X and linked to Y by R$^3$ and which may optionally contain one additional heteroatom and X and X' are independently R, halo, —CO$_2$R, —CN, —NRR', —NRCOR', —NO$_2$, —N$_3$ or —OR.

21. A compound according to any one of claims 1-3 wherein Y is —OR$^3$.

22. A compound according to claim 21 wherein R$^3$ is hydrogen.

23. A compound according to any one of claims 1-3 wherein Y is hydrogen.

24. A compound according to any one of claims 1-3 wherein Y is =N— or —NR—.

25. A compound according to any one of claims 1-3 wherein Y is =N—.

26. A compound according to claim 23 wherein A or A' is —NRR'.

27. A compound according to claim 21 wherein A or A' is —NRR'.

28. A compound according to claim 24 wherein A or A' is —NRR'.

29. A compound according to claim 28 wherein $R^1$ is hydrogen.

30. A method of treating a mammalian subject, wherein the subject suffers from a hypoglutamatergic condition or a deficiency in the number or strength of excitatory synapses or in the number of AMPA receptors, such that memory or other cognitive functions are impaired, said method comprising administering to said subject an effective amount of a compound according to claim 1.

31. A method of treating a mammalian subject wherein the subject suffers from a hypoglutamatergic condition or deficiencies in the number or strength of excitatory synapses or in. the number of AMPA receptors such that a cortical/striatal imbalance occurs leading to schizophrenia or schizophreniform behavior, said method comprising administering to said subject an effective amount of a compound according to claim 1.

32. The method according to claim 31 wherein said condition is schizophrenia.

33. The method according to claim 30 wherein said condition is Parkinson's disease.

34. A pharmaceutical composition comprising a compound according to claim 1 in combination with a pharmaceutically acceptable carrier, additive or excipient.

35. The composition according to claim 34 wherein said compound comprises about 0.5% to about 75% by weight of said composition and said carrier, additive or excipient comprises about 25% to about 95.5% of said composition.

36. A compound according to claim 5 wherein Q and Q' are —$CH_2$— and $R^2$ is —$CH_2CH_2$—.

37. A compound according to claim 5 in which Q' is —$CH_2$—, $R^2$ is —$CH_2$— and Q is —O— or —S—.

38. A compound according to claim 1 or 2 wherein A is —OR, alkyl, substituted alkyl, cycloalkyl, substituted cycloalkyl, cycloalkylalkyl, a heterocycle or a substituted heterocycle containing one or two heteroatoms and Y is hydrogen.

39. A compound according to claim 1 or 2 wherein A is —OR, alkyl, substituted alkyl, cycloalkyl, substituted cycloalkyl, cycloallcylalkyl, a heterocycle or a substituted heterocycle containing one or two heteroatoms and Y is —$OR^3$.

40. A method of treating a mammalian subject, wherein the subject suffers from a hypoglutamatergic condition or a deficiency in the number or strength of excitatory synapses or in the number of AMPA receptors, such that memory or other cognitive functions are impaired, said method comprising administering to said subject an effective amount of a compound according to claim 2.

41. A method of treating a mammalian subject, wherein the subject suffers from a hypoglutamatergic condition or a deficiency in the number or strength of excitatory synapses or in the number of AMPA receptors, such that memory or other cognitive functions are impaired, said method comprising administering to said subject an effective amount of a compound according to claim 3.

42. A method of treating a mammalian subject wherein the subject suffers from a hypoglutamatergic condition or deficiencies in the number or strength of excitatory synapses or in the number of AMPA receptors such that a cortical/striatal imbalance occurs leading to schizophrenia or schizophreniform behavior, said method comprising administering to said subject an effective amount of a compound according to claim 2.

43. A method of treating a mammalian subject wherein the subject suffers from a hypoglutamatergic condition or deficiencies in the number or strength of excitatory synapses or in the number of AMPA receptors such that a cortical/striatal imbalance occurs leading to schizophrenia or schizophreniform behavior, said method comprising administering to said subject an effective amount of a compound according to claim 3.

44. The method according to claim 42 or 43 wherein said condition is schizophrenia.

45. The method according to claim 40 or 41 wherein said condition is Parkinson's disease.

46. A pharmaceutical composition comprising a compound according to claim 2 or 3 in combination with a pharmaceutically acceptable carrier, additive or excipient.

47. The composition according to claim 46 wherein said compound comprises about 0.5% to about 75% by weight of said composition and said carrier, additive or excipient comprises about 25% to about 95.5% of said composition.

* * * * *